US007332498B2

(12) United States Patent
Lu et al.

(10) Patent No.: US 7,332,498 B2
(45) Date of Patent: Feb. 19, 2008

(54) MODULATION OF KSP KINESIN ACTIVITY WITH HETEROCYCLIC-FUSED PYRIMIDINONE DERIVATIVES

(75) Inventors: Pu-Ping Lu, Foster City, CA (US); David J. Morgans, Jr., Los Altos, CA (US); Bing Yao, Hayward, CA (US); Dashyant Dhanak, Collegeville, PA (US); Steven David Knight, Collegeville, PA (US)

(73) Assignees: Cytokinetics, Inc., South San Francisco, CA (US); SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 11/284,806

(22) Filed: Nov. 23, 2005

(65) Prior Publication Data
US 2006/0111374 A1     May 25, 2006

Related U.S. Application Data

(63) Continuation of application No. 10/444,283, filed on May 22, 2003, now Pat. No. 7,038,048.

(60) Provisional application No. 60/382,737, filed on May 23, 2002.

(51) Int. Cl.
*A61K 31/519* (2006.01)
*A61K 31/5025* (2006.01)
*C07D 471/04* (2006.01)
*C07D 487/04* (2006.01)
*C07D 498/04* (2006.01)
*C07D 211/78* (2006.01)
*C07D 211/82* (2006.01)
*C07D 211/70* (2006.01)
*C07D 211/90* (2006.01)
*C07D 211/72* (2006.01)
*C07D 211/84* (2006.01)
*C07D 213/84* (2006.01)
*C07D 213/72* (2006.01)
*C07D 213/78* (2006.01)
*C07D 213/46* (2006.01)
*C07D 213/56* (2006.01)

(52) U.S. Cl. ............... 514/262.1; 514/249; 514/264.1; 514/248; 544/279; 544/91; 546/286; 546/287; 546/288; 546/289; 546/304; 546/312; 546/314; 546/315; 546/316; 546/324

(58) Field of Classification Search ............... 544/279; 514/249, 258.1, 264.1
See application file for complete search history.

(56) References Cited

U.S. PATENT DOCUMENTS

| | | | |
|---|---|---|---|
| 3,320,124 A | 5/1967 | Waletzky et al. | |
| 3,322,756 A | 5/1967 | Ruschig et al. | |
| 3,723,432 A | 3/1973 | Ott et al. | |
| 3,740,442 A | 6/1973 | Ott et al. | |
| 3,846,549 A | 11/1974 | Mentrup et al. | |
| 3,925,548 A | 12/1975 | Oh | |
| 3,962,244 A | 6/1976 | Weyer et al. | |
| 4,011,324 A | 3/1977 | Althuis | |
| 4,281,127 A | 7/1981 | LaMahieu et al. | |
| 4,670,560 A | 6/1987 | Press et al. | |
| 4,729,996 A | 3/1988 | Wright et al. | |
| 4,734,419 A | 3/1988 | Hashimoto et al. | |
| 4,808,590 A | 2/1989 | Higa et al. | |
| 4,857,530 A | 8/1989 | Berman et al. | |
| 4,859,670 A | 8/1989 | Kampe et al. | |
| 4,866,084 A | 9/1989 | Gunasekera et al. | |
| 4,970,226 A | 11/1990 | Sun et al. | |
| 4,981,856 A | 1/1991 | Hughes | |
| 4,992,550 A | 2/1991 | Hughes | |
| 5,037,829 A | 8/1991 | Freyne et al. | |

(Continued)

FOREIGN PATENT DOCUMENTS

AU    B-12617/88    9/1988

(Continued)

OTHER PUBLICATIONS http://www.oncolink.com/types/index.cfm, List of cancer types and therapies, Mar. 2007.*

(Continued)

*Primary Examiner*—Mark L. Berch
*Assistant Examiner*—Cecilia M Jaisle
(74) *Attorney, Agent, or Firm*—Finnegan, Henderson, Farabow, Garrett & Dunner, LLP

(57) ABSTRACT

A method of modulating KSP kinesin activity in vitro comprising contacting KSP kinesin with at least one chemical entity chosen from compounds represented by Formula I:

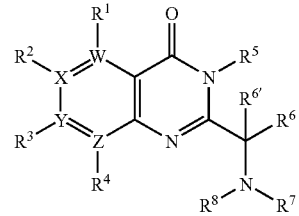

Formula I and pharmaceutically acceptable salts thereof, where the variables are as defined further herein.

10 Claims, No Drawings

U.S. PATENT DOCUMENTS

| | | | |
|---|---|---|---|
| 5,081,124 A | 1/1992 | Hughes |
| 5,147,875 A | 9/1992 | Coates |
| 5,158,959 A | 10/1992 | Geiger et al. |
| 5,187,167 A | 2/1993 | Hughes |
| 5,204,354 A | 4/1993 | Chakravarty et al. |
| 5,264,439 A | 11/1993 | Greenlee et al. |
| 5,280,027 A | 1/1994 | Andrew et al. |
| 5,316,906 A | 5/1994 | Haughland et al. |
| 5,330,987 A | 7/1994 | Allen et al. |
| 5,342,944 A | 8/1994 | Mohan et al. |
| 5,401,766 A | 3/1995 | Geiger et al. |
| 5,430,148 A | 7/1995 | Webber et al. |
| 5,444,061 A | 8/1995 | Bisset et al. |
| 5,449,678 A | 9/1995 | Pines et al. |
| 5,470,878 A | 11/1995 | Michnick et al. |
| 5,492,915 A | 2/1996 | Dereu et al. |
| 5,561,133 A | 10/1996 | Bisset et al. |
| 5,574,057 A | 11/1996 | Ireland et al. |
| 5,707,992 A | 1/1998 | Webber et al. |
| 5,714,493 A | 2/1998 | Myers et al. |
| 5,747,498 A | 5/1998 | Schnur et al. |
| 5,753,664 A | 5/1998 | Aono et al. |
| 5,756,450 A | 5/1998 | Hahn et al. |
| 5,756,502 A | 5/1998 | Padia |
| 5,756,510 A | 5/1998 | Griffin et al. |
| 5,770,595 A | 6/1998 | Klein et al. |
| 5,773,476 A | 6/1998 | Chen et al. |
| 5,777,115 A | 7/1998 | Leigh et al. |
| 5,780,476 A | 7/1998 | Underiner |
| 5,783,577 A | 7/1998 | Houghten et al. |
| 5,789,427 A | 8/1998 | Chen et al. |
| 5,795,898 A | 8/1998 | Brown et al. |
| 5,801,181 A | 9/1998 | Michnick et al. |
| 5,801,182 A | 9/1998 | Klein et al. |
| 5,804,584 A | 9/1998 | Underiner et al. |
| 5,807,861 A | 9/1998 | Klein et al. |
| 5,807,862 A | 9/1998 | Klein et al. |
| 5,811,429 A | 9/1998 | Connell et al. |
| 5,817,662 A | 10/1998 | Klein et al. |
| 5,837,703 A | 11/1998 | Kumar et al. |
| 5,852,024 A | 12/1998 | Pines et al. |
| 5,859,018 A | 1/1999 | Brown et al. |
| 5,869,665 A | 2/1999 | Padia |
| 5,885,996 A | 3/1999 | Webber et al. |
| 5,891,879 A | 4/1999 | Nagler et al. |
| 5,892,114 A | 4/1999 | Goldmann et al. |
| 5,922,866 A | 7/1999 | Miyata et al. |
| 5,929,081 A | 7/1999 | Brown et al. |
| 5,939,421 A | 8/1999 | Palanki et al. |
| 5,948,775 A | 9/1999 | Koko et al. |
| 5,948,784 A | 9/1999 | Fujiwara et al. |
| 6,008,010 A | 12/1999 | Greenberger et al. |
| 6,136,812 A | 10/2000 | Chenard et al. |
| 6,156,758 A | 12/2000 | Kung et al. |
| 6,207,403 B1 | 3/2001 | Goldstein et al. |
| 6,214,879 B1 | 4/2001 | Abraham et al. |
| 6,245,768 B1 | 6/2001 | He et al. |
| 6,518,277 B1 | 2/2003 | Sadhu et al. |
| 6,545,004 B1 | 4/2003 | Finer et al. |
| 6,545,005 B1 | 4/2003 | Baxter et al. |
| 6,559,160 B1 | 5/2003 | Schall et al. |
| 6,562,831 B1 | 5/2003 | Finer et al. |
| 6,596,723 B1 | 7/2003 | Watkins et al. |
| 6,613,798 B1 | 9/2003 | Porter et al. |
| 6,627,755 B1 | 9/2003 | Chenard et al. |
| 6,630,479 B1 | 10/2003 | Finer et al. |
| 6,753,428 B2 | 6/2004 | Bergnes et al. |
| 6,794,379 B2 | 9/2004 | Medina et al. |
| 6,831,085 B1 | 12/2004 | Bergnes et al. |
| 7,038,048 B2 | 5/2006 | Lu et al. |
| 2001/0046997 A1 | 11/2001 | Abraham et al. |
| 2002/0032207 A1 | 3/2002 | Thompson et al. |
| 2002/0055519 A1 | 5/2002 | Thompson et al. |
| 2002/0165221 A1 | 11/2002 | Baxter et al. |
| 2002/0169159 A1 | 11/2002 | Medina et al. |
| 2002/0198326 A1 | 12/2002 | Aoyama et al. |
| 2003/0018038 A1 | 1/2003 | Thompson et al. |
| 2003/0055054 A1 | 3/2003 | Medina et al. |
| 2003/0091946 A1 | 5/2003 | Uchira et al. |
| 2003/0096813 A1 | 5/2003 | Cao et al. |
| 2003/0119834 A1 | 6/2003 | Bamdad |
| 2003/0119854 A1 | 6/2003 | Schall et al. |
| 2003/0130293 A1 | 7/2003 | Bamdad |
| 2003/0139398 A1 | 7/2003 | Hoekstra et al. |
| 2003/0139457 A1 | 7/2003 | Baxter et al. |
| 2003/0144350 A1 | 7/2003 | Stevenson et al. |
| 2003/0158188 A1 | 8/2003 | Lee et al. |
| 2003/0158198 A1 | 8/2003 | Lee et al. |
| 2003/0166933 A1 | 9/2003 | Bergnes et al. |
| 2003/0171387 A1 | 9/2003 | Sun et al. |
| 2003/0195211 A1 | 10/2003 | Sadhu et al. |
| 2003/0220338 A1 | 11/2003 | Watkins et al. |
| 2003/0220356 A1 | 11/2003 | Ibrahim et al. |
| 2004/0023996 A1 | 2/2004 | Finer et al. |
| 2004/0048853 A1 | 3/2004 | Bergnes |
| 2004/0067969 A1 | 4/2004 | Bergnes et al. |
| 2004/0077662 A1 | 4/2004 | Zhou et al. |
| 2004/0077667 A1 | 4/2004 | Matsuoka et al. |
| 2004/0077668 A1 | 4/2004 | Feng et al. |
| 2004/0082567 A1 | 4/2004 | McDonald et al. |
| 2004/0092561 A1 | 5/2004 | Ruckle et al. |
| 2004/0116438 A1 | 6/2004 | Lu et al. |
| 2004/0142949 A1 | 7/2004 | Bergnes et al. |
| 2004/0192913 A1 | 9/2004 | Bergnes et al. |
| 2004/0198724 A1 | 10/2004 | McNaughton-Smith et al. |
| 2004/0242596 A1 | 12/2004 | Kim et al. |
| 2004/0259826 A1 | 12/2004 | Fraley et al. |
| 2005/0059823 A1 | 3/2005 | McNaughton-Smith et al. |
| 2005/0148593 A1 | 7/2005 | Bergnes et al. |
| 2005/0152940 A1 | 7/2005 | Hezi-Yamit et al. |
| 2005/0209254 A1 | 9/2005 | Wang et al. |

FOREIGN PATENT DOCUMENTS

| | | |
|---|---|---|
| EP | 0 056 637 A1 | 7/1982 |
| EP | 0 286 813 A2 | 2/1988 |
| EP | 0 341 990 A3 | 11/1989 |
| EP | 0 341 990 B1 | 11/1989 |
| EP | 0 360 417 A2 | 3/1990 |
| EP | 0 360 417 A3 | 3/1990 |
| EP | 0 373 891 A2 | 6/1990 |
| EP | 0 431 945 A2 | 6/1991 |
| EP | 0 481 614 A1 | 4/1992 |
| EP | 0 509 643 A1 | 10/1992 |
| EP | 0 512 676 A1 | 11/1992 |
| EP | 0 534 706 A1 | 3/1993 |
| EP | 0 537 937 A2 | 4/1993 |
| EP | 0 884 310 A1 | 12/1998 |
| EP | 0 884 316 A1 | 12/1998 |
| EP | 0 884 319 A2 | 12/1998 |
| EP | 0 884 319 A3 | 12/1998 |
| EP | 0 900 568 A2 | 3/1999 |
| EP | 0 903 344 A1 | 3/1999 |
| EP | 1 072 952 A1 | 1/2000 |
| EP | 1 174 430 A1 | 1/2002 |
| GB | 2271111 A | 4/1994 |
| HU | 184797 | 10/1984 |
| JP | 62-135473 | 6/1987 |
| JP | 06049070 A2 | 2/1994 |
| JP | 06-148835 | 5/1994 |
| JP | 10/259176 | 9/1998 |
| WO | WO 91/12001 A1 | 8/1991 |
| WO | WO 93/11115 A2 | 6/1993 |
| WO | WO 93/19051 A1 | 9/1993 |

| | | |
|---|---|---|
| WO | WO 93/20055 A1 | 10/1993 |
| WO | WO 93/23404 A1 | 11/1993 |
| WO | WO 94/21259 A1 | 9/1994 |
| WO | WO 95/16682 A1 | 6/1995 |
| WO | WO 95/19169 A2 | 7/1995 |
| WO | WO 95/24379 A1 | 9/1995 |
| WO | WO 96/06616 A1 | 3/1996 |
| WO | WO 96/19224 A1 | 6/1996 |
| WO | WO 96/28430 A1 | 9/1996 |
| WO | WO 96/28444 A1 | 9/1996 |
| WO | WO 96/39403 A1 | 12/1996 |
| WO | WO 97/10221 A1 | 3/1997 |
| WO | WO 97/43276 A1 | 11/1997 |
| WO | WO 98/26664 A1 | 6/1998 |
| WO | WO 98/29410 A1 | 7/1998 |
| WO | WO 98/34613 A1 | 8/1998 |
| WO | WO 98/58947 A1 | 12/1998 |
| WO | WO 99/08501 A2 | 2/1999 |
| WO | WO 99/20298 A1 | 4/1999 |
| WO | WO 00/00491 A1 | 1/2000 |
| WO | WO 00/07017 A2 | 2/2000 |
| WO | WO 01/74344 A2 | 10/2000 |
| WO | WO 00/69827 A1 | 11/2000 |
| WO | WO 01/16114 A2 | 3/2001 |
| WO | WO 01/19800 A2 | 3/2001 |
| WO | WO 01/23364 A1 | 4/2001 |
| WO | WO 01/23365 A1 | 4/2001 |
| WO | WO 01/25235 A1 | 4/2001 |
| WO | WO 01/30768 A1 | 5/2001 |
| WO | WO 01/32171 A1 | 5/2001 |
| WO | WO 01/32634 A1 | 5/2001 |
| WO | WO 01/42216 A2 | 6/2001 |
| WO | WO 01/66519 A2 | 9/2001 |
| WO | WO 01/70737 A2 | 9/2001 |
| WO | WO 01/81346 A2 | 11/2001 |
| WO | WO 01/95884 A2 | 12/2001 |
| WO | WO 01/98278 A1 | 12/2001 |
| WO | WO 02/04444 A2 | 1/2002 |
| WO | WO 02/08224 A1 | 1/2002 |
| WO | WO 02/09713 A2 | 2/2002 |
| WO | WO 02/09713 A3 | 2/2002 |
| WO | WO 02/14319 A2 | 2/2002 |
| WO | WO 02/30462 A2 | 4/2002 |
| WO | WO 02/083143 A1 | 10/2002 |
| WO | WO 02/094790 A1 | 11/2002 |
| WO | WO 03/020279 A2 | 3/2003 |
| WO | WO 03/020280 A2 | 3/2003 |
| WO | WO 03/027234 A2 | 4/2003 |
| WO | WO 03/035076 A1 | 5/2003 |
| WO | WO 03/035077 A1 | 5/2003 |
| WO | WO 03/039460 A2 | 5/2003 |
| WO | WO 03/043961 A2 | 5/2003 |
| WO | WO 03/043995 A1 | 5/2003 |
| WO | WO 03/049527 A2 | 6/2003 |
| WO | WO 03/049678 A2 | 6/2003 |
| WO | WO 03/049679 A2 | 6/2003 |
| WO | WO 03/050064 A2 | 6/2003 |
| WO | WO 03/050122 A2 | 6/2003 |
| WO | WO 03/063800 A2 | 8/2003 |
| WO | WO 03/070701 A2 | 8/2003 |
| WO | WO 03/070701 A3 | 8/2003 |
| WO | WO 03/076418 A1 | 9/2003 |
| WO | WO 03/079973 A2 | 10/2003 |
| WO | WO 03/084544 A2 | 10/2003 |
| WO | WO 03/094839 A2 | 11/2003 |
| WO | WO 03/097053 A1 | 11/2003 |
| WO | WO 03/099211 A2 | 12/2003 |
| WO | WO 03/103575 A2 | 12/2003 |
| WO | WO 03/105855 A1 | 12/2003 |
| WO | WO 03/106417 A1 | 12/2003 |
| WO | WO 03/106426 A1 | 12/2003 |
| WO | WO 03/106435 A1 | 12/2003 |
| WO | WO 2004/004652 A2 | 1/2004 |
| WO | WO 2004/006916 A1 | 1/2004 |
| WO | WO 2004/009036 A2 | 1/2004 |
| WO | WO 2004/018058 A2 | 3/2004 |
| WO | WO 2004/020599 A2 | 3/2004 |
| WO | WO 2004/022554 A1 | 3/2004 |
| WO | WO 2004/034972 A2 | 4/2004 |
| WO | WO 2004/039774 A2 | 5/2004 |
| WO | WO 2004/064741 A2 | 8/2004 |
| WO | WO 2004/078758 | 9/2004 |

OTHER PUBLICATIONS

"Cytokinetics Announces the Initiation of an Additional Phase II Clinical Trial for Lead Cancer Drug Candidate," (Dec. 16, 2004).*

Garber, J. Nat. Cancer Inst., vol. 97, No. 12, Jun. 15, 2005.*

Vippagunta, et al., Advanced drug Delivery Reviews 48 (2001) 3-26.*

Chemcats Copyright 2000 ACS, 1998:596123 Chemcats, Maybridge, Apr. 3, 2000, DP 01489, "N2-(3-pyridylmethyl)-4-oxo-3,4-dihydroquinazoline-2-carboxamide," 190437-46-8, Chemical Library.

Q. Kozhevnikov et al. 4-Quinazolinones. II. 2-(Aminomethyl)-3-aryl-4-quinazolines. (Russian) Tr Perm Sel-Khoz Ints. 79: 66-72 (1971). *Chem Abstracts* 78: 390 (1973).

Gupta, C.M. et al. "Drugs acting on the central nervous system. Synthesis of substituted quinazolones and quinazolines and triazepino- and triazocinoquinazolones," *J. Med. Chem.* 11: 392-395 (1968).

Mayer et al., "Small Molecule Inhibitor of Mitotic Spindle Bipolarity Identified in a Phenotype-Based Screen," *Science*, 286: 971-974 (1999).

Tortora et al., "Oral Administration of a Novel Taxane, an Antisense Oligonucleotide Targeting Protein Kinase A, and the Epidermal Growth Factor Receptor Inhibitor Iressa Causes Cooperative Antitumor and Antiangiogenic Activity," *Clinical Cancer Research*, 7: 4156-4163 (2001).

Guo et al., "Overexpression of Bax Enhances Antitumor Activity of Chemotherapeutic Agents in Human Head and Neck Squamous Cell Carcinoma," *Clinical Cancer Research*, 6: 718-724 (2000).

Simone, "Oncology: Introduction," *Cecil Textbook of Medicine, 20th Edition*, 1: 1004-1010 (1996).

Farrell et al., "The role of ATP hydrolysis for kinesin processivity," PubMed Abstract only, *J Biol Chem*, 277(19): 17079-17087 (2002).

Yildiz et al., "Kinesin: walking, crawling or sliding along?" *TRENDS in Cell Biology*, 15(2): 112-120 (2005).

Office Action mailed Dec. 5, 2005, for U.S. Appl. No. 10/429,195, filed May 2, 2003.

Office Action mailed Dec. 6, 2005, for U.S. Appl. No. 10/644,244, filed Aug. 20, 2003.

Office Action mailed Dec. 20, 2005, for U.S. Appl. No. 10/893,929, filed Jul. 20, 2004.

Notice of Allowance from the U.S. Patent and Trademark Office for U.S. Appl. No. 10/444,283, dated Sep. 6, 2005, 25 pages.

Supplementary European Search Report for EP 03757286, dated Aug. 11, 2006, 4 pages.

Saari, W.S. et al. "Synthesis and evaluation of 2-pyridinone dervatives as HIV-1-specific reverse transcriptase inhibtors. 2. Analogues of 3-aminopyridin-2(1H)-one," *J. Med. Chem.* 35: 3792-3802 (1992).

Farghaly, A.M. et al. "Non-steroidal anti-inflammatory agents. III: Synthesis of pyrazole derivatives of 4(3H)-quinazolinones," *Alexandria J. Pharm. Sci.* 4(1): 52-56 (1990).

Dymek, W. et al. "2-Chloromethyl-6-methylquinazolone-4 and its transformations," *Dis. Pharm. Et Pharmacol.* 20(1): 29-34 (1968).

Pattanaik, J.M. et al. "Synthesis and fungicidal activity of 3-aryl-2-(4'-aryl thiazol-2'-ylaminomethyl) quinazol-4(3H)-ones," *Indian J. Chem.* 37B: 1304-1306 (1998).

Gupta, D.P.,e t al. "Thiazolidinones, azetidinones and formazans of quinazolinones," *Indian J. Chem.* 26B: 1197-1199 (1987).

Parasharya, P.M. et al. " 4 (3H)-Quinazolones. Part I: 2-Alkyl/arylaminomethyl-3-p-hydroxy/methoxyphenyl-4(3H)-quinazolones," J. Inst. Chemists (India) 64: 184-185 (1992).

Parasharya, P.M. et al. "4-(3H)-Quinazolones: 2-N-aryl/alkyl-amino-methyl/ethyl-3-p-hydroxyphenyl/p-anisyl/p-arylaminoacyloxyphenyl/p-N-arylcarbamoylmethoxyphenyl-4-(3H)-quinazolones," *J. Inst. Chemists* (India) 64: 238-241 (1992).

Matthews, N. et al. "Structure-activity relationships of phenothiazines in inhibiting lymphocyte motility as determined by a novel flow cytometric assay," *Biochem. Pharmcol.* 50(7): 1053-1061 (1995).

Debnath, A.K. "Structure-Based Identification of Small Molecule Antiviral Compounds Targeted to the gp41 Core Structure of the Human Immunodeficiency Virus Type 1," *J. Med. Chem.* 42 (17): 3203-3209 (1999).

Bocskei, Z. et al.. "Two Antithrombotic Quinazolone Derivatives." *Acta Crystallogr., Sect. C: Cryst. Struct. Commun.* C51(4): 723-726 (1995).

Szabó, M. et al. "Synthesis of Potential CCK Antagonist Quinazolone Derivatives," Chemical Abstracts, vol. 124, No. 13, Abstract No. 176002v (1996).

Ager et al. "Synthesis and Central Nervous System Activity of Quinazolones Related to 2-Methyl-3-(o-tolyl)-4(3H) quinazolone (Methaqualone)," *J. Med. Chem.* 20(3): 379-386 (1977).

Tiwari et al. "Synthesis and CNS Activity of 2-Aryl-3(3'-, 4'-Dihydroxyphenylethyl) 6-8-substituted-4 (3H)Quinazolinones," *Indian J. Pharm. Sci.* pp. 40-43 (1978).

Rao et al. "Synthesis and Biological Activities of Certain Derivatives of 3-Aryl-4(3H)-quinazolinones, Part-II," *J. Indian Chem. Soc.* LXII: 234-237 (1985).

Commercially available from ComGenex, Sep. 16, 1999.

Registry File Compounds from Published References, Maybridge Catalog, Apr. 3, 2000.

Singh et al. Chemical Abstracts, Vol. 92, Abstract No. 58712 (1980).

Spirkova et al., Chemical Abstracts, vol. 132, Abstract No. 35672 (1999).

Pandey et al. Chemical Abstracts, vol. 124, Abstract No. 331723 (1996).

Parasharya et al. Chemical Abstracts, vol. 121, Abstract No. 108675 (1994).

Saari et al. Chemical Abstracts, vol. 117, Abstract No. 191731 (1992).

Farghaly et al. Chemical Abstract, vol. 114, Abstract No. 122242 (1991).

El-Nasser Ossman et al. Chemical Abstracts, vol. 106, Abstract No. 207516 (1987).

Rao et al. Chemical Abstracts, vol. 105, Abstract No. 97416 (1986).

Gupta et al. Chemical Abstracts, vol. 69, Abstract No. 42637 (1968).

Kumar et al. Chemical Abstracts, vol. 102, Abstract No. 142800 (1985).

Chaurasia et al. Chemical Abstracts, vol. 96, Abstract No. 6681 (1982).

Tani et al. Chemical Abstracs, vol. 93, Abstract No. 26374 (1980).

Ager et al. Chemical Abstracts, vol. 86, Abstract No. 83505 (1977).

Kozhevnikov et al. Chemical Abstracts, vol. 78, Abstract No. 16128U (1971).

Bergman et al. "Synthesis of Chrysogine, a Metabolite of *Penicillium chrysogenum* and some related 2-substituted 4-(3H)-Quinazolinones," *Tetrahedron* 46: 1295-1310 (1990).

Hart et al. "Synthesis of (-)-Alantrypinone," *Tet. Lett.* 40: 5429-5432 (1999).

Hart et al. "Synthesis of *ent*-Alantrypinone" *J. Am. Chem. Soc.* 123: 5892-5899 (2001).

Mayer et al. "Solid phase synthesis of quinazolinones" *Tet. Lett.* 38(49):8445-8448 (1997).

Prashad et al. "Reaction of benzoyleneurea and isatoic anhydride with the Vilsmeier reagent" *Tet. Lett.* 38(8):1313-1316 (1997).

Villalgordo et al. "Solid-phase synthesis of 3H-quinazolin-4-ones based on an aza Wittig-mediated annulation strategy" *Synlett* 1405-1407 (1998).

Wuckelt et al. "Efficient synthesis of quinazolin-4-ones and axially chiral 2,2'-bis-quinazolin-4-ones by reaction of anthranilic acid derived nucleophiles with oxalic acid-bis(imidoyl)chlorides." *Synlett* 7:1100-1102 (1999).

Wang et al. "Total synthesis of the quinazolinone alkaloids (−)-Fumiquinazoline G and (−)-Fisclin B" *J. Org. Chem.* 6:2432-2433 (1998).

Padia et al. "Novel nonpeptide CCK-B antagonists: Design development of quinazolinone derivatives as potent, selective, and orally active CCK-B antagonists" *J. Med. Chem.* 41:1042-1049 (1998).

Singh et al. "4-Quinazolones—II Synthesis of some imidazo [1,5-a] quinazolones" *J. Indian Chem. Soc.* 46(1):21-25 (1969).

Badawy et al. "Chemistry of Quinazolines: Reinvestigation of the Action of Hydrazine on Thioxo Derivatives" *J. Heterocyclic Chem.* 22: 1535-1536 (1985).

Yu et al. "Synthesis and x-ray crystallographic analysis of quinazolinone cholecystokinin/gastrin receptor ligands" *J. Med. Chem.* 35:2534-2542 (1992).

Zaher et al. "Reactions of 2-p-anisyl-3(4H), 1-benzoxazin-4-one with ammonia, primary amines, hydrazine, phenylhydrazine & Grignard reagents" *Indian J. Chem.* 12:1212-1215 (1974).

Kulkarni et al. "Possible antifertility agents. Part-I. Synthesis of 2-(N,N-substituted-aminomethyl)-3-(2-pyridyl)-4(3H)-oxo-3,1-quinazolines" *J. Indian Chem.* LXI:720-721 (1984).

Majo et al. "Dimerization of substituted 2-aminobenzoic acids under Vilsmeier conditions: A novel route to the synthesis of 4-(3H)-quinazolinones" *Tet. Lett.* 37(28):5015-5018 (1996).

Rathman et al. "Functionalization of 2-methyl-3-o-tolyl-4(3H)-quinazolinone and related compounds through carbanion reactions at the 2-methyl group" *J. Org. Chem.* 45:2169-2176 (1980).

Padia et al. "Design and synthesis of novel nonpeptide CCK-B receptor antagonists" *Bioorg. Med. Chem. Lett.* 7(7):805-810 (1997).

Zentmyer et al. "The so-called acylanthranils (3,1,4-benzoxazones). I. Preparation; reactions with water, ammonia, and aniline; structure" *J. Organic Chemistry*, 14: 967-981 (1949).

Panday, V.K. "Possible Antiparkinsonian Compounds Part XI: Synthesis of 2-aryl/alkyl-3-[β-(3'-4'-dihydroxyphenyl) ethyl]-quinazolin (3H)-4-one and 2-aryl/alkyl-3-[(7'-(phenothiazinyl)-ethyl]-quinazolin/(3H)-4-one" *Acta Ciencia Indica* 4(3):230-235 (1978).

Tiwari et al. Chemical Abstracts, vol. 96, Abstract No. 14279p (1982).

Fadda et al. "Reactions of a heterocyclic β-enaminoester: Synthesis of pyranopyrimidines and pyrano[3', 2', ; 5,6]pyrimidino[2,3-c][1,4]benzoxazine ring system," *Indian J. Chemistry* 29B: 1020-1024 (1990).

Wagner "Synthesis and Biological Evaluation of Some Derivatives of Pyrido[3, 2-d]pyrimidine" *Acta Poloniae Pharmaceutica—Drug Research* 51(4-5): 359-363 (1994).

El-Sharief et al. "Oxidation of 3-aminoquinazolinones with lead tetraacetate. A novel synthesis of naphtho-fused azirino-pyrazolo and 1,4,5-oxadiazepino-quinazolinones" *J. Chem Research (S)*: 205-208 (2002).

Chenard et al. "Quinazolin-4-one α-Amino-3-hydroxy-5-methyl-4-isoxazolepropionic Acid (AMPA) Receptor Antagonists: Structure-Activity Relationship of the C-2 Side Chain Tether" *J. Med. Chem* 44:1710-1717 (2001).

Garg et al. "Synthesis and anti-implantation activity of α-(2-aryl-3-ethyl-4-oxo (3H) quinazolinyl)-α-(substituted styryl)-cyclohexanone thiosemicarbazones" *Biol. Mem.* 14(2):180-186 (1988).

Singh et al. "Synthesis and pharmacological screening of some 2-aryl-3-(phenyl-aryl-hydrazonyl)-quinazolin (3H) 4-ones" *Indian Drugs* 28(2):70-74 (1990).

Ahmad et al. "Monoamine oxidase Inhibitory Activity of 4 (3H)-Quinazolinones of Dopamine" *Indian J. of Pharm. Sci.* 126-127 (1979).

Tiwari et al. "Possible Antifertility Compounds Part III: Synthesis of 2-Hippuryl-3-Aryl-Quinazolinones" *J. Chem. Soc. Pak.* 3(4):215-217 (1981).

Pandey, V.K. "Antiparkinsonism and CNS Activities of 2-aryl alkyl-3-{β-(3'-4'-dihydroxyphenyl) Ethyl}-quinazolin (3H) 4-ones" *Biol. Mem.* 11(2):213-215 (1985).

Szábo et al. "Uj kinazolonszarmazekok szintezise es ciklizalasa [1,4]oxazepino- es [1,4]diazepino [3,4-b]kinazolokka" *Magyar Kemiai Folyoirat* 102(8):343-355 (1996) translated abstract.

Reddy et al. "A New Synthesis of 2-aryl-2H-Pyrazino[2,1-β]Quinazolin-3,6(1H,4H)-Diones" *Synthetic Communications* 21(2):173-181 (1991).

Szabö et al. "Potencialis CCK-antagonista kinazolon-szarmazekok szintezse" *Acta Pharm. Hungarica* 65:133-136 (1995) translated abstract.

Pandey et al. "Quinazolyl-thiazoles as CNS acting agents" *Acta Pharm.* 46:51-59 (1996).

Reddy et al. "4-Heteryl-β-lactams: A facile synthesis of 1-aryl-4-[isopropylideneanmino/methyl-4(3H)-oxoquinazolin-2-yl]azetidin-2-ones" *Indian J. of Chem.* 38B:40-44 (1999).

Reddy et al. "Bisazaheterocycles: Part VII—Synthesis of novel bisquinazolinonyl β-lactams" *Ind. J. of Chem.* 41B:1946-1949 (2002).

Gyimesi-Forrás et al. "Az AGP-alapu folyadek-kromatografias allofazis alkalmazasa kinazolon szarmazekok enantiomerjeinek elvalasztasaban" *Acta Pharma. Hungarica* 73:5-12 (2003) translated abstract.

Reddy et al. "Synthesis of 2-quinazolinonyl imidazolidinones" *Ind. J. of Chem.* 42B:393-396 (2003).

Gyimesi-Forrás et al. "Optical Resolution of a Series of Potential Cholecystokinin Antagonist 4(3H)-Quinazolone Derivatives by Chiral Liquid Chromatography on $\alpha_1$-Acid Glycoprotein Stationary Phase" *J. of Chromat. Sci.* 38:430-434 (2000).

Jiang et al. "A Salt bridge between an N-terminal Coiled Coil of gp14 and an Antiviral Agent Targeted to the gp41 Core Is Important for Anti-HIV-1 Activity" *Biochem. and Biophys. Res. Communications* 270:153-157 (2000).

Hughes et al. "Quinazoline Antifolate Thymidylate Synthase Inhibitors: Alkyl, Substituted Alkyl, and Aryl Substituents in the C2 Position" *J. Med. Chem.* 33:3060-3067 (1990).

Hassanein et al. "Sythesis of 2-substituted-10H-[1,2,4] triazino [6,1-b] quinazoline-10-ones and 8,13,14,16 tetrahydronaphtho [2',3',:3,4] [1,2,5] triazepino [7,1-b] quinazoline-8,13,16-triones with biological interest" *Al-Azhar Bull. Sci.* 8(2):417-434 (1997).

Szabó et al. "Nitrogen Bridgehead Compounds: Part 88 [1], Synthesis of 3H,7H-[1,4]Diazepino[3,4-b]quinazoline-3,7-diones" *J. Heterocyclic Chem.* 34(21):21-25 (1997).

Kokosi et al. "Nitrogen Bridgehead Compounds: Part 90, An Efficient Versatile Synthesis of 1-Methyl-2-substituted 1,2,3,4-Tetrahydro-6H-Pyrazino[2,1-b]Quinazoline-3,6-Diones" *Heterocycles* 48(9):1851-1866 (1998).

El-Maghraby et al. "Synthesis of Glycylamionthiazoles" *Ind. J. Chem.* 12:1058-1059 (1974).

Hassan et al. "Synthesis and antimicrobial activity of some new N-aminoacyl derivatives of 2-amino-4-phenylthiazole" *Acta Pharm.* 47:159-166 (1997).

West, "Solid State Chemistry and it's Applications," Wiley, New York, 1988, pp. 358 & 365.

Office Action mailed May 7, 2001, for U.S. Appl. No. 09/699,047, filed Oct. 24, 2000.

Office Action mailed Apr. 24, 2002, for U.S. Appl. No. 09/699,047, filed Oct. 24, 2000.

Office Action mailed Feb. 6, 2002, for U.S. Appl. No. 09/724,644, filed Nov. 28, 2000.

Office Action mailed Oct. 21, 2002, for U.S. Appl. No. 09/724,644, filed Nov. 28, 2000.

Office Action mailed Feb. 6, 2002, for U.S. Appl. No. 09/724,712, filed Nov. 28, 2000.

Office Action mailed Apr. 9, 2002, for U.S. Appl. No. 09/724,713, filed Nov. 28, 2000.

Office Action mailed Oct. 21, 2002, for U.S. Appl. No. 09/724,713, filed Nov. 28, 2000.

Office Action mailed Mar. 22, 2002, for U.S. Appl. No. 09/724,897, filed Nov. 28, 2000.

Office Action mailed Dec. 17, 2002, for U.S. Appl. No. 09/724,897, filed Nov. 28, 2000.

Office Action mailed Jul. 11, 2003, for U.S. Appl. No. 09/724,897, filed Nov. 28, 2000.

Office Action mailed May 12, 2004, for U.S. Appl. No. 09/724,897, filed Nov. 28, 2000.

Office Action mailed Jul. 26, 2002, for U.S. Appl. No. 09/724,941, filed Nov. 28, 2000.

Office Action mailed Jan. 13, 2003, for U.S. Appl. No. 09/724,941, filed Nov. 28, 2000.

Office Action mailed Jan. 7, 2004, for U.S. Appl. No. 09/724,941, filed Nov. 28, 2000.

Office Action mailed Jul. 3, 2002, for U.S. Appl. No. 09/724,778, filed Nov. 28, 2000.

Office Action mailed Dec. 27, 2002, for U.S. Appl. No. 09/724,778, filed Nov. 28, 2000.

Office Action mailed Aug. 8, 2003, for U.S. Appl. No. 09/724,778, filed Nov. 28, 2000.

Office Action mailed Dec. 29, 2003, for U.S. Appl. No. 09/724,778, filed Nov. 28, 2000.

Office Action mailed Mar. 30, 2004, for U.S. Appl. No. 09/724,778, filed Nov. 28, 2000.

Office Action mailed Jul. 25, 2004, for U.S. Appl. No. 09/724,778, filed Nov. 28, 2000.

International Search Report mailed Feb. 22, 2001, for PCT Application No. PCT/US00/29585, filed Oct. 26, 2000.

Written Opinion mailed Sep. 21, 2001, for PCT Application No. PCT/US00/29585, filed Oct. 26, 2000.

International Preliminary Examination Report mailed Jan. 17, 2002, for PCT Application No. PCT/US00/29585, filed Oct. 26, 2000.

Office Action mailed Aug. 8, 2003, for U.S. Appl. No. 10/300,967, filed Nov. 20, 2002.

International Search Report mailed Feb. 7, 2003, for PCT Application No. PCT/US02/37410, filed Nov. 20, 2002.

Written Opinion mailed Sep. 9, 2003, for PCT Application No. PCT/US02/37410, filed Nov. 20, 2002.

International Preliminary Examination Report mailed Aug. 11, 2004, for PCT Application No. PCT/US02/37410, filed Nov. 20, 2002.

International Search Report mailed Oct. 31, 2001, for PCT Application No. PCT/US01/13901, filed Apr. 27, 2001.

International Search Report mailed Oct. 17, 2003, for PCT Application No. PCT/US03/18778, filed Jun. 12, 2003.

Office Action mailed Oct. 18, 2004, for U.S. Appl. No. 10/462,002, filed Jun. 12, 2003.

Written Opinion mailed Mar. 2, 2004, for PCT Application No. PCT/US03/18778, filed Jun. 12, 2003.

International Preliminary Examination Report mailed Sep. 8, 2004, for PCT Application No. PCT/US03/18778, filed Jun. 12, 2003.

International Search Report and Written Opinion mailed Dec. 6, 2004, for PCT Application No. PCT/US04/01279, filed Jan. 20, 2004.

International Search Report mailed Aug. 29, 2003, for PCT Application No. PCT/US03/14787, filed May 9, 2003.

Written Opinion mailed Jun. 10, 2004, for PCT Application No. PCT/US03/14787, filed May 9, 2003.

International Preliminary Examination Report mailed Nov. 16, 2004, for PCT Application No. PCT/US03/14787, filed May 9, 2003.

International Search Report mailed Jul. 16, 2004, for PCT Application No. PCT/US03/13627, filed May 2, 2003.

Office Action mailed Nov. 2, 2004, for U.S. Appl. No. 10/366,828, filed Feb. 14, 2003.

International Search Report mailed Aug. 12, 2003, for PCT Application No. PCT/US03/04713, filed Feb. 14, 2003.

Written Opinion mailed Jun. 24, 2004, for PCT Application No. PCT/US03/04713, filed Feb. 14, 2003.

International Preliminary Examination Report mailed Dec. 8, 2004, for PCT Application No. PCT/US03/04713, filed Feb. 14, 2003.

International Search Report mailed Jul. 9, 2004, for PCT Application No. PCT/US03/23319, filed Jul. 23, 2003.

International Preliminary Examination Report mailed Sep. 30, 2004, for PCT Application No. PCT/US03/23319, filed Jul. 23, 2003.

International Search Report mailed May 20, 2004, for PCT Application No. PCT/US03/26093, filed Aug. 20, 2003.

International Preliminary Examination Report mailed Aug. 5, 2004, for PCT Application No. PCT/US03/26093, filed Aug. 20, 2003.

Office Action mailed Jan. 4, 2005, for U.S. Appl. No. 10/444,283, filed May 22, 2003.

International Search Report mailed Dec. 18, 2003, for PCT Application No. PCT/US03/16500, filed May 22, 2003.
International Preliminary Examination Report mailed Jun. 23, 2004, for PCT Application No. PCT/US03/16500, filed May 22, 2003.
Bergnes et al., "Compounds, Compositions, and Methods," U.S. Appl. No. 10/980,627, filed Nov. 2, 2004.
Bergnes et al., "Compounds, Compositions, and Methods," U.S. Appl. No. 10/982,195, filed Nov. 5, 2004.
Bergnes, "Compounds, Compositions, and Methods," U.S. Appl. No. 11/005,629, filed Dec. 7, 2004.
Written Opinion mailed Sep. 24, 2004, for PCT Application No. PCT/US02/41309, filed Dec. 20, 2002.
International Search Report mailed Oct. 12, 2004, for PCT Application No. PCT/US03/30788, filed Sep. 30, 2003.
Office Action mailed Feb. 7, 2005, for U.S. Appl. No. 10/435,069, filed May 8, 2005.
International Preliminary Examination Report mailed Jan. 28, 2005, for PCT Application No. PCT/US03/30788, filed Sep. 30, 2003.
Office Action mailed Apr. 27, 2005, for U.S. Appl. No. 10/429,195, filed May 2, 2003.
International Preliminary Examination Report mailed May 9, 2005, for PCT Application No. PCT/US03/13627, filed May 2, 2003.
International Search Report and Written Opinion mailed Apr. 28, 2005, for PCT Application No. PCT/US04/36253, filed Nov. 2, 2004.
International Search Report and Written Opinion mailed Jun. 14, 2005, for PCT Application No. PCT/US04/36853, filed Nov. 5, 2004.
Sauter et al., CAPLUS Abstract No. 87:84931 (1977).
Uchida et al., CAPLUS Abstract No. 81:152142 (1974).
Yamada et al., CAPLUS Abstract No. 134:252363 (2001).
Matsuoka et al., CAPLUS Abstract No. 133:150920 (2000).
Nugent et al., CAPLUS Abstract No. 123:143921 (1995).
De Melo et al., CAPLUS Abstract No. 117:143023 (1992).
Irikura et al., CAPLUS Abstract No. 105:42834 (1986).
Kyorin Pharmaceutical Co., Ltd., CAPLUS Abstract No. 103:87901 (1985).
Shuto et al., CAPLUS Abstract No. 90:72134 (1979).
Katagiri et al., CAPLUS Abstract No. 100:51536 (1984).
Hegrand et al., CAPLUS Abstract No. 80:95873 (1974).
Wilkop et al., CAPLUS Abstract No. 75:77191 (1971).
Office Action mailed Jun. 24, 2005, for U.S. Appl. No. 10/773,602, filed Feb. 6, 2004.
Sauter et al. "Methaqualon-analoge Benzothienopyrimidine" *Arch. Pharm.* 309 (11): 908-913 (1976).
Ratajczyk et al. "1,3-Dimethyl-1H-pyrazolo(4,3-d)pyrimidine-7(6H)-ones," *Chemical Abstracts* 84(24), Abstract No. 164835m (1976).
Ovcharova et al. "Syntheses in the Purine Series VII. Some Reactions of 2,6-dichloro-9-methylpurine" *J. General Chemistry* 34(10): 3290-3295 (1964).
Ovcharova et al. "Syntheses in a Series of Purine Derivatives: XVII. New derviatives of 1,7-dimethylhypoxanthine," *Pharmaceutical Chemistry Journal* 3:150-152 (1967).
Gadad et al. "Synthesis and Antihyperlipaemic Activity of Some 2-Aminomethyl-3-aryl-5,6,7,8-tetrahydrobenzo(b)/5,6-dimethylthieno(2,3-d)-pyrimidin-4-ones," *Arzneimittel-Forschung Drug Res.* vol. 46(II), No. 10: 981-985 (1996).
Manjunath et al. "Synthesis and Evaluation of 2-Chloromethyl-3-N-substituted Arylthieno(2,3-d)pyrimidin-4-ones and Derivatives for Central Nervous System Depressant Activity," *Arzneimittel-Forschung Drug Res.* vol. 47(II), No. 9: 1005-1008 (1997).
Sauter "Beiträge dur Chemie schwefelhaltiger Heterocyclen, 3. Mitt.: Ringschlußreaktionen zu N-substituierten 2-Aminomethyl-Derivaten des 4-Oxo-3,4,5,6,7,8-hexahydro-benzo-[*b*]thieno-[2,3-*d*]pyrimidins," *Monatshefte für Chemie* 99: 2100-2106 (1968).
Sauter et al. "Imidazo- und Diazino-Anellierungen an das [1]Benzothieno[2,3-d]pyrimidin-System," *Monatshefte für Chemie* 109: 53-61 (1978).
Sauter et al., "3-Amino-thieno- und -[1]benzothieno[2,3-d]pyrimidin-derivative," *Arch. Pharm* 309(11): 914-919 (1976).
Sauter et al. "Neue basich substituierte Pyrimidine und Benzothienopyrimidine," *Arch. Pharm* 310(4): 336-343 (1977).

Yoneda et al. "A new Synthesis of Substituted 8-Aminopurine Derivatives," *Bulletin of the Chemical Society of Japan*, 46(6): 1836-1839 (1973).
Sauter, "2-Alkyl-4-oxo-3,4,5,6,7,8-hexahydrobenzo[b]thieno[2,3-d]pyrimidines," *Chemical Abstracts* 72(17), Abstract No. 90509m (1970).
Temple, "Tieno[2,3-d]pyrimidine antiallergic agents," *Chemical Abstracts* 88(5), Abstract No. 37830p (1978).
Temple, "Antiallergenic Compounds," *Chemical Abstracts* 91(9), Abstract No. 74644p (1979).
Böhm et al., "Neue Pyrrolderivate," *Die Pharmazie* 45(4): 245-246 (1990).
Shishoo et al., "Synthesis and Pharmacological Study of Antihyperlipaemic Activity of 2-Substituted Thieno(2,3-d)pyrimidin-4(3H)-ones," *Arzneimittel-Forschung Drug Res.* vol. 40(I), No. 5:567-572 (1990).
Pech et al., "Neue Pyrrolderivate; Darstellung von Pyrimido-[4',5'-5,4]-pyrrol[3,2-f][1,4]thiazepinen," *Z. Chemie* 30(7): 249-251 (1990).
Shishoo et al., "Reaction of Nitriles Under ACidic Conditions. Part III. A Facile Synthesis of Thienopyrimidin-4(3*H*)-ones," *J. Heterocyclic Chemistry*, 21(2): 375-380 (1984).
Vaidya et al., "Studies in Benzofurans: Part XII-Synthesis & Reactions of 2-Chloromethyl-3,4-dihydro-4-oxobenzofuro[3,2-d]pyrimidine," *Indian Journal of Chemistry*, 20B: 780-783 (1981).
Venugopalan et al., "Synthesis of 6,7-Dimethoxypyrimidol[4,5-*b*]-indoles as Potential Antihypertensive Agents," *J. Heterocyclic Chem.*, 25(6): 1633-1639 (1988).
Barili, "A Facile 'One Pot' Synthesis of 2,9-Disubstituted 8-Azapurin-6-ones (3,5-disubstituted 7-Hydroxy-3H-1,2,3-triazolo[4,5-d]pyrimidines)," *J. Heterocyclic Chem.*, 22(6): 1607-1609 (1985).
Matsuda et al., "Conversion of Guanosine into 2-Aminomethylinosine (2-Homoguanosine)," *Chem. Pharm. Bull.*, 32(5): 2048-2051 (1984).
Hocek et al, "A Facile Synthesis of 2-(Aminomethyl)purines," *Synthesis*, 12: 1401-1402 (1994).
Poreba et al., Synthesis and Preliminary Pharmacological Assessment of Derivatives of Isoxazolo[4,3-d]pyrimidine. II. *Acta Poloniae Pharmaceutics-Drug Research*, 51(4-5): 355-358 (1994).
Hocek et al., "Synthesis of Acyclic Nucleotide Analogues Dervied from 2-(Aminomethyl)adenine and 2-(Aminomethyl)hypoxanthine," *Collect. Czech. Chem. Commun.* 60: 875-882 (1995).
Atalla et al., "Synthesis and Reactions of 2-Chloromethyl-13-(2-furyl)-3,4,11,12-tetrahydro-4-oxopyrimido[4'-5':4,5]thieno[2,3-b]-benzo[h]quinoline," *Phosphorus, Sulfur, and Silicon*, 101: 83-90 (1995).
Biagi et al., "Xanthine Oxidase (XO): Synthesis of 4(5)-Carboxyamido-5(4)-(α-aminoalkanoyl)amino-1,2,3-triazoles and Their Cyclization to 8-Azahypoxanthines. Evaluation for Inhibition of XO," *Il Farmaco* 51(4): 301-303 (1996).
Crespo et al., "Design, Synthesis, and Biological Activities of New Thieno[3,2-d]pyrimidines as Selective Type 4 Phosphodiesterase Inhibitors," *J. Med. Chem.* 41: 4021-4035 (1998).
Moustafa, "Synthesis and Reactions of New Triazino Thiadiazino and Pyrimido Thieno[2,3-b]-quinoxaline," *Phosphorus, Sulfur, and Silicon*, 131: 49-57 (1997).
Merino et al., "Synthesis and anti-HIV-1 activities of new pyrimido[5,4-b]indoles," *Il Farmaco*, 54: 255-264 (1999).
Hosni et al., "Thienopyrimidines III. Synthesis of Novel Substituted Thieno[2,3-d]pyrimidinone Derivatives and Their Condensed Products with Molluscicidal and Larvicidal Activities," *J. Chem. Res. Miniprint*, 11: 2775-2794 (1999).
Shishoo et al., "Design, synthesis and antihistaminic ($H_1$) activity of some condensed 3-aminopyrimidin-4(3H)-ones," *Eur. J. Med. Chem.*, 35: 351-358 (2000).
Modica et al., "Design, synthesis and binding properties of novel and selective 5-$HT_3$ and 5-$HT_4$ receptor ligands," *Eur. J. Med. Chem.*, 35: 1065-1079 (2000).
Office Action mailed Jul. 6, 2005, for U.S. Appl. No. 10/982,195, filed Nov. 5, 2004.

Gavezzotti "Are Crystal Structures Predictable" *Acc. Chem. Res.* 27:309-314 (1994).

Wolff (ed.) Burger's Medicinal Chemistry and Drug Discovery, 5th Edition vol. 1: Principles and Practice, John Wiley & Sons, New York, pp. 975-977 (1995).

Banker et al. (eds.) Modern Pharmaceutics Third Edition, Revised and Expanded, Marcel Dekker, Inc., New York, pp. 451 & 596 (1996).

Coleman et al. "Inhibitors of the mitotic kinesin spindle protein" *Expert Opin. Ther. Patents* 14(12):1659-1667 (2004).

Li et al. "Discovery and development of antimitotic agents that inhibit tubulin polymerisation for the treatment of cancer" *Expert Opin. Ther. Patents* 12(11): 1663-1702 (2002).

Malik et al., "Compositions, Devices and Methods for Treating Cardiovascular Disease," U.S. Appl. No. 11/147,406, filed Jun. 7, 2005.

International Search Report and Written Opinion mailed Oct. 21, 2005, for PCT Application No. PCT/US05/19791, filed Jun. 7, 2005.

Franco et al., "Functional association of retinoic acid and *hedgehog* signaling in *Xenopus* primary neurogenesis," *Development*, 126: 4257-4265 (1999).

Gaffield et al., "A Looking Glass Perspective: Thalidomide and Cyclopamine," *Cellular and Molecular Biology*, 45(5):579-588 (1999).

Ghorab, "Synthesis of Some New Thiadiazole, Selena, Triazine, Thiazole and Cyanopyridine Derivatives with Assay for Their Antitumor Activity," *Phosphorus, Sulfur, and Silicon*, 112: 7-17 (1996).

Gailani et al., "The role of the human homologue of *Drosophilia* patched in sporadic basal cell carcinomas," *Nature Genetics*, 14: 78-81 (1996).

Ghorab et al., "Synthesis and effect of some new [1,2,4]triazolo[4,3-a]quinazolin-5(4H)-ones and related compounds on Ehrlich Ascites Carcinoma cells," *Acta Pharm.*, 49: 1-10 (1999).

Jiang et al., "Synthesis and Biological Evaluation of 2-Styrylquinazolin-4(3H)-ones, a New Class of Antimitotic Anticancer Agents Which Inhibit Tubulin Polymerization," *J. Med. Chem.*, 33: 1721-1728 (1990).

Smith et al., "Effects of Gastrin, Proglumide, and Somatostatin on Growth of Human Colon Cancer," *Gastroenterology*, 95: 1541-1548 (1988).

"Signal Transduction," from the *Dictionary of Biology*, Penguin Books, Ninth Edition reprinted with minor revisions, pp. 574-575 (1995).

"Hyper-," from *The British Medical Dictionary*, Caxton, p. 706 (circa 1961).

"Inhibit," from *The British Medical Dictionary*, Caxton, p. 747 (circa 1961).

Ghosh, "Quinazolines. Part I.," *J. Indian Chemical Society*, XIV: 411-413 (1937).

Office Action mailed Jan. 26, 2006, for U.S. Appl. No. 10/982,195, filed Nov. 5, 2004.

Office Action mailed Sep. 11, 2006, for U.S. Appl. No. 10/982,195, filed Nov. 5, 2004.

Office Action mailed Jan. 23, 2007, for U.S. Appl. No. 10/982,195, filed Nov. 5, 2004.

\* cited by examiner

MODULATION OF KSP KINESIN ACTIVITY WITH HETEROCYCLIC-FUSED PYRIMIDINONE DERIVATIVES

CROSS-REFERENCE TO RELATED APPLICATIONS

This application is a continuation of U.S. patent application Ser. No. 10/444,283 filed on May 22, 2003 now U.S. Pat. No. 7,038,048, which claims the benefit of U.S. Provisional Patent Application Ser. No. 60/382,737, filed May 23, 2002. Each of these applications is incorporated herein by reference in their entirety for all purposes.

FIELD OF THE INVENTION

This invention relates to heterocyclic-fused pyrimidinone derivatives that are inhibitors of the mitotic kinesin KSP and are useful in the treatment of cellular proliferative diseases, for example cancer, hyperplasias, restenosis, cardiac hypertrophy, immune disorders and inflammation.

BACKGROUND OF THE INVENTION

The mitotic spindle is responsible for distribution of replicate copies of the genome to each of the two daughter cells that result from cell division. Disruption of the mitotic spindle can inhibit cell division, and induce cell death. Microtubules are the primary structural element of the mitotic spindle; they are the site of action of certain existing therapeutic agents used to treat cancer, such as taxanes and vinca alkaloids. Microtubules, however, exist as elements in other types of cellular structures (including tracks for intracellular transport in nerve processes). The therapeutic targeting of microtubules can, therefore, modulate processes in addition to cellular proliferation, leading to side effects that limit the usefulness of such drugs.

Improvement in the specificity of agents used to treat cancer is of considerable interest because of the therapeutic benefits that would be realized if the side effects associated with the administration of these agents could be reduced. Dramatic improvements in the treatment of cancer have been associated with identification of therapeutic agents acting through novel mechanisms. Examples of this include not only the taxanes, but also the camptothecin class of topoisomerase I inhibitors.

One novel anti-proliferative mechanism entails selective inhibition of mitotic kinesins, enzymes that are essential for assembly and function of the mitotic spindle, but are not generally part of other microtubule structures, such as in nerve processes. See, e.g., Guidebook to the Cytoskeletal and Motor Proteins, Kreis and Vale, Eds., pp. 389-394 (Oxford University Press 1999). Mitotic kinesins play essential roles during all phases of mitosis. These enzymes are "molecular motors" that transform energy released by hydrolysis of ATP into mechanical force that drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death. Mitotic kinesins are attractive targets for the discovery and development of novel anti-mitotic chemotherapeutics.

Among the mitotic kinesins that have been identified is KSP. KSP belongs to an evolutionarily conserved kinesin subfamily of plus end-directed microtubule motors that assemble into bipolar homotetramers consisting of antiparallel homodimers. During mitosis, KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described [Blangy, et al., Cell, 83:1159-69 (1995); Whitehead, et al., Arthritis Rheum., 39:1635-42 (1996); Galgio et al., J. Cell Biol., 135:339-414 (1996); Blangy, et al., J. Biol. Chem., 272:19418-24 (1997); Blangy, et al., Cell Motil. Cytoskeleton, 40:174-82 (1998); Whitehead and Rattner, J. Cell Sci., 111:2551-61 (1998); Kaiser, et al., JBC 274:18925-31 (1999); GenBank accession numbers: X85137, NM004523 and U37426], and a fragment of the KSP gene (TRIP5) has been described [Lee, et al., Mol. Endocrinol., 9:243-54 (1995); GenBank accession number L40372]. *Xenopus* KSP homologs (Eg5), as well as *Drosophila* KLP61 F/KRP1 30 have been reported.

Recently, certain substituted quinazolinones have been described as inhibitors of mitotic kinesins for the treatment of cellular proliferative diseases (WO 01/30768 and WO 01/98278). It is an object of the present invention to provide novel inhibitors of mitotic kinesins such as KSP (particularly human KSP).

SUMMARY OF THE INVENTION

The present invention provides compounds, compositions and methods useful in the inhibition of mitotic kinesins, particularly KSP (more particularly human KSP). The compounds can be used to treat cellular proliferative diseases and include certain heterocyclic-fused pyrimidinone derivatives such as: pyrido[α,β-γ]pyrimidin-δ-ones, pyrimido[α,β-γ]pyrimidin-δ-ones, pyrimido[α,β-γ]pyridazin-δ-ones, and pteridin-4-ones.

In one aspect, the invention relates to one or more compounds selected from the group represented by Formula I:

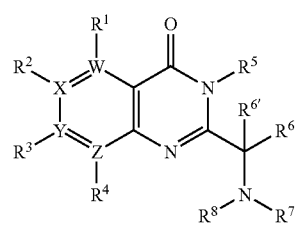

Formula I where:
W, X, Y and Z are independently —N═ or —C═, provided that at least one but no more than two of W, X, Y and Z are —N═;

$R^1$, $R^2$, $R^3$ and $R^4$ are independently hydrogen, hydroxy, optionally substituted alkyl, optionally substituted alkoxy, halogen or cyano, provided that $R^1$, $R^2$, $R^3$ or $R^4$ is absent where W, X, Y or Z, respectively, is —N=;

$R^5$ is optionally substituted alkyl or optionally substituted aryl;

$R^6$ and $R^{6'}$ are independently hydrogen, optionally substituted alkyl or optionally substituted aryl, or $R^6$ taken together with $R^{6'}$ is optionally substituted cycloalkyl or optionally substituted heterocycloalkyl having 5 to 7 ring atoms;

$R^7$ is optionally substituted alkyl or optionally substituted aryl; and $R^8$ is hydrogen, —C(O)—$R^9$, —S(O)$_2$—$R^9$, —CH$_2$—$R^9$, —C(O)—O—$R^9$, —C(O)—NH—$R^9$ or —S(O)$_2$—NH—$R^9$, in which:

$R^9$ is hydrogen, optionally substituted alkyl, optionally substituted aryl or optionally substituted heteroaryl;

or $R^7$ taken together with $R^8$ is optionally substituted imidazolyl or optionally substituted imidazolinyl, including single stereoisomers, mixtures of stereoisomers, and the pharmaceutically acceptable salts, solvates, and solvates of pharmaceutically acceptable salts thereof. Compounds of the invention are useful as active agents in the practice of the methods of treatment and in manufacture of compositions including the pharmaceutical formulations of the invention, and may also be useful as intermediates in the synthesis of such active agents.

In one of its particular aspects, the present invention pertains to compounds, methods and compositions employing a compound represented by Formula I where $R^5$ is other than optionally substituted phenyl when $R^6$ is methyl, optionally having one or more of the following:

X, Y or Z is —N=, or W and Z are —N=;

$R^1$, $R^2$, $R^3$ and $R^4$ are independently hydrogen, halo (particularly chloro and fluoro), lower alkyl (particularly methyl), substituted lower alkyl, lower alkoxy (particularly methoxy), cyano or absent; more particularly three of $R^1$, $R^2$, $R^3$ and $R^4$ are hydrogen, or two of $R^1$, $R^2$, $R^3$ and $R^4$ are hydrogen and a third is halo, methoxy or cyano, and the fourth is absent;

$R^5$ is optionally substituted aralkyl (particularly benzyl or substituted benzyl; more particularly benzyl);

$R^6$ is lower alkyl (particularly ethyl, i-propyl, c-propyl or t-butyl);

$R^{6'}$ is hydrogen;

$R^7$ is substituted alkyl (particularly primary-amino-substituted lower alkyl, secondary-amino-substituted lower alkyl or tertiary-amino-substituted lower alkyl); more particularly 3-amino-propyl; and/or $R^8$ is —C(O)—$R^9$, in which $R^9$ is optionally substituted alkyl (particularly lower alkyl, haloalkyl, and lower alkoxyalkyl), optionally substituted aryl (particularly phenyl, lower alkyl-, lower alkoxy-, and/or halo-substituted phenyl), optionally substituted aralkyl (particularly optionally substituted benzyl and phenylvinyl), aryloxyalkyl (particularly phenoxy lower alkyl), optionally substituted heteroaryl, optionally substituted heteroaralkyl or optionally substituted heteroaryloxyalkyl; more particularly where $R^9$ is methoxy-methyl or p-tolyl;

or $R^8$ is —C(O)—O$R^9$, in which $R^9$ is: optionally substituted aryl (particularly phenyl, lower alkyl-, lower alkoxy-, and/or halo-substituted phenyl) or optionally substituted heteroaryl.

In another of its particular aspects, the present invention pertains to compounds, methods and compositions employing a compound represented by Formula I where $R^5$ is other than optionally substituted phenyl when $R^6$ is methyl, optionally having one or more of the following:

$R^8$ is —S(O)$_2$—$R^9$, in which $R^9$ is: $C_1$-$C_{13}$ alkyl; heteroaryl; naphthyl; or phenyl optionally substituted with halo, lower alkyl, lower alkoxy, nitro, methylenedioxy, phenyl or trifluoromethyl; or $R^8$ is —CH$_2$—$R^9$, in which $R^9$ is: $C_1$-$C_{13}$ alkyl; substituted lower alkyl; benzyl; heterocyclyl; naphthyl; or phenyl optionally substituted with halo, lower alkyl, lower alkoxy, nitro, methylenedioxy, phenyl or trifluoromethyl; or $R^7$ taken together with $R^8$ is 2-(optionally substituted)-4,4-(optionally di-substituted)-4,5-dihydro-imidazol-1-yl, 2-(optionally substituted phenyl)-imidazol-1-yl, or 4-(optionally substituted alkyl)-2-(optionally substituted aryl)-imidazol-1-yl optionally having one or more of the following:

X, Y or Z is —N=;

$R^1$, $R^2$, $R^3$ and $R^4$ are independently hydrogen, chloro, fluoro, lower alkyl substituted lower alkyl, methoxy, cyano or absent;

$R^5$ is benzyl or substituted benzyl;

$R^6$ is ethyl, i-propyl, c-propyl or t-butyl; and/or $R^7$ is a primary-amino-substituted lower alkyl, secondary-amino-substituted lower alkyl or tertiary-amino-substituted lower alkyl;

and particularly where:

$R^9$ is heterocyclyl; naphthyl; or phenyl substituted with halo, lower alkyl, lower alkoxy, nitro, methylenedioxy, phenyl or trifluoromethyl; or $R^7$ taken together with $R^8$ is 2-(4-methylphenyl)-4,5-dihydro-imidazol-1-yl, 2-(3-fluoro-, 4-methylphenyl)-4,5-dihydro-imidazol-1-yl, 2-(4-methylphenyl)-4,4-dimethyl-4,5-dihydro-imidazol-1-yl, 2-(3-fluoro-, 4-methylphenyl)-4,4-dimethyl-4,5-dihydro-imidazol-1-yl, 2-phenyl-imidazol-1-yl, 2-p-toluoyl-imidazol-1-yl, 2-(4-fluorophenyl)-imidazol-1-yl, 2-(4-chlorophenyl)-imidazol-1-yl, 2-(3-fluoro-4-methylphenyl)-imidazol-1-yl, 4-(2-amino-ethyl)-2-phenyl-imidazol-1-yl, 4-(2-amino-ethyl)-2-p-tolyl-imidazol-1-yl, 4-(2-amino-ethyl)-2-(4-fluoro-phenyl)-imidazol-1-yl, 4-(2-amino-ethyl)-2-(4-chloro-phenyl)-imidazol-1-yl, 4-(2-amino-ethyl)-2-(3-fluoro-4-methyl-phenyl)-imidazol-1-yl, 4-(aminomethyl)-2-phenyl-imidazol-1-yl, 4-(aminomethyl)-2-p-tolyl-imidazol-1-yl, 4-(aminomethyl)-2-(4-fluoro-phenyl)-imidazol-1-yl, 4-(aminomethyl)-2-(4-chloro-phenyl)-imidazol-1-yl, or 4-(aminomethyl)-2-(3-fluoro-4-methyl-phenyl)-imidazol-1-yl.

In still another of its particular aspects, the present invention pertains to compounds, methods and compositions employing a compound represented by Formula I where $R^6$ and $R^{6'}$ are different and the stereogenic center to which $R^6$ is attached is of the (R)-configuration.

In one aspect, the invention relates to methods for treating cellular proliferative diseases, for treating disorders that can be treated by modulating KSP kinesin activity, and for inhibiting KSP kinesin by the administration of a therapeutically effective amount of a compound of Formula I or a pharmaceutically acceptable salt or solvate thereof. Diseases and disorders that respond to therapy with compounds of the invention include cancer, hyperplasia, restenosis, cardiac hypertrophy, immune disorders, inflammation and the like.

In another aspect of the invention, the composition is a pharmaceutical formulation containing a therapeutically effective amount of a compound of Formula I or a pharmaceutically acceptable salt or solvate thereof and at least one pharmaceutically acceptable excipient.

Yet another aspect of the invention relates to a kit having a compound, salt or solvate of Formula I and a package insert or other labeling including directions treating a cellular proliferative disease by administering a KSP kinesin inhibitory amount of the compound, salt or solvate.

In an additional aspect, the present invention provides methods of screening for compounds that will bind to a KSP kinesin, for example compounds that will displace or compete with the binding of the compounds of the invention. The methods entail combining a labeled compound of the invention, a KSP kinesin, and at least one candidate agent and determining the binding of the candidate agent to the KSP kinesin.

In a further aspect, the invention provides methods of screening for modulators of KSP kinesin activity. The methods entail combining a compound of the invention, a KSP kinesin, and at least one candidate agent and determining the effect of the candidate agent on the KSP kinesin activity.

DETAILED DESCRIPTION OF THE INVENTION

The present invention provides compounds, compositions and methods useful in the inhibition of mitotic kinesins, particularly KSP (more particularly human KSP). The compounds can be used to treat cellular proliferative diseases and include certain heterocyclic-fused pyrimidinone derivatives such as: pyrido[α,β-γ]pyrimidin-δ-ones, pyrimido[α,β-γ]pyrimidin-δ-ones, pyrimido[α,β-γ]pyridazin-δ-ones, and pteridin-4-ones. The invention further relates to pharmaceutical formulations comprising compounds of the invention, and methods of treatment employing such compounds or compositions.

Definitions

As used in the present specification, the following words and phrases are generally intended to have the meanings as set forth below, except to the extent that the context in which they are used indicates otherwise. The following abbreviations and terms have the indicated meanings throughout:

Ac=acetyl
Boc=t-butyloxy carbonyl
Bu=butyl
c-=cyclo
CBZ=carbobenzoxy=benzyloxycarbonyl
DCM=dichloromethane=methylene chloride=$CH_2Cl_2$
DCE=dichloroethane
DIEA=N,N-diisopropylethylamine
DMF=N,N-dimethylformamide
DMSO=dimethyl sulfoxide
Et=ethyl
GC=gas chromatography
Me=methyl
mesyl=methanesulfonyl
rt=room temperature
sat'd=saturated
S-=secondary
t-=tertiary
TFA=trifluoroacetic acid
THF=tetrahydrofuran The term "optional" or "optionally" means that the subsequently described event or circumstance may or may not occur, and that the description includes instances where said event or circumstance occurs and instances in which it does not. For example, "optionally substituted alkyl" includes "alkyl" and "substituted alkyl," as defined below. It will be understood by those skilled in the art with respect to any group containing one or more substituents that such groups are not intended to introduce any substitution or substitution patterns that are sterically impractical, synthetically non-feasible and/or inherently unstable.

"Alkyl" is intended to include linear, branched, or cyclic aliphatic hydrocarbon structures and combinations thereof, which structures may be saturated or unsaturated (particularly having up to 20 carbon atoms, more particularly up to $C_{13}$). Lower alkyl refers to alkyl groups of from 1 to 5 (particularly 1 to 4) carbon atoms. Examples of lower alkyl groups include methyl, ethyl, propyl, isopropyl, butyl, s- and t-butyl and the like. Cycloalkyl is a subset of alkyl and includes cyclic aliphatic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like. Alkylene, alkenylene and alkynylene are other subsets of alkyl, referring to the same residues as alkyl, but having two points of attachment. Examples of alkylene include ethylene (—$CH_2CH_2$—), ethenylene (—CH=CH—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl residue having a specific number of carbons is named, all geometric isomers of that residue having the specified number of carbons are meant to be included; thus, for example, "butyl" is meant to include n-butyl, sec-butyl, isobutyl and t-butyl; "propyl" includes n-propyl and isopropyl.

The term "alkoxy" or "alkoxyl" refers to the group —O-alkyl, particularly including from 1 to 8 carbon atoms in a straight, branched or cyclic configuration, or combinations thereof, attached to the parent structure through an oxygen. Examples include methoxy, ethoxy, propoxy, isopropoxy, cyclopropyloxy, cyclohexyloxy and the like. Lower-alkoxy refers to groups containing one to five carbons.

The term "substituted alkoxy" refers to the group —O-(substituted alkyl). One particular substituted alkoxy group is "polyalkoxy" or —O-(optionally substituted alkylene)-(optionally substituted alkoxy), and includes groups such as —$OCH_2CH_2OCH_3$, and glycol ethers such as polyethyleneglycol and —$O(CH_2CH_2O)_xCH_3$, where x is an integer of about 2-20, particularly about 2-10, and more particularly about 2-5. Another particular substituted alkoxy group is hydroxyalkoxy or —$OCH_2(CH_2)_yOH$, where y is an integer of about 1-10, particularly about 1-4.

"Acyl" refers to groups of from 1 to 8 carbon atoms in a straight, branched or cyclic configuration, or combinations thereof, or to a hydrogen atom attached to the parent structure through a carbonyl functionality. Such groups may be saturated or unsaturated, and aliphatic or aromatic. One or more carbons in the acyl residue may be replaced by nitrogen, oxygen or sulfur as long as the point of attachment to the parent remains at the carbonyl. Examples include formyl, acetyl, benzoyl, propionyl, isobutyryl, t-butoxycarbonyl, benzyloxycarbonyl, aminocarbonyl, and the like.

Lower-acyl refers to an acyl group containing one to five carbons. "Substituted acyl" refers to an acyl group where one or more of the hydrogens otherwise attached to a carbon, nitrogen or sulfur atom is substituted, the point of attachment to the parent moiety remaining at the carbonyl.

The term "acyloxy" refers to the group —O-acyl. "Substituted acyloxy" refers to the group —O-substituted acyl.

The term "amidino" refers to the group —C(=NH)—NH$_2$. The term "substituted amidino" refers to the formula —C(=NR)—NRR in which each R is independently selected from the group: hydrogen, optionally substituted alkyl, optionally substituted alkoxy, optionally substituted aminocarbonyl, optionally substituted aryl, optionally substituted heteroaryl, optionally substituted heterocyclyl, acyl, alkoxycarbonyl, sulfanyl, sulfinyl and sulfonyl, provided that at least one R is not hydrogen.

The term "amino" refers to the group —NH$_2$. The term "substituted amino" refers to the group —NHR or —NRR where each R is independently selected from the group: optionally substituted acyl, optionally substituted alkyl, optionally substituted alkoxy, optionally substituted amino, optionally substituted aryl, optionally substituted heteroaryl, optionally substituted heterocyclyl, sulfanyl, sulfinyl and sulfonyl, e.g., methylamino, dimethylamino, diethylamino, methylsulfonylamino, furanyl-oxy-sulfonamino, guanidino.

"Aryl" and "heteroaryl" mean a 5- or 6-membered aromatic ring or heteroaromatic ring containing 1-4 heteroatoms selected from O, N, or S; a bicyclic 9- or 10-membered aromatic ring system or heteroaromatic ring system containing 1-4 (or more) heteroatoms selected from O, N, or S; or a tricyclic 13- or 14-membered aromatic ring system or heteroaromatic ring system containing 1-4 (or more) heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole; particularly imidazole and imidazoline.

"Aralkyl" refers to a residue in which an aryl moiety is attached to the parent structure via an alkyl residue. Examples include benzyl, phenethyl, phenylvinyl, phenylallyl and the like. "Heteroaralkyl" refers to a residue in which a heteroaryl moiety is attached to the parent structure via an alkyl residue. Examples include furanylmethyl, pyridinylmethyl, pyrimidinylethyl and the like.

The term "aryloxy" refers to the group —O-aryl. Similarly, "aralkoxy" and "heteroaralkoxy" refer, respectively, to an aryl or heteroaryl moiety attached to the parent structure via an alkoxy residue.

"Halogen" or "halo" refers to fluorine, chlorine, bromine or iodine (particularly fluorine, chlorine and bromine). Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heterocycle" or "heterocyclyl" means a cycloalkyl or aryl residue in which one to four of the carbons is replaced by a heteroatom such as oxygen, nitrogen or sulfur (i.e., encompassing heterocycloalkyl and heteroaryl). Examples of heterocyclyl residues that fall within the scope of the invention include imidazolyl, imidazolinyl, pyrrolidinyl, pyrazolyl, pyrrolyl, indolyl, quinolinyl, isoquinolinyl, tetrahydroisoquinolinyl, benzofuranyl, benzodioxanyl, benzodioxolyl (commonly referred to as methylenedioxyphenyl, when occurring as a substituent), tetrazolyl, morpholinyl, thiazolyl, pyridinyl, pyridazinyl, pyrimidinyl, thiophenyl, furanyl, oxazolyl, oxazolinyl, isoxazolyl, dioxanyl, tetrahydrofuranyl and the like. "N-heterocyclyl" refers to a nitrogen-containing heterocycle as a substituent residue. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

The terms "heteroaryloxy" and "heterocyclooxy" refer, respectively to the groups —O-heteroaryl and —O-heterocyclyl.

The term "solvate" refers to a compound (e.g., a compound of Formula I or a pharmaceutically acceptable salt thereof) in physical association with one or more molecules of a pharmaceutically acceptable solvent. It will be understood that phrases such as "a compound of Formula I or a pharmaceutically acceptable salt or solvate thereof" are intended to encompass the compound of Formula I, a pharmaceutically acceptable salt of the compound, a solvate of the compound and a solvate of a pharmaceutically acceptable salt of the compound.

"Substituted-" e.g., as used with regard to acyl, alkyl, aryl, heteroaryl and heterocyclyl refers to an acyl, alkyl, aryl, heteroaryl or heterocyclyl moiety wherein one or more (up to about 5, particularly up to about 3) hydrogen atoms are replaced by a substituent independently selected from the group: optionally substituted acyl (e.g., aminocarbonyl and alkoxycarbonyl or "esters"), optionally substituted acyloxy (e.g., acid esters, carbamic acid esters, carbonic acid esters, and thiocarbonic acid esters), optionally substituted alkyl (e.g., fluoroalkyl), optionally substituted alkoxy (e.g., methoxy and methoxymethoxy), alkylenedioxy (e.g. methylenedioxy), optionally substituted amino (e.g., alkylamino, dialkylamino, carbonylamino, benzyloxycarbonylamino or "CBZ-amino", and carboxamido), optionally substituted amidino, optionally substituted aryl (e.g., phenyl and 4-methyl-phenyl or "tolyl"), optionally substituted aralkyl (e.g., benzyl), optionally substituted aryloxy (e.g., phenoxy), optionally substituted aralkoxy (e.g., benzyloxy), optionally substituted heteroaryl, optionally substituted heteroaralkyl, optionally substituted heteroaryloxy, optionally substituted heteroaralkoxy, carboxy (—COOH), cyano, halogen, hydroxy, nitro, sulfanyl, sulfinyl, sulfonyl and thio.

The term "sulfanyl" refers to the groups: —S-(optionally substituted alkyl), —S-(optionally substituted aryl), —S-(optionally substituted heteroaryl), and —S-(optionally substituted heterocyclyl).

The term "sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocyclyl).

The term "sulfonyl" refers to the groups: —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), —S(O$_2$)-(optionally substituted heterocyclyl), —S(O$_2$)-(optionally substituted alkoxy), —S(O$_2$)-optionally substituted aryloxy), —S(O$_2$)-(optionally substituted heteroaryloxy), and —S(O$_2$)-(optionally substituted heterocyclyloxy).

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown are designated (+) or (−) depending on the direction (dextro- or levorotatory) which they rotate plane polarized light at the wavelength of the sodium D line. The term "substantially pure" means having at least about 95% chemical purity with no single impurity greater than about 1%. The term "substantially optically pure" or "substantially enantiomerically pure" means having at least about 95% enantiomeric excess. The invention contemplates the use of pure enantiomers and mixtures of enantiomers, including racemic mixtures, although the use of a substantially optically pure enantiomer will generally be most suitable.

"Mitotic spindle formation" refers to the organization of microtubules into bipolar structures by mitotic kinesins. "Mitotic spindle dysfunction" refers to mitotic arrest, monopolar spindle formation or mitotic spindle malformation, in which context "malformation" encompasses the splaying of mitotic spindle poles, or otherwise causing morphological perturbation of the mitotic spindle. The term "inhibit" as used with reference to mitotic spindle formation, means altering mitotic spindle formation, including decreasing spindle formation, and increasing or decreasing spindle pole separation. "Anti-mitotic" means inhibiting or having the potential to inhibit mitosis, for example, as described above.

The term "pharmaceutically acceptable salts" is meant to include both acid and base addition salts. A "pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly suitable are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The term "therapeutically effective amount" or "effective amount" refers to that amount of a compound of Formula I that is sufficient to effect treatment, as defined below, when administered to a patient in need of such treatment. The therapeutically effective amount will vary depending upon the patient and disease condition being treated, the weight and age of the patient, the severity of the disease condition, the particular compound, pharmaceutically acceptable salt or solvate of Formula I chosen, the dosing regimen to be followed, timing of administration, the manner of administration and the like, all of which can readily be determined by one of ordinary skill in the art.

The term "treatment" or "treating" means any treatment of a disease in a patient, including:
a) preventing the disease, that is, causing the clinical symptoms of the disease not to develop;
b) inhibiting the disease, that is, slowing or arresting the development of clinical symptoms; and/or
c) relieving the disease, that is, causing the regression of clinical symptoms.

A "patient" for the purposes of the present invention includes humans and other animals, particularly mammals, and other organisms. Thus the methods are applicable to both human therapy and veterinary applications. In a particular embodiment the patient is a mammal, most particularly the patient is human.

Compounds of the Present Invention

The present invention provides certain heterocyclic-fused pyrimidinone derivatives such as: pyrido[α,β-γ]pyrimidin-δ-ones, pyrimido[α,β-γ]pyrimidin-δ-ones, pyrimido[α,β-γ]pyridazin-δ-ones, and pteridin-4-ones. The compounds are inhibitors of one or more mitotic kinesins. By inhibiting mitotic kinesins, particularly KSP, but not other kinesins (e.g., transport kinesins), specific inhibition of cellular proliferation is accomplished. Thus, the present invention capitalizes on the finding that perturbation of mitotic kinesin function causes malformation or dysfunction of mitotic spindles, frequently resulting in cell cycle arrest and cell death.

Accordingly, the present invention relates to one or more compounds selected from the group represented by Formula I:

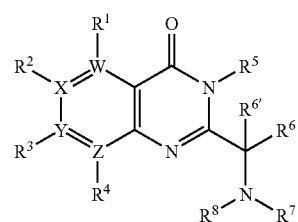

Formula I where:
W, X, Y and Z are independently —N═ or —C═, provided that at least one but no more than two of W, X, Y and Z are —N═;
$R^1$, $R^2$, $R^3$ and $R^4$ are independently hydrogen, hydroxy, optionally substituted alkyl, optionally substituted alkoxy, halogen or cyano, provided that $R^1$, $R^2$, $R^3$ or $R^4$ is absent where W, X, Y or Z, respectively, is —N═;
$R^5$ is optionally substituted alkyl or optionally substituted aryl;
$R^6$ and $R^{6'}$ are independently hydrogen, optionally substituted alkyl or optionally substituted aryl, or $R^6$ taken together with $R^{6'}$ is optionally substituted cycloalkyl or optionally substituted heterocycloalkyl having 5 to 7 ring atoms;
$R^7$ is optionally substituted alkyl or optionally substituted aryl; and
$R^8$ is hydrogen, —C(O)—$R^9$, —S(O)$_2$—$R^9$, —CH$_2$—$R^9$, —C(O)—O—$R^9$, —C(O)—NH—$R^9$ or —S(O)$_2$—NH—$R^9$, in which:

R[9] is hydrogen, optionally substituted alkyl, optionally substituted aryl or optionally substituted heteroaryl;

or R[7] taken together with R[8] is optionally substituted imidazolyl or optionally substituted imidazolinyl, and the pharmaceutically acceptable salts and solvates thereof.

Many of the compounds described herein contain one or more asymmetric centers (e.g. the carbon to which R[6] and R[6'] are attached when R[6] and R[6'] are different) and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that such compounds include both E and Z geometric isomers. All tautomeric forms are also intended to be included. The present invention is meant to include all such possible isomers, including racemic mixtures, intermediate mixtures, optically pure forms, substantially optically pure forms, substantially enantiomerically pure forms, and substantially pure forms, for example, in the particular embodiment where R[6] and R[6'] are different and the stereogenic center to which R[6] is attached is of the (R)-configuration.

Nomenclature

In the present specification, use of the symbols α, β, γ and δ in the names pyrido[α,β-γ]pyrimidin-δ-ones, pyrimido[α,β-γ]pyrimidin-δ-ones and pyrimido[α,β-γ]pyridazin-δ-ones is intended to generically describe the various positions of nitrogens and double bonds in the compounds, such as, e.g., pyrimido[4,5-c]pyridazin-5-ones and pyrimido[5,4-c]pyridazin-8-ones.

The compounds of Formula I can be named and numbered (e.g., using AutoNom version 2.1 in ISIS-DRAW or ChemDraw) as described below. For example, the compound of Formula IA:

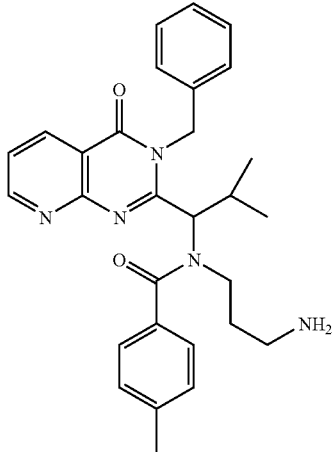

Formula IA i.e., the compound according to Formula I where W, X and Y are —C═; Z is —N═; R[1], R[2] and R[3] are H; R[4] is absent;

R[5] is benzyl; R[6] is i-propyl; R[6'] is H; R[7] is amino-propyl-; and R[8] is —C(O)—R[9] where R[9] is p-methyl-phenyl, can be named N-(3-amino-propyl)-N-[1-(3-benzyl-4-oxo-3,4-dihydro-pyrido[2,3-d]pyrimidin-2-yl)-2-methyl-propyl]-4-methyl-benzamide.

The compound of Formula IB:

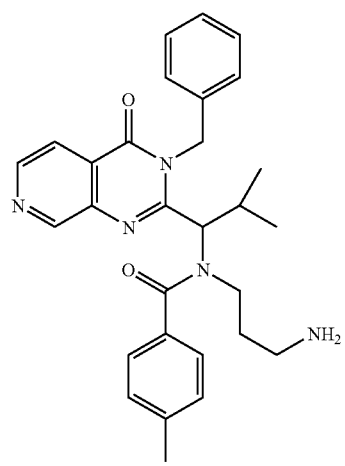

Formula IB i.e., the compound according to Formula I where W, X and Z are —C═; Y is —N═; R[1], R[2] and R[4] are H; R[3] is absent; R[5] is benzyl; R[6] is i-propyl; R[6'] is H; R[7] is amino-propyl-; and R[8] is —C(O)—R[9] where R[9] is p-methyl-phenyl, can be named N-(3-amino-propyl)-N-[1-(3-benzyl-4-oxo-3,4-dihydro-pyrido[3,4-d]pyrimidin-2-yl)-2-methyl-propyl]4-methyl-benzamide.

The compound of Formula IC:

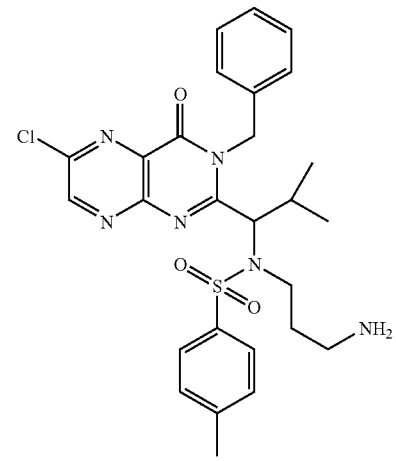

Formula IC i.e., the compound according to Formula I where W and Z are —N═; X and Y are —C═; R[1] and R[4] are absent; R[2] is Cl, R[3] is H; R[5] is benzyl; R[6] is i-propyl; R[6'] is H; R[7] is amino-propyl-; and $R^8$ is —S(O)$_2$—$R^9$ where $R^9$ is p-methyl-phenyl, can be named N-(3-amino-propyl)-N-[1-(3-benzyl-6-chloro-4-oxo-3,4-dihydro-pteridin-2-yl)-2-methyl-propyl]-4-methyl-benzenesulfonamide.

The compound of Formula ID:

Formula ID

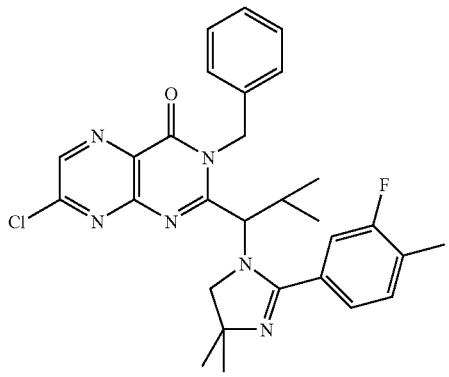

i.e., the compound according to Formula I where W and Z are —N═; X and Y are —C═; $R^1$ and $R^4$ are absent; $R^2$ is hydrogen; $R^3$ is Cl; $R^5$ is Benzyl; $R^6$ is Isopropyl; $R^{6'}$ is H; $R^7$ taken together with $R^8$ is 2-(3-Fluoro-4-methyl-phenyl)-4,4-dimethyl-4,5-dihydro-imidazol-1-yl-; can be named (±)-3-benzyl-7-chloro-2-{1-[2-(3-fluoro-4-methyl-phenyl)-4,4-dimethyl-4,5-dihydro-imidazol-1-yl]-2-methyl-propyl}-3H-pteridin-4-one.

The compound of Formula IE:

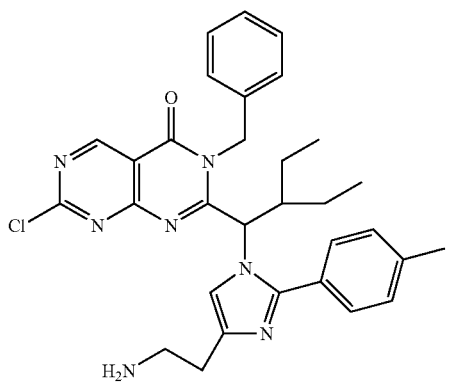

i.e., the compound according to Formula I where W and Y are —C═; X and Z are —N═; $R^1$ is H; $R^2$ is absent; $R^3$ is Cl; $R^4$ is absent; $R^5$ is Benzyl; $R^6$ is Isopentyl; $R^{6'}$ is H; $R^7$ taken together with $R^8$ is 4-(2-Amino-ethyl)-2-p-tolyl-imidazol-1-yl-; can be named (±)-2-{-1-[4-(2-amino-ethyl)-2-p-tolyl-imidazol-1-yl]-2-ethylbutyl}-3-benzyl-7-chloro-3H-pyrimido[4,5-d]pyrimidin-4-one.

The compound of Formula IF:

Formula IF

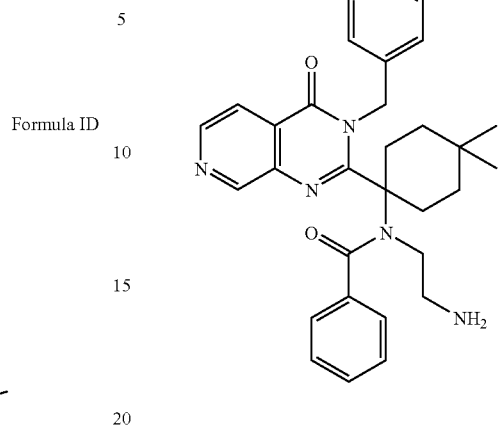

i.e., the compound according to Formula I where W, X and Z are —C═; Y is —N═; $R^1$, $R^2$ and $R^4$ are H; $R^3$ is absent; $R^5$ is benzyl; $R^6$ and $R^{6'}$ together are 4,4-dimethyl-cyclohexyl; $R^7$ is amino-ethyl-; and $R^8$ is —C(O)—$R^9$ where $R^9$ is phenyl, can be named N-(2-amino-ethyl)-N-[1-(3-benzyl-4-oxo-3,4-dihydro-pyrido[3,4-d]pyrimidin-2-yl)-4,4-dimethyl-cyclohexyl]-benzamide.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

When desired, the (R)- and (S)-isomers may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. For example, a compound of Formula I can be dissolved in a lower alkanol and placed on a Chiralpak AD (205×20 mm) column (Chiral Technologies, Inc.) conditioned for 60 min at 70% EtOAc in Hexane. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

Synthesis of the Compounds of Formula I

The compounds of Formula I can be prepared by following the procedures described in U.S. patent application Ser. No. 10/366,828 and corresponding PCT Application No. US03/04713; and PCT Publication Nos. WO 01/30768 and WO 01/98278, by substituting the optionally substituted anthranilic acid with an optionally substituted amino-nicotinic acid, amino-isonicotinic acid, amino-pyridine-carboxylic acid, amino-pyrazine-carboxylic acid, amino-pyridazine-carboxylic acid or amino-pyrimidine-carboxylic acid. Syntheses of the compounds of Formula I are also described below with reference to Reaction Schemes 1 to 5.

Brief Description of Reaction Schemes

Reaction Scheme 1 illustrates synthesis of the compounds of Formula I where $R^7$ is optionally substituted alkyl or optionally substituted aryl, and $R^8$ is chosen from hydrogen, —C(O)—$R^9$, —S(O)$_2$—$R^9$, —CH$_2$—$R^9$, —C(O)—O—$R^9$, —C(O)—NH—$R^9$ and —S(O)$_2$—NH—$R^9$.

Reaction Scheme 2 illustrates synthesis of the compounds of Formula I where $R^7$ taken together with $R^8$ is optionally substituted imidazoline (the optional substituents being indicated as $R^a$, $R^b$ and $R^c$).

Reaction Scheme 3 illustrates synthesis of the compounds of Formula I where $R^7$ taken together with $R^8$ is an optionally substituted imidazole (the optional substituent being indicated as $R^c$).

Reaction Scheme 4 illustrates synthesis of the compounds of Formula I where $R^7$ taken together with $R^8$ is an optionally di-substituted imidazole (one optional substituent being illustrated as 1,3-dioxo-1,3-dihydro-isoindol-2-yl or aminopropyl and the other optional substituent being indicated as $R^c$).

Reaction Scheme 5 illustrates an alternative synthesis of the compounds of Formula I where $R^7$ is optionally substituted alkyl or optionally substituted aryl, and $R^8$ is chosen from hydrogen, —C(O)—$R^9$, —S(O)$_2$—$R^9$, —CH$_2$—$R^9$, —C(O)—O—$R^9$, —C(O)—NH—$R^9$ and —S(O)$_2$—NH—$R^9$, which is particularly suitable for synthesizing the compounds of Formula I where X is =N—.

Reaction Schemes 1 and 5 illustrate syntheses for obtaining stereochemically enriched or pure compounds. The syntheses of Reaction Schemes 2, 3 and 4 can likewise provide stereochemically enriched or pure products, by employing the corresponding stereospecific starting material of Formula 107 (such as the (R)-enantiomer shown as Formula 107a in Reaction Schemes 1 and 5).

Starting Materials

The optionally substituted amino-nicotinic acid, amino-isonicotinic acid, amino-pyridine-carboxylic acid, amino-pyrazine-carboxylic acid, amino-pyridazine-carboxylic acid and amino-pyrimidine-carboxylic acids of Formula 101 and other reactants are commercially available, e.g., from Aldrich Chemical Company, Milwaukee, Wis. or may be readily prepared by those skilled in the art using commonly employed synthetic methodology.

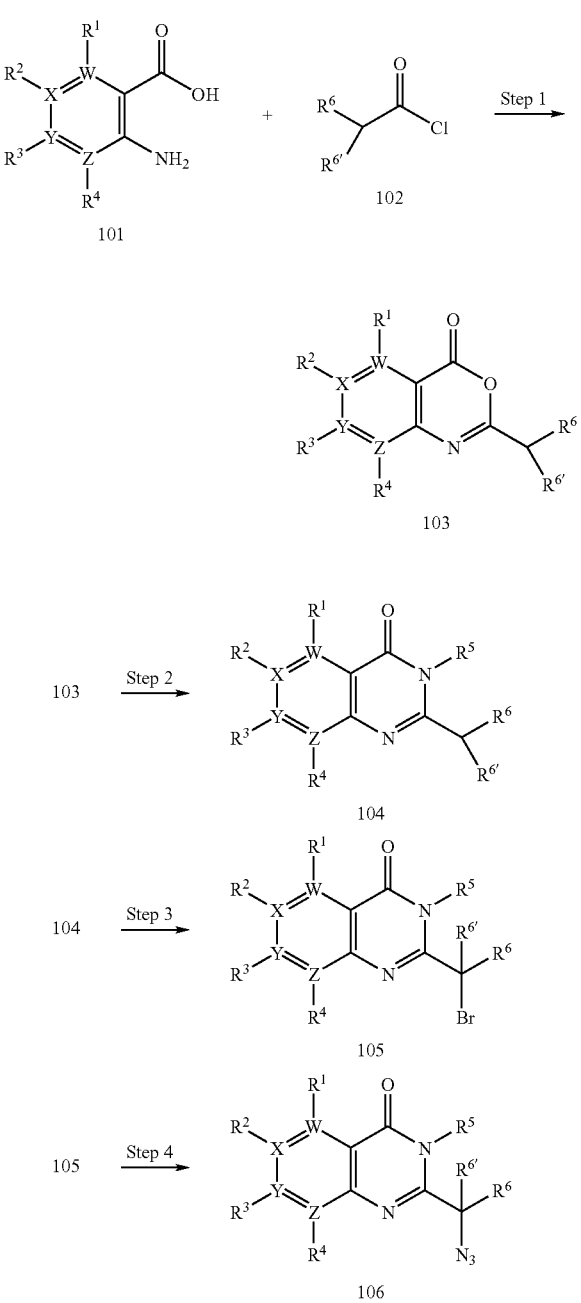

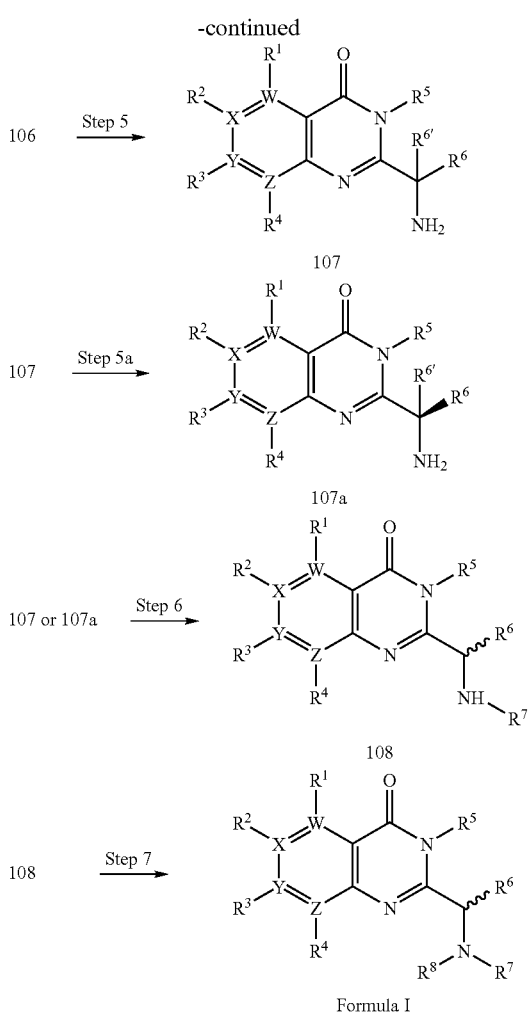

Preparation of Formula 103 Referring to Reaction Scheme 1, Step 1, to an optionally substituted: amino-nicotinic acid, amino-isonicotinic acid, amino-pyridine-carboxylic acid, amino-pyrazine-carboxylic acid, amino-pyridazine-carboxylic acid and amino-pyrimidine-carboxylic acid (such as 2-amino-nicotinic acid—the compound of Formula 101 where W, X and Y are —C=; Z is —N=; $R^1$, $R^2$ and $R^3$ are H; and $R^4$ is absent) dissolved in an inert organic solvent (such as THF) in the presence of sodium bicarbonate and a dehydrating agent (such as $Na_2SO_4$) is added a slight molar excess of an optionally substituted acid chloride (such as 3-methyl butyryl chloride or isovaleryl chloride—the compound of Formula 102 where $R^6$ is i-propyl and $R^{6'}$ is H), maintaining about room temperature. Completion of the reaction takes place over 2 hours and is monitored, e.g., by TLC. The solvent is then replaced with acetic anhydride, which is heated to about 90-100° C. for about 16 hours, monitoring completion of the reaction (e.g., by TLC) followed by removal of the acetic anhydride under vacuum at about 80-100° C. The reaction mixture is cooled and the corresponding, optionally substituted compound of Formula 103 (such as 2-1-propyl-pyrido[2,3-d][1,3]oxazin-4-one—the compound where W, X and Y are —C=; Z is —N=; $R^1$, $R^2$ and $R^3$ are H; $R^4$ is absent; $R^6$ is i-propyl; and $R^{6'}$ is H) is isolated and purified. Generic nomenclature for the compounds of Formula 103 is as follows:

2-substituted-pyrido[3,2-d][1,3]oxazin-4-one (where W is —N=, and X, Y and Z are —C=),
2-substituted-pyrido[4,3-d][1,3]oxazin-4-one (where X is —N=, and W, Y and Z are —C=),
2-substituted-pyrido[3,4-d][1,3]oxazin-4-one (where Y is —N=, and W, X and Z are —C=),
2-substituted-pyrido[2,3-d][1,3]oxazin-4-one (where Z is —N=, and W, X and Y are —C=),
6-substituted-7-oxa-1,2,5-triaza-naphthalen-8-one (where W and X are —N=, and Y and Z are —C=), and
2-substituted-pyridazino[4,5-d][1,3]oxazin-4-one (where X and Y are —N=, and W and Z are —C=),
7-substituted-pyridazino[3,4-d][1,3]oxazin-5-one (where Y and Z are —N=, and W and X are —C=),
2-substituted-pyazino[2,3-d][1,3]oxazin-4-one (where W and Z are —N=, and X and Y are —C=),
2-substituted-pyrimido[α,β-d][1,3]oxazin-4-one (where W and Y are —N=, and X and Z are —C=) and where (where X and Z are —N=, and W and Y are —C=).

Preparation of Formula 104 Referring to Reaction Scheme 1, Step 2, about 1.5 molar equivalents of a primary amine of the formula $R^5$—$NH_2$ where $R^5$ is as described above (such as benzylamine) and 1 molar equivalent of a compound of Formula 103 in an inert organic solvent (such as toluene or chloroform) are heated to reflux. The reaction takes place over a period of 1 to 5 hours, preferably 3 hours. After removal of water, ethylene glycol and sodium hydroxide (or sodium carbonate) are added to the reaction mixture and the temperature raised to 110-120° C. Completion of the reaction is monitored, e.g., by TLC. The corresponding, optionally substituted compound of Formula 104 (such as 2-i-propyl-3-benzyl-3H-pyrido[2,3-d]pyrimidin-4-one—where W, X and Y are —C=; Z is —N=; $R^1$, $R^2$ and $R^3$ are H; $R^4$ is absent; $R^5$ is benzyl; $R^6$ is i-propyl; and $R^{6'}$ is H) is isolated and purified. Generic nomenclature for the compounds of Formula 104 is as follows:

3-($R^5$-substituted)-2-($R^6$-substituted)-3H-pyrido[3,2-d]pyrimidin-4-one (where W is —N=, and X, Y and Z are —C=),
3-($R^5$-substituted)-2-($R^6$-substituted)-3H-pyrido[4,3-d]pyrimidin-4-one (where X is —N=, and W, Y and Z are —C=),
3-($R^5$-substituted)-2-($R^6$-substituted)-3H-pyrido[3,4-d]pyrimidin-4-one (where Y is —N=, and W, X and Z are —C=),
3-($R^5$-substituted)-2-($R^6$-substituted)-3H-pyrido[2,3-d]pyrimidin-4-one (where Z is —N=, and W, X and Y are —C=),
7-($R^5$-substituted)-6-($R^6$-substituted)-7H-pyrimido[5,4-c]pyridazin-8-one (where W and X are —N=, and Y and Z are —C=), and
3-($R^5$-substituted)-2-($R^6$-substituted)-3H-pyrimido[5,4-c]pyridazin-8-one (where X and Y are —N=, and W and Z are —C=),
6-($R^5$-substituted)-7-($R^6$-substituted)-6H-pyrimido[4,5-c]pyridazin-5-one (where Y and Z are —N=, and W and X are —C=),
3-($R^5$-substituted)-2-($R^6$-substituted)-3H-pteridin-4-one (where W and Z are —N=, and X and Y are —C=),
3-($R^5$-substituted)-2-($R^6$-substituted)-3H-pyrimido[5,4-d]pyrimidin-4-one (where W and Y are —N=, and X and Z are —C=), and
3-($R^5$-substituted)-2-($R^6$-substituted)-3H-pyrimido[4,5-d]pyrimidin-4-one (where X and Z are —N=, and W and Y are —C=).

Preparation of Formula 105 Referring to Reaction Scheme 1, Step 3, a compound of Formula 104, dissolved in acetic acid and in the presence of sodium acetate, is heated to 30-50° C., followed by the addition (with agitation) of a slight molar excess of bromine in acetic acid over a period of 2 to 4 hours. Completion is monitored, e.g., by TLC; if the starting material continues to be present, the temperature is increased to 50° C. until completion. The corresponding, optionally substituted compound of Formula 105 (such as 2-(1-bromo-i-propyl)-3-benzyl-3H-pyrido[2,3-d]pyrimidin-4-one—where W, X and Y are —C═; Z is —N═; $R^1$, $R^2$ and $R^3$ are H; $R^4$ is absent; $R^5$ is benzyl; $R^6$ is i-propyl; and $R^{6'}$ is H) is isolated and purified. Other compounds of Formula 105 are (1-bromo-$R^6$-substituted) derivatives otherwise following the generic nomenclature for Formula 104.

Preparation of Formula 106 Referring to Reaction Scheme 1, Step 4, to 1.5 molar equivalents of sodium azide in an inert organic solvent (such as DMF) is slowly added 1 molar equivalent of a compound of Formula 105. The reaction takes place with agitation at a temperature of 40-60° C. over a period of 3 to 10 hours. Completion is monitored, e.g., by TLC. The corresponding, optionally substituted compound of Formula 106 (such as 2-(1-azido-i-propyl)-3-benzyl-3H-pyrido[2,3-d]pyrimidin-4-one—where W, X and Y are —C═; Z is N; $R^1$, $R^2$ and $R^3$ are H; $R^4$ is absent; $R^5$ is benzyl; $R^6$ is i-propyl; and $R^{6'}$ is H) is isolated and purified. Other compounds of Formula 106 are (1-azido-$R^6$-substituted) derivatives otherwise following the generic nomenclature for Formula 104.

Preparation of Formula 107 Referring to Reaction Scheme 1, Step 5, to a solution of triphenylphosphine dissolved in an inert organic solvent (such as THF) is added an azide of Formula 106, portionwise over 15 minutes. The reaction takes place with agitation, maintaining the temperature at 20° C. over a period of 5 minutes to 2 hours. The reaction mixture is acidified and solvents removed followed by conventional work up to give the hydrochloride salt of the corresponding, optionally substituted compound of Formula 107 (such as 2-(1-amino-i-propyl)-3-benzyl-3H-pyrido[2,3-d]pyrimidin-4-one—where W, X and Y are —C═; Z is N; $R^1$, $R^2$ and $R^3$ are H; $R^4$ is absent; $R^5$ is benzyl; $R^6$ is i-propyl; and $R^{6'}$ is H), which is isolated and purified. Other compounds of Formula 107 are (1-amino-$R^6$-substituted) derivatives otherwise following the generic nomenclature for Formula 104.

Preparation of Formula 107a In certain compounds of the invention, a particular stereoconfiguration can be selected for the $R^6$ substituent, such as the (R) isomer, which can be obtained, e.g., as illustrated in optional Step 5a of Reaction Scheme 1. An amine of Formula 107 is dissolved in an inert organic solvent (such as IPA) and warmed to 60° C. In a separate vessel, a resolving agent (such as dibenzoyl-D-tartaric acid) is dissolved, preferably in the same warm solvent, and then quickly added (with agitation) to the warm amine solution. The reaction mixture is left to crystallize by cooling to room temperature over 16 hours under continuing agitation. The desired isomer, e.g., the (R) isomer illustrated as Formula 107a, is isolated and purified.

Preparation of Formula 108 For the sake of brevity in the remaining description of the syntheses of compounds of Formula I, it should be understood that either single isomer or a mixture of isomers may be employed to give the corresponding product. In that regard, the $R^6$ substituent in Formula 108 is shown attached by a wavy line, which is meant to encompass either single isomer or any mixture of isomers, and the $R^{6'}$ substituent is thereafter illustrated as being hydrogen.

Referring to Reaction Scheme 1, Step 6, a compound of Formula 107 (or a single isomer such as Formula 107a) is dissolved in an inert solvent (such as dichloromethane) in the presence of a slight molar excess of an alkali metal acetate borohydride [such as Na(OAc)$_3$BH] and the solution cooled to 10° C. To this solution is added, portionwise, 1.4 molar equivalents of an $R^7$ aldehyde of the formula $R^7$═O where $R^7$ is as described above or is a protected precursor to such a substituent [e.g., (3-oxo-propyl)-carbamic acid tert-butyl ester or 3-(1,3-dioxo-1,3-dihydro-isoindol-2-yl)-propionaldehyde]; the solution can be allowed to warm to room temperature. Completion over a period of 3 hours is monitored, e.g., by TLC. The corresponding, optionally substituted compound of Formula 108 (such as N-{3-[1-(3-benzyl-4-oxo-3,4-dihydro-pyrido[2,3-d]pyrimidin-2-yl)-2-methyl-proplyamino]-propyl}-carbamic acid tert butyl ester—where W, X and Y are —C═; Z is —N═; $R^1$, $R^2$ and $R^3$ are H; $R^4$ is absent; $R^5$ is benzyl; $R^6$ is i-propyl; and $R^7$ is 3-Boc-amino-propyl), is isolated and purified. Other compounds of Formula 108 are (substituted-amino-$R^6$-substituted) derivatives, the nomenclature for which will depend on whether a protecting group is present.

The protected $R^7$ substituent can be de-protected at this point (e.g., by reaction with a large molar excess of TFA) to give the corresponding compound of Formula 108, which is also a compound of Formula I where $R^8$ is H. Alternatively, the compound of Formula 108 (whether $R^7$-protected or not, as appropriate) can be carried forward as described below and further derivatized to give the compounds of Formula I where $R^8$ is other than H.

Preparation of Formula I where $R^8$ is —C(O)—$R^9$, —S(O)$_2$—$R^9$, —CH$_2$—$R^9$, —C(O)—O—$R^9$, —C(O)—NH—$R^9$ or —S(O)$_2$—NH—$R^9$ Referring to Reaction Scheme 1, Step 7, a compound of Formula 108 and an inert solvent (such as dichloromethane) in the presence of over 2 molar equivalents of DIPEA is stirred until dissolved. To this solution is added a slight molar excess of an $R^8$ chloride [such as, Cl—C(O)—$R^9$, Cl—S(O)$_2$—$R^9$, Cl—CH$_2$—$R^9$, Cl—C(O)—O—$R^9$ and Cl—S(O)$_2$—NH—$R^9$] or an $R^8$ isocyanate (such as O═C═N—$R^9$) or an anhydride (such as O[C(O)$R^9$]$_2$ or O[S(O)$_2R^9$]$_2$) where $R^9$ is as described above, e.g., toluoyl chloride. The reaction takes place, with stirring, at room temperature to 50° C. over a period of 4 to 6 hours. Completion is monitored, e.g., by TLC. The corresponding compound of Formula I is de-protected (if necessary) isolated and purified. Nomenclature follows the examples set forth above in the nomenclature section.

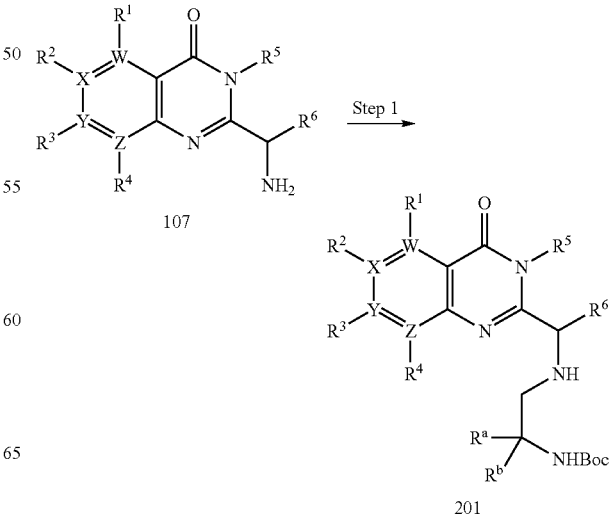

Reaction Scheme 2

-continued

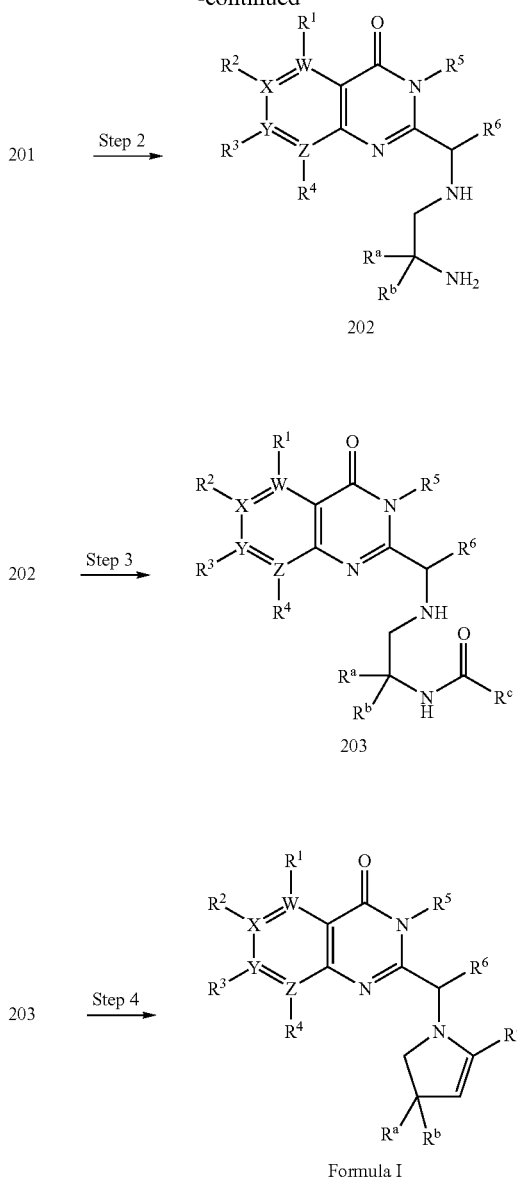

Alternatively, the primary amine of Formula 202 can be chemoselectively acylated in the presence of an acyl chloride of the formula R$^c$C(O)Cl, triethylamine, and dichloromethane, followed by acetic acid mediated cyclization at reflux to provide the imidazoline of Formula I without isolation of the amide intermediate of Formula 203.

Reaction Scheme 3

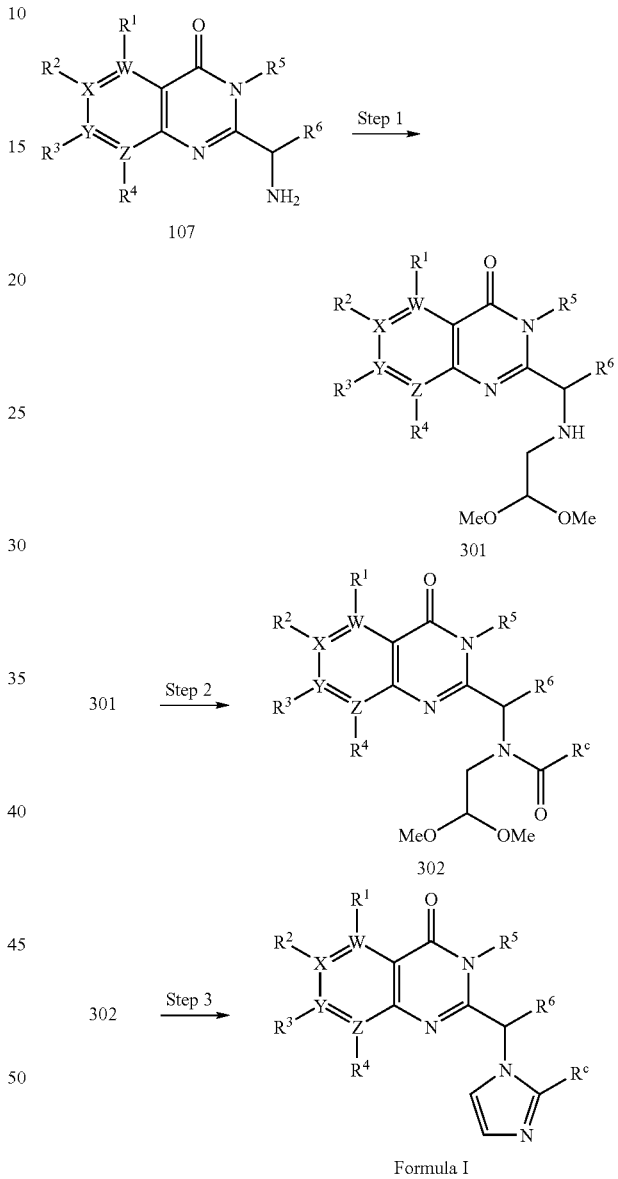

Formula I

In Reaction Scheme 2, Step 1, an amine of Formula 107 (prepared, e.g,. as described with reference to Reaction Scheme 1) undergoes reductive amination with a (2-oxoethyl)-carbamic acid tert-butyl ester, sodium triacetoxyborohydride, and dichloromethane to give the compound of Formula 201; the reaction takes place at ambient temperature over a period of 4 hours. In Step 2, the Boc protecting group is removed via contact with dichloromethane:trifluoroacetic acid (4:1) to give the compound of Formula 202; the reaction takes place at ambient temperature over a period of 16 hours. In Step 3, the primary amine of Formula 202 is chemoselectively acylated in the presence of an acyl chloride of the formula R$^c$C(O)Cl, triethylamine, and dichloromethane; the reaction takes place at ambient temperature over a period of 3 hours to give the amide of Formula 203. In Step 4; the amide is dehydratively cyclized by contact with phosphorus oxychloride at reflux; the reaction takes place over 8 hours to give the corresponding imidazoline of Formula I.

In Reaction Scheme 3, Step 1, an amine of Formula 107 is contacted with bromoacetaldehyde dimethylacetal and potassium carbonate; the reaction takes place over 18 hours at 135° C. to give the dimethoxyethyl amine of Formula 301. The secondary amine of Formula 301 is contacted with an acyl chloride of the formula R$^c$C(O)Cl, triethylamine, and dichloromethane; the reaction takes place at ambient temperature over a period of 18 hours to give the tertiary amine of Formula 302. The tertiary amide of Formula 302 is cyclized using ammonium acetate in acetic acid; the reaction takes place at reflux over a period of 2 hours to give the substituted imidazolyl compound of Formula I.

Reaction Scheme 4

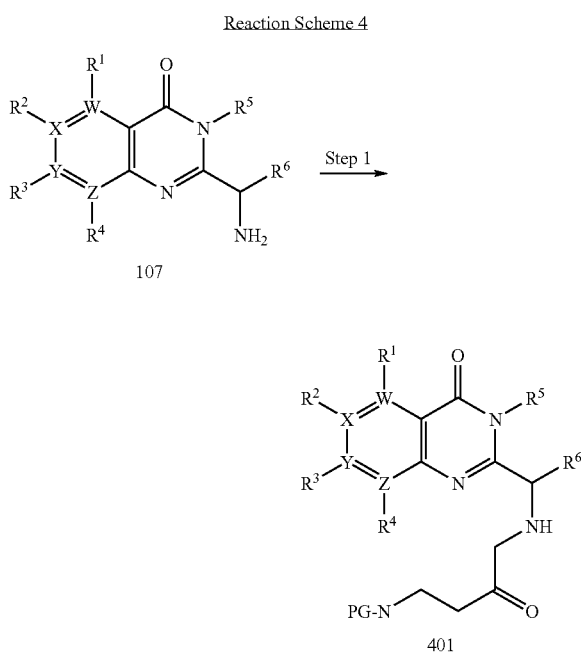

In Reaction Scheme 4, Step 1, an amine of Formula 107 is contacted with a compound of the formula X—CH$_2$—C(O)—CH$_2$CH$_2$—N—PG [where X is a leaving group (particularly bromo) and PG is an amino protecting group (particulary phthalimido)] and potassium carbonate; the reaction takes place at ambient temperature over a period of 1.5 hours and the resulting secondary amine of Formula 401 can be carried forward to Step 2 without further purification. In Step 2, the secondary amine of Formula 401 is contacted with an acyl chloride of the formula R$^c$C(O)Cl, triethylamine, and dichloromethane; the reaction takes place at ambient temperature over a period of 2 hours to give the tertiary amine of Formula 402. The tertiary amine of Formula 402 is cyclized using ammonium acetate in acetic acid; the reaction takes place at reflux over a period of 6 hours to give the di-substituted imidazolyl compound of Formula 403 (also a compound within the scope of Formula I). In Step 4, the compound of Formula 403 is de-protected to give the corresponding primary amine of Formula I. When the amine of Formula 403 is protected as the phthalmide, this can be accomplished, for example, by contact with hydrazine in ethanol; the reaction takes place at reflux over a period of 3 hours.

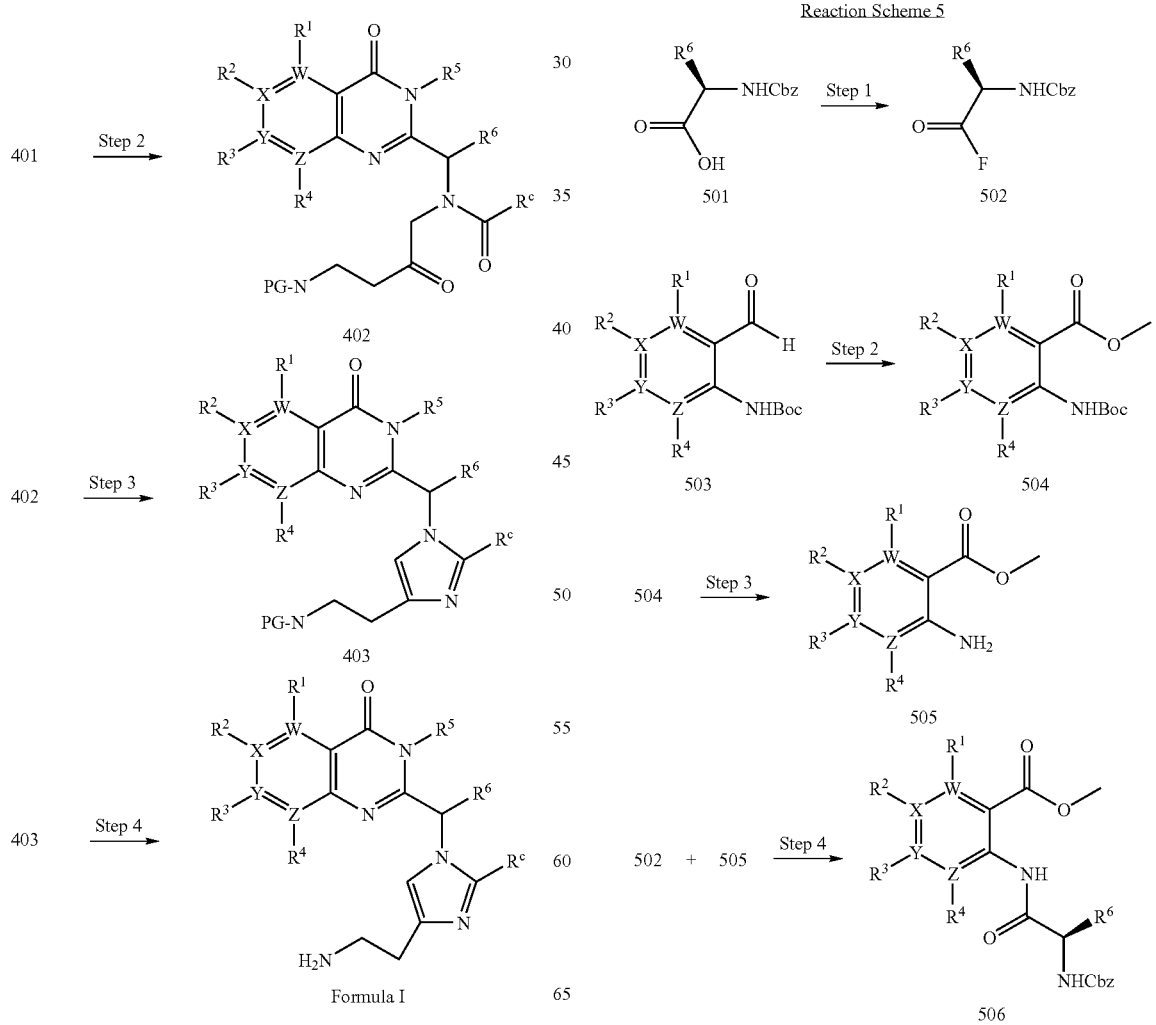

Reaction Scheme 5

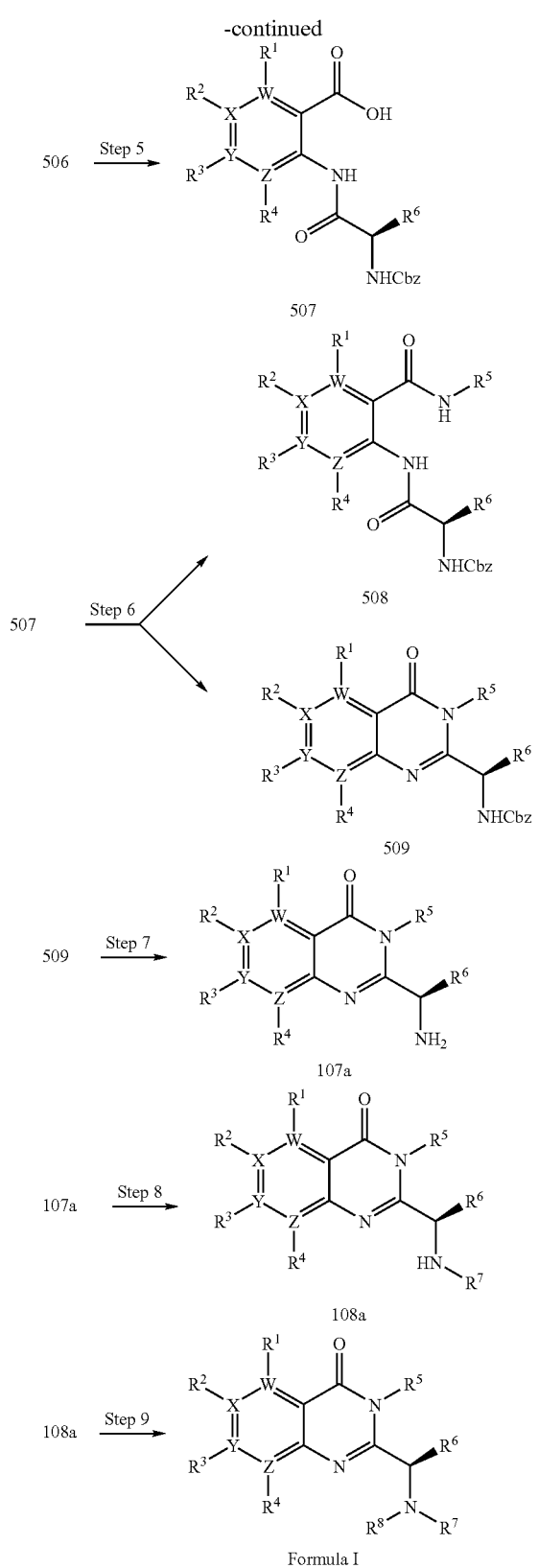

Formula I line) is dissolved in an organic solvent (e.g., dichloromethane), contacted with cyanuric fluoride (0.75 molar equivalents), and allowed to stir for 16 hours. Following filtration, the remaining solution is washed, dried and the solvent evaporated to afford the acid fluoride of Formula 502.

Preparation of Formula 504 Referring to Reaction Scheme 5, Step 2, a protected 4-amino-heteroaryl carboxaldehyde of Formula 503 is dissolved in a solvent (e.g., methanol) and contacted with large molar excesses of N-iodosuccinimide and potassium carbonate. The reaction takes place with stirring at room temperature over a period of 1 hour, followed by quenching with saturated $Na_2S_2O_3$. The methyl ester of Formula 504 is then isolated and purified.

Preparation of Formula 505 Referring to Reaction Scheme 5, Step 3, a methyl ester of Formula 504 is de-protected, for example using TFA (e.g., dissolved in 50/50 solution of TFA/DCM). The reaction takes place with stirring at room temperature over a period of 2 hours. Following conventional work-up, the corresponding de-protected methyl ester of Formula 505 is obtained.

Preparation of Formula 506 Referring to Reaction Scheme 5, Step 4, a de-protected methyl ester of Formula 505 is dissolved in a solvent (e.g., dichloromethane) with a slight molar excess of diisopropylethyl amine. A slight molar excess of an acid fluoride of Formula 502 is added. The reaction takes place with stirring at room temperature over a period of 16 hours. Solvent removal under reduced pressure and purification by flash silica gel chromatography afford the corresponding amide of Formula 506.

Preparation of Formula 507 Referring to Reaction Scheme 5, Step 5, an amide of Formula 506 is dissolved in a solvent and contacted with a twice molar excess of sodium hydroxide. The reaction takes place with stirring at room temperature over a period of 1 hour, followed by the addition of silica gel with continued stirring for an additional 10 minutes. The silica gel is filtered off and the solvents evaporated to afford the corresponding carboxylic acid of Formula 507.

Preparation of Formulae 508 and 509 Referring to Reaction Scheme 5, Step 6, an acid of Formula 507 is dissolved (e.g., in dichloromethane) and contacted with a slight molar excess of a coupling reagent such as EDC. The solution is stirred at room temperature for 2 hours until the complete consumption of the starting material is observed by reverse phase HPLC. A twice molar excess of a primary amine of the formula $R^5$—$NH_2$ (such as benzylamine) is added. The reaction takes place with stirring at room temperature over a period of 16 hours. The mixture is concentrated under vacuum and purified by silica gel chromatography to separate the uncyclized product of Formula 508 and the cyclized, enantiomerically pure product of Formula 509.

Preparation of Formulae 107a, 108a and Formula I Referring to Reaction Scheme 5, Step 7, an enantiomerically pure, cyclized compound of Formula 509 is de-protected, for example by dissolution in a solution of HBr/acetic acid. The reaction takes place with stirring at room temperature over a period of 2 hours. Solvent removal affords the corresponding enantiomerically pure de-protected amine of Formula 107a, which can be carried forward to the corresponding enantiomerically pure secondary and tertiary amines of Formulae 108a and Formula I, for example as described with reference to Reaction Scheme 1, Steps 6 and 7.

Compounds prepared by the above-described process of the invention can be identified, e.g., by the presence of a detectable amount of Formulae 106, 107, 107a, 108, 108a, 203, 302, 402, 403 or 509. While it is well known that Preparation of Formula 502 Referring to Reaction Scheme 5, Step 1, an N-benzyloxy carbonyl amino acid of Formula 501 (preferably a chiral amino acid such as D-vapharmaceuticals must meet pharmacopoeia standards before approval and/or marketing, and that synthetic reagents, precursors and reaction products (such as 2,3-dihydro-phthalazine-1,4-dione, a reaction product resulting from hydrazine deprotection of a phthalimide-protected compound of Formula I) should not exceed the limits prescribed by pharmacopoeia standards, final compounds prepared by a process of the present invention may have minor, but detectable, amounts of such materials present, for example at levels in the range of 95% purity with no single impurity greater than 1%. These levels can be detected, e.g., by emission spectroscopy. It is important to monitor the purity of pharmaceutical compounds for the presence of such materials, which presence is additionally disclosed as a method of detecting use of a process of the invention.

Particular Optional Processes and Last Steps

A compound of Formula 108:

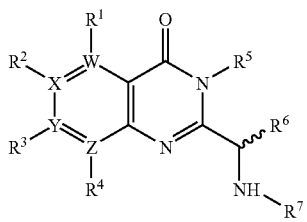

108

(where $R^7$ is optionally protected) is contacted with a slight molar excess of an $R^8$ chloride [such as, Cl—C(O)—$R^9$, Cl—S(O)$_2$—$R^9$, Cl—CH$_2$—$R^9$, Cl—C(O)—O—$R^9$ and Cl—S(O)$_2$—NH—$R^9$] or an $R^8$ isocyanate (such as O=C=N—$R^9$) or an anhydride (such as O[C(O)$R^9$]$_2$ or O[S(O)$_2R^9$]$_2$) to give the corresponding optionally protected compound of Formula I.

An $R^7$-protected compound of Formula I is deprotected.

A compound of Formula 203, 302 or 402 is cyclized by acetic acid-mediated cyclization.

A phthalimide-protected compound of Formula I is converted to the corresponding primary amine of Formula I, e.g., by contact with hydrazine.

A racemic mixture of isomers of a compound of Formula I is placed on a chromatography column and separated into (R)- and (S)-enantiomers.

A compound of Formula I is contacted with a pharmaceutically acceptable acid to form the corresponding acid addition salt.

A pharmaceutically acceptable acid addition salt of Formula I is contacted with a base to form the corresponding free base of Formula I.

Particular Compounds

Particular embodiments of the compounds of Formula I, pharmaceutically acceptable salts and solvates thereof, compositions including pharmaceutical formulations, methods of manufacture and methods of use of the present invention include the following combinations and permutations of substituent groups in Formula I (indented/sub-grouped, respectively, in increasing order of particularity):

$R^1$, $R^2$, $R^3$ and $R^4$ are chosen from hydrogen, halo (especially chloro and fluoro), lower alkyl (especially methyl), substituted lower alkyl, lower alkoxy (especially methoxy), and cyano or is/are absent.

Two or three of $R^1$, $R^2$, $R^3$ and $R^4$ are hydrogen.
Three of $R^1$, $R^2$, $R^3$ and $R^4$ are hydrogen, or two of $R^1$, $R^2$, $R^3$ and $R^4$ are hydrogen and the third is halo, lower alkoxy or cyano.
Where halo is chloro and lower alkoxy is methoxy.
$R^3$ is hydrogen, chloro, methoxy or cyano.
Three of $R^1$, $R^2$, $R^3$ and $R^4$ are hydrogen and the fourth is absent.
$R^5$ is optionally substituted aralkyl.
$R^5$ is benzyl or substituted benzyl.
$R^5$ is benzyl.
Where $R^6$ and $R^{6'}$ are different and the stereogenic center to which $R^6$ is attached is of the (R)-configuration.
Where W, X, Y, or Z is —N=, or W and Z are —N=.
Where X, Y or Z is —N=.
Where $R^6$ and $R^{6'}$ are different and the stereogenic center to which $R^6$ is attached is of the (R)-configuration.
Where Y or Z is —N=.
Where $R^1$, $R^2$, $R^3$ and $R^4$ are chosen from hydrogen, halo (especially chloro and fluoro), lower alkyl (especially methyl), substituted lower alkyl, lower alkoxy (especially methoxy), and cyano or is/are absent.
Where three of $R^1$, $R^2$, $R^3$ and $R^4$ are hydrogen and the fourth is absent.
Where $R^6$ is optionally substituted alkyl.
Where $R^6$ is lower alkyl.
Where lower alkyl is ethyl, i-propyl, c-propyl or t-butyl.
Where $R^6$ and $R^{6'}$ are different and the stereogenic center to which $R^6$ is attached is of the (R)-configuration.
Where $R^6$ and $R^{6'}$ are different and the stereogenic center to which $R^6$ is attached is of the (R)-configuration.
Where $R^{6'}$ is hydrogen.
Where $R^{6'}$ is hydrogen.
Where $R^{6'}$ is hydrogen.
Where $R^7$ is substituted alkyl.
Where $R^7$ is alkyl substituted with a primary-, secondary- or tertiary-amine.
Where $R^8$ is —C(O)—$R^9$ or —C(O)—OR$^9$.
Where $R^8$ is —C(O)—$R^9$, in which $R^9$ is: optionally substituted aryl (especially phenyl and lower alkyl-, lower alkoxy-, and/or halo-substituted phenyl), optionally substituted aralkyl (especially optionally substituted benzyl and phenylvinyl), aryloxyalkyl (especially phenoxy lower alkyl), optionally substituted heteroaryl, optionally substituted heteroaralkyl, or optionally substituted heteroaryloxyalkyl.
Where $R^9$ is optionally substituted alkyl, optionally substituted aryl or optionally substituted aralkyl.
Where $R^9$ is lower alkoxyalkyl, lower alkyl-substituted phenyl, lower alkoxy-substituted phenyl, halo-substituted phenyl, optionally substituted benzyl, phenoxy lower alkyl, optionally substituted heteroaryl, optionally substituted heteroaralkyl or optionally substituted heteroaryloxyalkyl
Where $R^9$ is lower alkoxyalkyl or substituted phenyl.
Where $R^9$ is methoxy-methyl or p-tolyl.
Where $R^8$ is —C(O)—OR$^9$, in which $R^9$ is: optionally substituted aryl (especially phenyl and lower alkyl-, lower alkoxy-, and/or halo-substituted phenyl) or optionally substituted heteroaryl.

Where $R^7$ taken together with $R^8$ is an optionally substituted imidazole or an optionally substituted imidazoline.
  Where $R^7$ taken together with $R^8$ is 2-(optionally substituted)-4,4-(optionally di-substituted)-4,5-dihydro-imidazol-1-yl.
    Where $R^7$ taken together with $R^8$ is 2-(optionally substituted aryl)-4,5-dihydro-imidazol-1-yl or 2-(optionally substituted aryl)-4,4-dimethyl-4,5-dihydro-imidazol-1-yl.
      Where $R^7$ taken together with $R^8$ is 2-(substituted phenyl)-4,5-dihydro-imidazol-1-yl or 2-(substituted phenyl)-4,4-dimethyl-4,5-dihydro-imidazol-1-yl.
        Where $R^7$ taken together with $R^8$ is 2-(4-methylphenyl)-4,5-dihydro-imidazol-1-yl, 2-(3-fluoro-4-methylphenyl)-4,5-dihydro-imidazol-1-yl, 2-(4-methylphenyl)-4,4-dimethyl-4,5-dihydro-imidazol-1-yl, 2-(3-fluoro-4-methylphenyl)-4,4-dimethyl-4,5-dihydro-imidazol-1-yl.
  Where $R^7$ taken together with $R^8$ is 2- and/or 4-substituted-imidazol-1-yl.
    Where $R^7$ taken together with $R^8$ is 2-substituted-imidazol-1-yl.
      Where $R^7$ taken together with $R^8$ is 2-(optionally substituted phenyl)-imidazol-1-yl.
        Where $R^7$ taken together with $R^8$ is 2-phenyl-imidazol-1-yl, 2-p-tolyl-imidazol-1-yl, 2-(4-fluoro-phenyl)-imidazol-1-yl, 2-(4-chloro-phenyl)-imidazol-1-yl, or 2-(3-fluoro-4-methyl-phenyl)-imidazol-1-yl.
    Where $R^7$ taken together with $R^8$ is 2,4-disubstituted-imidazol-1-yl.
      Where $R^7$ taken together with $R^8$ is 4-(optionally substituted alkyl)-2-(optionally substituted aryl)-imidazol-1-yl.
        Where $R^7$ taken together with $R^8$ is 4-(Ω-amino-lower alkyl)-2-(optionally substituted phenyl)-imidazol-1-yl, especially: 4-(2-amino-ethyl)-2-phenyl-imidazol-1-yl, 4-(2-amino-ethyl)-2-p-tolyl-imidazol-1-yl, 4-(2-amino-ethyl)-2-(4-fluoro-phenyl)-imidazol-1-yl, 4-(2-amino-ethyl)-2-(4-chloro-phenyl)-imidazol-1-yl, 4-(2-amino-ethyl)-2-(3-fluoro-4-methyl-phenyl)-imidazol-1-yl, 4-(aminomethyl)-2-phenyl-imidazol-1-yl, 4-(aminomethyl)-2-p-tolyl-imidazol-1-yl, 4-(aminomethyl)-2-(4-fluoro-phenyl)-imidazol-1-yl, 4-(aminomethyl)-2-(4-chloro-phenyl)-imidazol-1-yl, or 4-(aminomethyl)-2-(3-fluoro-4-methyl-phenyl)-imidazol-1-yl.
Where $R^6$ and $R^{6'}$ are different and the stereogenic center to which $R^6$ is attached is of the (R)-configuration.
Where W, X, Y, or Z is —N=, or W and Z are —N=.
  Where X, Y or Z is —N=.
    Where $R^6$ and $R^{6'}$ are different and the stereogenic center to which $R^6$ is attached is of the (R)-configuration.
    Where Y or Z is —N=.
Where $R^1$, $R^2$, $R^3$ and $R^4$ are chosen from hydrogen, halo (particularly chloro and fluoro), lower alkyl (particularly methyl), substituted lower alkyl, lower alkoxy (particularly methoxy), and cyano or is/are absent.
  Where three of $R^1$, $R^2$, $R^3$ and $R^4$ are hydrogen and the fourth is absent.
Where $R^6$ is optionally substituted alkyl.
  Where $R^6$ is lower alkyl.
    Where lower alkyl is ethyl, i-propyl, c-propyl or t-butyl.
      Where $R^6$ and $R^{6'}$ are different and the stereogenic center to which $R^6$ is attached is of the (R)-configuration.
Where $R^6$ and $R^{6'}$ are different and the stereogenic center to which $R^6$ is attached is of the (R)-configuration.
Where $R^{6'}$ is hydrogen.
Where $R^{6'}$ is hydrogen.
Where $R^7$ is substituted alkyl.
  Where $R^7$ is alkyl substituted with a primary-, secondary- or tertiary-amine.
Where $R^8$ is —C(O)—$R^9$ or —C(O)—$OR^9$.
  Where $R^8$ is —C(O)—$R^9$, in which $R^9$ is: optionally substituted aryl (particularly phenyl and lower alkyl-, lower alkoxy-, and/or halo-substituted phenyl), optionally substituted aralkyl (particularly optionally substituted benzyl and phenylvinyl), aryloxyalkyl (particularly phenoxy lower alkyl), optionally substituted heteroaryl, optionally substituted heteroaralkyl, or optionally substituted heteroaryloxyalkyl.
    Where $R^9$ is optionally substituted alkyl, optionally substituted aryl or optionally substituted aralkyl.
    Where $R^9$ is lower alkoxyalkyl, lower alkyl-substituted phenyl, lower alkoxy-substituted phenyl, halo-substituted phenyl, optionally substituted benzyl, phenoxy lower alkyl, optionally substituted heteroaryl, optionally substituted heteroaralkyl or optionally substituted heteroaryloxyalkyl
      Where $R^9$ is alkoxy-lower alkyl or substituted phenyl.
        Where $R^9$ is methoxy-methyl or p-tolyl.
  Where $R^8$ is —C(O)—$OR^9$, in which $R^9$ is: optionally substituted aryl (particularly phenyl, particularly lower alkyl-, lower alkoxy-, and/or halo-substituted phenyl) or optionally substituted heteroaryl.
Where $R^7$ taken together with $R^8$ is an optionally substituted imidazole or an optionally substituted imidazoline.
  Where $R^7$ taken together with $R^8$ is 2-(optionally substituted)-4,4-(optionally di-substituted)-4,5-dihydro-imidazol-1-yl.
    Where $R^7$ taken together with $R^8$ is 2-(optionally substituted aryl)-4,5-dihydro-imidazol-1-yl or 2-(optionally substituted aryl)-4,4-dimethyl-4,5-dihydro-imidazol-1-yl.
      Where $R^7$ taken together with $R^8$ is 2-(substituted phenyl)-4,5-dihydro-imidazol-1-yl or 2-(substituted phenyl)-4,4-dimethyl-4,5-dihydro-imidazol-1-yl.
        Where $R^7$ taken together with $R^8$ is 2-(4-methylphenyl)-4,5-dihydro-imidazol-1-yl, 2-(3-fluoro-4-methylphenyl)-4,5-dihydro-imidazol-1-yl, 2-(4-methylphenyl)-4,4-dimethyl-4,5-dihydro-imidazol-1-yl, 2-(3-fluoro-4-methylphenyl)-4,4-dimethyl-4,5-dihydro-imidazol-1-yl.
  Where $R^7$ taken together with $R^8$ is 2- and/or 4-substituted-imidazol-1-yl.
    Where $R^7$ taken together with $R^8$ is 2-substituted-imidazol-1-yl.
      Where $R^7$ taken together with $R^8$ is 2-(optionally substituted phenyl)-imidazol-1-yl.
        Where $R^7$ taken together with $R^8$ is 2-phenyl-imidazol-1-yl, 2-p-tolyl-imidazol-1-yl, 2-(4- fluoro-phenyl)-imidazol-1-yl, 2-(4-chloro-phenyl)-imidazol-1-yl, or 2-(3-fluoro-4-methylphenyl)-imidazol-1-yl.

Where $R^7$ taken together with $R^8$ is 2,4-disubstituted-imidazol-1-yl.

Where $R^7$ taken together with $R^8$ is 4-(optionally substituted alkyl)-2-(optionally substituted aryl)-imidazol-1-yl.

Where $R^7$ taken together with $R^8$ is 4-(Ω-amino-lower alkyl)-2-(optionally substituted phenyl)-imidazol-1-yl, especially: 4-(2-amino-ethyl)-2-phenyl-imidazol-1-yl, 4-(2-amino-ethyl)-2-p-tolyl-imidazol-1-yl, 4-(2-amino-ethyl)-2-(4-fluoro-phenyl)-imidazol-1-yl, 4-(2-amino-ethyl)-2-(4-chloro-phenyl)-imidazol-1-yl, 4-(2-amino-ethyl)-2-(3-fluoro-4-methyl-phenyl)-imidazol-1-yl, 4-(aminomethyl)-2-phenyl-imidazol-1-yl, 4-(aminomethyl)-2-p-tolyl-imidazol-1-yl, 4-(aminomethyl)-2-(4-fluoro-phenyl)-imidazol-1-yl, 4-(aminomethyl)-2-(4-chloro-phenyl)-imidazol-1-yl, or 4-(aminomethyl)-2-(3-fluoro-4-methyl-phenyl)-imidazol-1-yl.

$R^6$ is optionally substituted alkyl.

Where $R^6$ is lower alkyl.

Where lower alkyl is ethyl, i-propyl, c-propyl or t-butyl.

Where $R^6$ and $R^{6'}$ are different and the stereogenic center to which $R^6$ is attached is of the (R)-configuration.

Where $R^6$ and $R^{6'}$ are different and the stereogenic center to which $R^6$ is attached is of the (R)-configuration.

Where $R^{6'}$ is hydrogen.

Where $R^6$ is hydrogen.

Where $R^5$ is other than optionally substituted phenyl

Where $R^6$ is methyl.

Where $R^{6'}$ is hydrogen.

$R^7$ is substituted alkyl.

Where $R^7$ is alkyl substituted with a primary-, secondary- or tertiary-amine.

$R^8$ is —C(O)—$R^9$ or —C(O)—$OR^9$.

Where $R^8$ is —C(O)—$R^9$, in which $R^9$ is: optionally substituted aryl (particularly phenyl, particularly lower alkyl-, lower alkoxy-, and/or halo-substituted phenyl), optionally substituted aralkyl (particularly optionally substituted benzyl and phenylvinyl), aryloxyalkyl (particularly phenoxy lower alkyl), optionally substituted heteroaryl, optionally substituted heteroaralkyl, or optionally substituted heteroaryloxyalkyl-.

Where $R^9$ is optionally substituted alkyl, optionally substituted aryl or optionally substituted aralkyl.

Where $R^9$ is lower alkoxyalkyl, lower alkyl-substituted phenyl, lower alkoxy-substituted phenyl, halo-substituted phenyl, optionally substituted benzyl, phenoxy lower alkyl, optionally substituted heteroaryl, optionally substituted heteroaralkyl or optionally substituted heteroaryloxyalkyl Where $R^9$ is lower alkoxyalkyl or lower alkyl-substituted phenyl.

Where $R^9$ is methoxy-methyl or p-tolyl.

Where $R^8$ is —C(O)—$OR^9$, in which $R^9$ is: optionally substituted aryl (particularly phenyl, particularly lower alkyl-, lower alkoxy-, and/or halo-substituted phenyl) or optionally substituted heteroaryl.

$R^8$ is —S(O)$_2$—$R^9$, —CH$_2$—$R^9$, —C(O)—NH—$R^9$ or —S(O)$_2$—NH—$R^9$.

Where $R^8$ is —S(O)$_2$—$R^9$, in which $R^9$ is: $C_1$-$C_{13}$ alkyl; naphthyl; biphenylyl or heteroaryl; or phenyl optionally substituted with halo, lower alkyl, lower alkoxy, nitro, methylenedioxy, or trifluoromethyl.

Where $R^9$ is substituted phenyl or naphthyl.

Where $R^8$ is —CH$_2$—$R^9$, in which $R^9$ is: $C_1$-$C_{13}$ alkyl; substituted lower alkyl; phenyl; naphthyl; phenyl substituted with halo, lower alkyl, lower alkoxy, nitro, methylenedioxy, or trifluoromethyl; biphenylyl, benzyl or heterocyclyl.

Where $R^9$ is substituted phenyl, heterocyclyl or naphthyl.

$R^7$ taken together with $R^8$ is an optionally substituted imidazole or an optionally substituted imidazoline.

Where $R^7$ taken together with $R^8$ is 2-(optionally substituted)-4,4-(optionally di-substituted)-4,5-dihydro-imidazol-1-yl.

Where $R^7$ taken together with $R^8$ is 2-(optionally substituted aryl)-4,5-dihydro-imidazol-1-yl or 2-(optionally substituted aryl)-4,4-dimethyl-4,5-dihydro-imidazol-1-yl.

Where $R^7$ taken together with $R^8$ is 2-(substituted phenyl)-4,5-dihydro-imidazol-1-yl or 2-(substituted phenyl)-4,4-dimethyl-4,5-dihydro-imidazol-1-yl.

Where $R^7$ taken together with $R^8$ is 2-(4-methylphenyl)-4,5-dihydro-imidazol-1-yl, 2-(3-fluoro-4-methylphenyl)-4,5-dihydro-imidazol-1-yl, 2-(4-methylphenyl)-4,4-dimethyl-4,5-dihydro-imidazol-1-yl, 2-(3-fluoro-4-methylphenyl)-4,4-dimethyl-4,5-dihydro-imidazol-1-yl.

Where $R^7$ taken together with $R^8$ is 2- and/or 4-substituted-imidazol-1-yl.

Where $R^7$ taken together with $R^8$ is 2-substituted-imidazol-1-yl.

Where $R^7$ taken together with $R^8$ is 2-(optionally substituted phenyl)-imidazol-1-yl.

Where $R^7$ taken together with $R^8$ is 2-phenyl-imidazol-1-yl, 2-p-tolyl-imidazol-1-yl, 2-(4-fluoro-phenyl)-imidazol-1-yl, 2-(4-chloro-phenyl)-imidazol-1-yl, or 2-(3-fluoro-4-methyl-phenyl)-imidazol-1-yl.

Where $R^7$ taken together with $R^8$ is 2,4-disubstituted-imidazol-1-yl.

Where $R^7$ taken together with $R^8$ is 4-(optionally substituted alkyl)-2-(optionally substituted aryl)-imidazol-1-yl.

Where $R^7$ taken together with $R^8$ is 4-(Ω-amino-lower alkyl)-2-(optionally substituted phenyl)-imidazol-1-yl.

Where $R^7$ taken together with $R^8$ is 4-(2-amino-ethyl)-2-phenyl-imidazol-1-yl, 4-(2-amino-ethyl)-2-p-tolyl-imidazol-1-yl, 4-(2-amino-ethyl)-2-(4-fluoro-phenyl)-imidazol-1-yl, 4-(2-amino-ethyl)-2-(4-chloro-phenyl)-imidazol-1-yl, 4-(2-amino-ethyl)-2-(3-fluoro-4-methyl-phenyl)-imidazol-1-yl, 4-(aminomethyl)-2-phenyl-imidazol-1-yl, 4-(aminomethyl)-2-p-tolyl-imidazol-1-yl, 4-(aminomethyl)-2-(4-fluoro-phenyl)-imidazol-1-yl, 4-(aminomethyl)-2-(4-chloro-phenyl)-imidazol-1-yl, or 4-(aminomethyl)-2-(3-fluoro-4-methyl-phenyl)-imidazol-1-yl.

W, X, Y, or Z is —N═, or W and Z are —N═.

Where $R^6$ and $R^{6'}$ are different and the stereogenic center to which $R^6$ is attached is of the (R)-configuration.

Where X, Y or Z is —N═.

Where $R^6$ and $R^{6'}$ are different and the stereogenic center to which $R^6$ is attached is of the (R)-configuration.

Where Y or Z is —N═.

Where $R^1$, $R^2$, $R^3$ and $R^4$ are chosen from hydrogen, halo (particularly chloro and fluoro), lower alkyl (particularly methyl), substituted lower alkyl, lower alkoxy (particularly methoxy), and cyano or is/are absent.
  Where three of $R^1$, $R^2$, $R^3$ and $R^4$ are hydrogen and the fourth is absent.
Where $R^5$ is optionally substituted aralkyl.
  Where $R^5$ is benzyl or substituted benzyl.
    Where $R^5$ is benzyl.
Where $R^6$ is optionally substituted alkyl.
  Where $R^6$ is lower alkyl.
    Where lower alkyl is ethyl, i-propyl, c-propyl or t-butyl.
      Where $R^6$ and $R^{6'}$ are different and the stereogenic center to which $R^6$ is attached is of the (R)-configuration.
  Where $R^6$ and $R^{6'}$ are different and the stereogenic center to which $R^6$ is attached is of the (R)-configuration.
    Where $R^{6'}$ is hydrogen.
  Where $R^{6'}$ is hydrogen.
Where $R^{6'}$ is hydrogen.
Where $R^7$ is substituted alkyl.
  Where $R^7$ is alkyl substituted with a primary-, secondary- or tertiary-amine.
Where $R^8$ is —C(O)—$R^9$ or —C(O)—O$R^9$.
  Where $R^8$ is —C(O)—$R^9$, in which $R^9$ is: optionally substituted aryl (particularly phenyl, particularly lower alkyl-, lower alkoxy-, and/or halo-substituted phenyl), optionally substituted aralkyl (particularly optionally substituted benzyl and phenylvinyl), aryloxyalkyl (particularly phenoxy lower alkyl), optionally substituted heteroaryl, optionally substituted heteroaralkyl, or optionally substituted heteroaryloxyalkyl.
    Where $R^9$ is optionally substituted alkyl, optionally substituted aryl or optionally substituted aralkyl.
    Where $R^9$ is lower alkoxyalkyl, lower alkyl-substituted phenyl, lower alkoxy-substituted phenyl, halo-substituted phenyl, optionally substituted benzyl, phenoxy lower alkyl, optionally substituted heteroaryl, optionally substituted heteroaralkyl or optionally substituted heteroaryloxyalkyl
      Where $R^9$ is alkoxy-lower alkyl or substituted phenyl.
        Where $R^9$ is methoxy-methyl or p-tolyl.
  Where $R^8$ is —C(O)—O$R^9$, in which $R^9$ is: optionally substituted aryl (particularly phenyl, particularly lower alkyl-, lower alkoxy-, and/or halo-substituted phenyl) or optionally substituted heteroaryl.
Where $R^7$ taken together with $R^8$ is an optionally substituted imidazole or an optionally substituted imidazoline.
  Where $R^7$ taken together with $R^8$ is 2-(optionally substituted)-4,4-(optionally di-substituted)-4,5-dihydro-imidazol-1-yl.
    Where $R^7$ taken together with $R^8$ is 2-(optionally substituted aryl)-4,5-dihydro-imidazol-1-yl or 2-(optionally substituted aryl)-4,4-dimethyl-4,5-dihydro-imidazol-1-yl.
      Where $R^7$ taken together with $R^8$ is 2-(substituted phenyl)-4,5-dihydro-imidazol-1-yl or 2-(substituted phenyl)-4,4-dimethyl-4,5-dihydro-imidazol-1-yl.
        Where $R^7$ taken together with $R^8$ is 2-(4-methylphenyl)-4,5-dihydro-imidazol-1-yl, 2-(3-fluoro-4-methylphenyl)-4,5-dihydro-imidazol-1-yl, 2-(4-methylphenyl)-4,4-dimethyl-4,5-dihydro-imidazol-1-yl, 2-(3-fluoro-4-methylphenyl)-4,4-dimethyl-4,5-dihydro-imidazol-1-yl.
  Where $R^7$ taken together with $R^8$ is 2- and/or 4-substituted-imidazol-1-yl.
    Where $R^7$ taken together with $R^8$ is 2-substituted-imidazol-1-yl.
      Where $R^7$ taken together with $R^8$ is 2-(optionally substituted phenyl)-imidazol-1-yl.
        Where $R^7$ taken together with $R^8$ is 2-phenyl-imidazol-1-yl, 2-p-tolyl-imidazol-1-yl, 2-(4-fluoro-phenyl)-imidazol-1-yl, 2-(4-chloro-phenyl)-imidazol-1-yl, or 2-(3-fluoro-4-methyl-phenyl)-imidazol-1-yl.
    Where $R^7$ taken together with $R^8$ is 2,4-disubstituted-imidazol-1-yl.
      Where $R^7$ taken together with $R^8$ is 4-(optionally substituted alkyl)-2-(optionally substituted aryl)-imidazol-1-yl.
        Where $R^7$ taken together with $R^8$ is 4-(Ω-amino-lower alkyl)-2-(optionally substituted phenyl)-imidazol-1-yl.
          Where $R^7$ taken together with $R^8$ is 4-(2-amino-ethyl)-2-phenyl-imidazol-1-yl, 4-(2-amino-ethyl)-2-p-tolyl-imidazol-1-yl, 4-(2-amino-ethyl)-2-(4-fluoro-phenyl)-imidazol-1-yl, 4-(2-amino-ethyl)-2-(4-chloro-phenyl)-imidazol-1-yl, 4-(2-amino-ethyl)-2-(3-fluoro-4-methyl-phenyl)-imidazol-1-yl, 4-(aminomethyl)-2-phenyl-imidazol-1-yl, 4-(aminomethyl)-2-p-tolyl-imidazol-1-yl, 4-(aminomethyl)-2-(4-fluoro-phenyl)-imidazol-1-yl, 4-(aminomethyl)-2-(4-chloro-phenyl)-imidazol-1-yl, or 4-(aminomethyl)-2-(3-fluoro-4-methyl-phenyl)-imidazol-1-yl.

As illustrated above, e.g., with regard to the group of compounds where $R^5$ is aralkyl and where W, X, Y, or Z is —N═, or W and Z are —N═, the above-described groups and sub-groups of substituents individually and/or combined together describe compounds, pharmaceutically acceptable salts and solvates thereof, which are particularly suitable for practice of the present invention.

One group of compounds of Formula I, pharmaceutically acceptable salts and solvates thereof, compositions including pharmaceutical formulations, and methods of manufacture and use of the present invention are those wherein the compound of Formula I is selected from:

N-(3-amino-propyl)-N-[1-(3-benzyl-4-oxo-3,4-dihydro-pyrido[2,3-d]pyrimidin-2-yl-2-methyl-propyl]4-methyl-benzamide, N-(3-amino-propyl)-N-[1-(3-benzyl-4-oxo-3,4-dihydro-pyrido[4,3-d]pyrimidin-2-yl)-2-methyl-propyl]4-methyl-benzamide, N-(3-amino-propyl)-N-[1-(3-benzyl-4-oxo-3,4-dihydro-pyrido[3,4-d]pyrimidin-2-yl)-2-methyl-propyl]-4-methyl-benzamide, N-(3-amino-propyl)-N-[1-(3-benzyl-4-oxo-3,4-dihydro-pyrido[3,2-d]pyrimidin-2-yl)-2-methyl-propyl]4-methyl-benzamide, N-(3-amino-propyl)-N-[1-(3-benzyl-4-oxo-3,4-dihydro-pteridin-2-yl)-2-methyl-propyl]4-methyl-benzamide, N-(3-amino-propyl)-N-[1-(6-benzyl-5-oxo-5,6-dihydro-pyrimido[4,5-c]pyridazin-7-yl)-2-methyl-propyl]4-methyl-benzamide, N-(3-amino-propyl)-N-[1-(7-benzyl-8-oxo-7,8-dihydro-pyrimido[5,4-c]pyridazin-6 yl)-2-methyl-propyl]4-methyl-benzamide, N-(3-amino-propyl)-N-[1-(3-benzyl-4-oxo-3,4-dihydro-pyrimido[4,5-d]pyridazin-2-yl)-2-methyl-propyl]4-methyl-benzamide,
N-(3-amino-propyl)-N-[1-(3-benzyl-4-oxo-3,4-dihydro-pyrimido[4,5-d]pyrimidin-2-yl)-2-methyl-propyl]4-methyl-benzamide,
N-(3-amino-propyl)-N-[1-(3-benzyl-4-oxo-3,4-dihydro-pyrimido[5,4-d]pyrimidin-2-yl)-2-methyl-propyl]4-methyl-benzamide,
N-(3-amino-propyl)-N-[1-(3-benzyl-4-oxo-3,4-dihydro-pyrido[2,3-d]pyrimidin-2-yl-2-methyl-propyl]-2-methoxy-acetamide,
N-(3-amino-propyl)-N-[1-(3-benzyl-4-oxo-3,4-dihydro-pyrido[4,3-d]pyrimidin-2-yl)-2-methyl-propyl]-2-methoxy-acetamide,
N-(3-amino-propyl)-N-[1-(3-benzyl-4-oxo-3,4-dihydro-pyrido[3,4-d]pyrimidin-2-yl)-2-methyl-propyl]-2-methoxy-acetamide,
N-(3-amino-propyl)-N-[1-(3-benzyl-4-oxo-3,4-dihydro-pyrido[3,2-d]pyrimidin-2-yl)-2-methyl-propyl]-2-methoxy-acetamide,
N-(3-amino-propyl)-N-[1-(3-benzyl-4-oxo-3,4-dihydro-pteridin-2-yl)-2-methyl-propyl]-2-methoxy-acetamide,
N-(3-amino-propyl)-N-[1-(6-benzyl-5-oxo-5,6-dihydro-pyrimido[4,5-c]pyridazin-7-yl)-2-methyl-propyl]-2-methoxy-acetamide,
N-(3-amino-propyl)-N-[1-(7-benzyl-8-oxo-7,8-dihydro-pyrimido[5,4-c]pyridazin-6 yl)-2-methyl-propyl]-2-methoxy-acetamide,
N-(3-amino-propyl)-N-[1-(3-benzyl-4-oxo-3,4-dihydro-pyrimido[4,5-d]pyridazin-2-yl)-2-methyl-propyl]-2-methoxy-acetamide,
N-(3-amino-propyl)-N-[1-(3-benzyl-4-oxo-3,4-dihydro-pyrimido[4,5-d]pyrimidin-2-yl)-2-methyl-propyl]-2-methoxy-acetamide,
N-(3-amino-propyl)-N-[1-(3-benzyl-4-oxo-3,4-dihydro-pyrimido[5,4-d]pyrimidin-2-yl)-2-methyl-propyl]-2-methoxy-acetamide,
(±)-3-benzyl-7-chloro-2-{1-[2-(3-fluoro-4-methyl-phenyl)-4,4-dimethyl-4,5-dihydro-imidazol-1-yl]-2-methyl-propyl}-3H-pteridin-4-one,
(±)-3-benzyl-2-{1-[2-(4-bromo-phenyl)-4,4-diethyl-4,5-dihydro-imidazol-1-yl]-2-methyl-propyl}3H-pyrido[3,2-d]pyrimidin-4-one, and
(±)-2-{1-[4-(2-amino-ethyl)-2-prolyl-imidazol-1-yl]-2-ethylbutyl}-3-benzyl-7-chloro-3H-pyrimido[4,5-d]pyrimidin-4-one.

A particular group of compounds of Formula I, pharmaceutically acceptable salts and solvates thereof, compositions including pharmaceutical formulations, and methods of manufacture and use of the present invention are those wherein the compound of Formula I is selected from:
N-(3-amino-propyl)-N-[1-(3-benzyl-4-oxo-3,4-dihydro-pyrido[2,3-d]pyrimidin-2-yl-2-methyl-propyl]4-methyl-benzamide,
N-(3-amino-propyl)-N-[1-(3-benzyl-4-oxo-3,4-dihydro-pyrido[3,4-d]pyrimidin-2-yl)-2-methyl-propyl]4-methyl-benzamide,
N-(3-amino-propyl)-N-[1-(3-benzyl-4-oxo-3,4-dihydro-pyrido[4,3-d]pyrimidin-2-yl)-2-methyl-propyl]-4-methyl-benzamide,
N-(3-amino-propyl)-N-[1-(3-benzyl-4-oxo-3,4-dihydro-pyrido[3,2-d]pyrimidin-2-yl)-2-methyl-propyl]4-methyl-benzamide,
N-(3-amino-propyl)-N-[1-(3-benzyl-4-oxo-3,4-dihydro-pteridin-2-yl)-2-methyl-propyl]4-methyl-benzamide,
N-(3-amino-propyl)-N-[1-(3-benzyl-4-oxo-3,4-dihydro-pyrido[2,3-d]pyrimidin-2-yl-2-methyl-propyl]-2-methoxy-acetamide,
N-(3-amino-propyl)-N-[1-(3-benzyl-4-oxo-3,4-dihydro-pyrido[3,4-d]pyrimidin-2-yl)-2-methyl-propyl]-2-methoxy-acetamide,
N-(3-amino-propyl)-N-[1-(3-benzyl-4-oxo-3,4-dihydro-pyrido[4,3-d]pyrimidin-2-yl)-2-methyl-propyl]-4-methoxy-benzamide,
N-(3-amino-propyl)-N-[1-(3-benzyl-4-oxo-3,4-dihydro-pyrido[3,2-d]pyrimidin-2-yl)-2-methyl-propyl]-2-methoxy-acetamide, and
N-(3-amino-propyl)-N-[1-(3-benzyl-4-oxo-3,4-dihydro-pteridin-2-yl)-2-methyl-propyl]-2-methoxy-acetamide, especially the (R)-enantiomers thereof.

Another particular group of compounds of Formula I, pharmaceutically acceptable salts and solvates thereof, compositions including pharmaceutical formulations, and methods of manufacture and use of the present invention are those wherein the compound of Formula I is selected from:
N-(3-amino-propyl)-N-[1-(3-benzyl-4-oxo-3,4-dihydro-pyrido[4,3-d]pyrimidin-2-yl)-2-methyl-propyl]4-methyl-benzamide,
N-(3-amino-propyl)-N-[1-(3-benzyl-4-oxo-3,4-dihydro-pyrido[2,3-d]pyrimidin-2-yl-2-methyl-propyl]4-methyl-benzamide, and
N-(3-amino-propyl)-N-[1-(3-benzyl-4-oxo-3,4-dihydro-pyrido[3,4-d]pyrimidin-2-yl)-2-methyl-propyl]4-methyl-benzamide, especially the (R)-enantiomers thereof.

Utility, Testing and Administration

General Utility

The compounds of the invention find use in a variety of applications, including as therapeutic active agents, in the practice of the methods of treatment, in compositions, particularly pharmaceutical formulations and in methods for the manufacture of pharmaceutical formulations, and as intermediates in the synthesis of such therapeutic active agents.

As will be appreciated by those in the art, mitosis can be altered in a variety of ways; that is, one can affect mitosis either by increasing, decreasing or otherwise interfering with the activity of a component in the mitotic pathway. Stated differently, mitosis can be affected (e.g., disrupted) by disturbing equilibrium, either by inhibiting or activating certain mitotic components. Similar approaches can be used to alter meiosis.

The compounds of the invention can be used to inhibit mitotic spindle formation. Such inhibition may take the form of lessening a mitotic kinesin's organization of microtubules into bipolar structures, increasing or decreasing spindle pole separation, and/or inducing mitotic spindle dysfunction. In particular, the compounds of the invention are useful to bind to and/or inhibit the activity of a mitotic kinesin, KSP, especially human KSP, although KSP kinesins from other organisms may also be used. Also included within the definition of the term "KSP" for these purposes are variants and/or fragments of KSP. See, U.S. Pat. No. 6,437,115. While other mitotic kinesins may be used in the present invention, the compounds of the invention have been shown to have specificity for KSP. Contacting a compound of the invention with a KSP kinesin, particularly human KSP kinesin, can lead to diminished KSP-mediated ATP hydrolysis activity and/or diminished KSP-mediated mitotic spindle formation activity. Meiotic spindles can be similarly disrupted.

In another embodiment, the compounds of the invention can be used to modulate one or more other human mitotic kinesins, in addition to inhibiting KSP, including: HSET (see, U.S. Pat. No. 6,361,993); MCAK (see, U.S. Pat. No. 6,331,424); CENP-E (see, PCT Publication No. WO 99/13061); Kif4 (see, U.S. Pat. No. 6,440,684); MKLP1 (see, U.S. Pat. No. 6,448,025); Kif15 (see, U.S. Pat. No. 6,355,466); Kid (see, U.S. Pat. No. 6,387,644); Mpp1, CMKrp, Kinl-3 (see, U.S. Pat. No. 6,461,855); Kip3a (see, PCT Publication No. WO 01/96593); Kip3d (see, U.S. Pat. No. 6,492,151); and RabK6.

Therapeutic uses facilitated by the mitotic kinesin-inhibitory activity of the compounds of the present invention include the treatment of disorders associated with cell proliferation. Particular disease states that can be treated by the methods, pharmaceutical formulations, and compounds provided herein include, but are not limited to, cancer (further discussed below), autoimmune disease, arthritis, graft rejection, inflammatory bowel disease, proliferation induced after medical procedures, including, but not limited to, surgery, angioplasty, and the like. In one embodiment, the invention includes application to cells or individuals afflicted or impending afflication with any one of these disorders or states.

The compounds, pharmaceutical formulations and methods provided herein are particularly deemed useful for the treatment of cancer including solid tumors such as skin, breast, brain, cervical carcinomas, testicular carcinomas, etc. More particularly, cancers that can be treated include, but are not limited to:

Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver: hepatoma (hepatocellular carcinoma), cholangiocarcinoma, hepatoblastoma, angiosarcoma, hepatocellular adenoma, hemangioma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma);

Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

As used herein, treatment of cancer includes treatment of cancerous cells, including cells afflicted by any one of the above-identified conditions.

Another useful aspect of the invention is a kit having a compound, salt or solvate of Formula I and a package insert or other labeling including directions treating a cellular proliferative disease by administering a KSP kinesin inhibitory amount of the compound, salt or solvate. The compound, salt or solvate of Formula I in the kits of the invention is particularly provided as one or more doses for a course of treatment for a cellular proliferative disease, each dose being a pharmaceutical formulation including a pharmaceutically accepted excipient and a compound, salt or solvate of Formula I in a therapeutically effective amount sufficient to inhibit disease-related KSP.

Testing

To assay activity, generally, either KSP or a compound according to the invention is non-diffusably bound to an insoluble support having isolated sample receiving areas. The insoluble support can be made of any material to which the compounds can be bound, is readily separated from soluble material, and is otherwise compatible with the overall method of screening. The surface of such supports can be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the compound is not crucial so long as it is compatible with the reagents and overall methods of the invention, maintains the activity of the compound and is nondiffusable. Particular methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas can then be blocked through incubation with bovine serum albumin (BSA), casein or other innocuous protein or other moiety.

The compounds of the invention can be used on their own to modulate the activity of a mitotic kinesin, particularly KSP. In this embodiment, a compound of the invention is combined with KSP and the activity of KSP is assayed. Measurable kinesin activities include the ability to affect ATP hydrolysis; microtubule binding; gliding and polymerization/depolymerization (effects on microtubule dynamics); binding to other proteins of the spindle; binding to proteins involved in cell-cycle control; serving as a substrate to other enzymes, such as kinases or proteases; and specific kinesin cellular activities such as spindle pole separation.

Methods of performing motility assays are well known to those of skill in the art. [See e.g., Hall, et al. (1996), Biophys. J., 71: 3467-3476, Turner et al., 1996, Anal. Biochem. 242 (1):20-5; Gittes et al., 1996, Biophys. J. 70(1): 418-29; Shirakawa et al., 1995, J. Exp. Biol. 198: 1809-15; Winkelmann et al., 1995, Biophys. J. 68: 2444-53; Winkelmann et al., 1995, Biophys. J. 68: 72S.]

Methods known in the art for determining ATPase hydrolysis activity also can be used. Solution based assays are particularly suitable (see, U.S. Pat. No. 6,410,254); alternatively, conventional methods are used. For example, $P_i$ release from kinesin can be quantified. In one embodiment, the ATPase hydrolysis activity assay utilizes 0.3 M PCA (perchloric acid) and malachite green reagent (8.27 mM sodium molybdate II, 0.33 mM malachite green oxalate, and 0.8 mM Triton X-1 00). To perform the assay, 10 µL of reaction is quenched in 90 µL of cold 0.3 M PCA. Phosphate standards are used so data can be converted to mM inorganic phosphate released. When all reactions and standards have been quenched in PCA, 100 µL of malachite green reagent is added to the relevant wells in e.g., a microtiter plate. The mixture is developed for 10-15 minutes and the plate is read at an absorbance of 650 nm. When phosphate standards are used, absorbance readings can be converted to mM $P_i$ and plotted over time. Additionally, ATPase assays known in the art include the luciferase assay.

ATPase activity of kinesin motor domains also can be used to monitor the effects of modulating agents. In one embodiment ATPase assays of kinesin are performed in the absence of microtubules. In another embodiment, the ATPase assays are performed in the presence of microtubules. Different types of modulating agents can be detected in the above assays. In one particular embodiment, the effect of a modulating agent is independent of the concentration of microtubules and ATP. In another embodiment, the effect of the agents on kinesin ATPase can be decreased by increasing the concentrations of ATP, microtubules or both. In yet another embodiment, the effect of the modulating agent is increased by increasing concentrations of ATP, microtubules or both.

Agents that modulate the biochemical activity of KSP in vitro may then be screened in vivo. Methods for testing such agents in vivo include assays of cell cycle distribution, cell viability, or the presence, morphology, activity, distribution or amount of mitotic spindles. Methods for monitoring cell cycle distribution of a cell population, for example, by flow cytometry, are well known to those skilled in the art, as are methods for determining cell viability. See, for example, WO 01/31335, entitled "Methods of Screening for Modulators of Cell Proliferation and Methods of Diagnosing Cell Proliferation States."

In addition to the assays described above, microscopic methods for monitoring spindle formation and malformation are well known to those of skill in the art (see, e.g., Whitehead and Rattner (1998), J. Cell Sci. 111:2551-61; Galgio et al, (1996) J. Cell Biol., 135:399-414).

The compounds of the invention inhibit KSP kinesin. One measure of inhibition, $IC_{50}$, is defined as the concentration of the compound at which the activity of KSP is decreased by fifty percent. Particularly suitable compounds have $IC_{50}$'s of less than about 1 mM, with more particularly suitable compounds having $IC_{50}$'s of less than about 100 µM. $IC_{50}$'s of less than about 10 nM can be attained by certain compounds of the invention, and the pharmaceutically acceptable salts and solvates thereof, it being appreciated that a smaller $IC_{50}$ is generally considered advantageous. Measurement of $IC_{50}$ is done using an ATPase assay.

Another measure of inhibition is $K_i$. For compounds with $IC_{50}$'s less than 1 µM, the $K_i$ or $K_d$ is defined as the dissociation rate constant for the interaction of the test compound with KSP. Particularly suitable compounds have $K_i$'s of less than about 100 µM, more particularly suitable compounds having $K_i$'s of less than about 10 µM. $K_i$'s of less than about 10 nM can be attained by certain compounds of the invention, and the pharmaceutically acceptable salts and solvates thereof, it being appreciated that a smaller $K_i$ is generally considered advantageous. The $K_i$ for a compound is determined from the $IC_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + Kd) - \sqrt{(E_0 + I_0 + Kd)^2 - 4E_0 I_0}}{2E_0}\right]$$

Where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Anti-proliferative compounds that have been successfully applied in the clinic to treatment of cancer (cancer chemotherapeutics) have $GI_{50}$'s that vary greatly. For example, in A549 cells, paclitaxel $GI_{50}$ is 4 nM, doxorubicin is 63 nM, 5-fluorouracil is 1 µM, and hydroxyurea is 500 µM (data provided by National Cancer Institute, Developmental Therapeutic Program, http://dtp.nci.nih.gov/). Therefore, compounds that inhibit cellular proliferation at virtually any concentration may be useful. Particularly suitable compounds have $GI_{50}$'s of less than about 1 mM, with more particularly suitable compounds having a $GI_{50}$ of less than about 10 µM. $GI_{50}$'s of less than about 10 nM can be attained by certain compounds of the invention, and the pharmaceutically acceptable salts and solvates thereof, it being appreciated that a smaller $IC_{50}$ is generally considered advantageous. Measurement of $GI_{50}$ is done using a cell proliferation assay.

In vitro potency of small molecule inhibitors is determined by assaying human ovarian cancer cells (SKOV3) for viability following a 72-hour exposure to a 9-point dilution series of compound. Cell viability is determined by measuring the absorbance of formazon, a product formed by the bioreduction of MTS/PMS, a commercially available reagent. Each point on the dose-response curve is calculated as a percent of untreated control cells at 72 hours minus background absorption (complete cell kill).

To employ the compounds of the invention in a method of screening for compounds that bind to KSP kinesin, the KSP is bound to a support, and a compound or composition of the invention is added to the assay. Alternatively, a composition of a compound of the invention bound to a solid support can be made, and KSP added to the assay. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the mitotic agent to KSP may be done in a number of ways. In a particular embodiment, the compound of the invention is labeled, for example, with a fluorescent or radioactive moiety and binding determined directly. For example, this may be done by attaching all or a portion of KSP to a solid support, adding a labeled compound (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}$I, or with fluorophores. Alternatively, more than one component may be labeled with different labels; using $^{125}$I for the proteins, for example, and a fluorophor for the anti-mitotic agents.

The compounds of the invention may also be used as competitors to screen for additional drug candidates. "Candidate agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, particular embodiments exclude molecules already known to bind to that protein, for example, polymer structures such as microtubules, and energy sources such as ATP. Particular embodiments of assays herein include candidate agents that do not bind the cellular proliferation protein in its endogenous native state termed herein as "exogenous" agents. In another particular embodiment, exogenous agents further exclude antibodies to KSP.

Candidate agents can encompass numerous chemical classes, though typically they are organic molecules, particularly small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, especially at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Competitive screening assays can be done by combining KSP and a drug candidate in a first sample. A second sample may be made combining a compound of the invention, KSP and a drug candidate. This may be performed in either the presence or absence of microtubules. The binding of the drug candidate is determined for both samples, and a change or difference in binding between the two samples indicates the presence of an agent capable of binding to KSP and potentially modulating its activity. That is, if the binding of the drug candidate is different in the second sample relative to the first sample, the drug candidate is capable of binding to KSP.

In a particularly suitable embodiment, the binding of the candidate agent is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present. Incubations can be performed at any temperature that facilitates optimal activity, typically between 4 and 40° C. Incubation periods are selected for optimum activity, but may also be optimized to facilitate rapid high throughput screening. Typically between 0.1 and 1 hour will be sufficient.

Excess reagent is generally removed or washed away. The second component is then added, and the presence or absence of the labeled component is followed, to indicate binding.

In a particularly suitable embodiment, the competitor is added first, followed by the candidate agent. Displacement of the competitor is an indication the candidate agent is binding to KSP and thus is capable of binding to, and potentially modulating, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

It may be of value to identify the binding site of KSP. This can be done in a variety of ways. In one embodiment, once KSP has been identified as binding to the compound, KSP is fragmented or modified and the assays repeated to identify the necessary components for binding.

Modulation is tested by screening for candidate agents capable of modulating the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein. The methods include both in vitro screening methods and in vivo screening of cells for alterations in cell cycle distribution, cell viability, or for the presence, morpohology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Formulation and Administration

The compounds, pharmaceutically acceptable salts and solvates of Formula I are administered at a therapeutically effective dosage, e.g., a dosage sufficient to provide treatment for the disease states previously described. Human dosage levels are typically determined by escalating dose ranging studies conducted in accordance with current Good Clinical Practice, FDA and local guidelines. The amount of active compound administered will, of course, be dependent on the subject and disease state being treated, the severity of the affliction, the manner and schedule of administration and the judgment of the prescribing physician.

The administration of the compounds and pharmaceutical formulations of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the compound or composition may be directly applied as a solution or spray.

Pharmaceutical formulations include a compound of Formula I or a pharmaceutically acceptable salt or solvate thereof, and one or more pharmaceutically acceptable excipients. As is known in the art, pharmaceutical excipients are secondary ingredients that function to enable or enhance the delivery of a drug or medicine in a variety of dosage forms (e.g.: oral forms such as tablets, capsules, and liquids; topical forms such as dermal, opthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995). The concentration of a therapeutically active agent in a formulation can vary widely, from about 0.1 to 99.9 wt. %, depending on the nature of the formulation.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colorants, flavorants, sweetening agents, polymers, waxes or other solubility-modulating materials.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [full citation previously provided], and include:
- alcohol, e.g., 5% alcohol (e.g., in dextrose and water ("D/W") or D/W in normal saline solution ("NSS"), including in 5% dextrose and water ("D5/W"), or D5/W in NSS);
- synthetic amino acid such as Aminosyn, FreAmine, Travasol, e.g., 3.5 or 7; 8.5; 3.5, 5.5 or 8.5% respectively;
- ammonium chloride e.g., 2.14%;
- dextran 40, in NSS e.g., 10% or in D5/W e.g., 10%;
- dextran 70, in NSS e.g., 6% or in D5/W e.g., 6%;
- dextrose (glucose, D5/W) e.g., 2.5-50%;
- dextrose and sodium chloride e.g., 5-20% dextrose and 0.22-0.9% NaCl;
- lactated Ringer's (Hartmann's) e.g., NaCl 0.6%, KCl 0.03%, $CaCl_2$ 0.02%;
- lactate 0.3%;
- mannitol e.g., 5%, optionally in combination with dextrose e.g., 10% or NaCl e.g., 15 or 20%;
- multiple electrolyte solutions with varying combinations of electrolytes, dextrose, fructose, invert sugar Ringer's e.g., NaCl 0.86%, KCl 0.03%, $CaCl_2$ 0.033%;
- sodium bicarbonate e.g., 5%;
- sodium chloride e.g., 0.45, 0.9, 3, or 5%;
- sodium lactate e.g., 1/6 M; and
- sterile water for injection The pH of such IV fluids may vary, and will typically be from 3.5 to 8 as known in the art.

The compounds, pharmaceutically acceptable salts and solvates of the invention can be administered alone or in combination with other treatments, i.e., radiation, or other therapeutic agents, such as the taxane class of agents that appear to act on microtubule formation or the camptothecin class of topoisomerase I inhibitors. When so-used, other therapeutic agents can be administered before, concurrently (whether in separate dosage forms or in a combined dosage form), or after administration of an active agent of the present invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

N-(3-amino-propyl)-N-[1-(3-benzyl-4-oxo-3,4-dihydro-pyrido[2,3-d]pyrimidin-2-yl)-2-methyl-propyl]-4-methyl-benzamide 1A. Preparation of Formula 103 where $R^1$ to $R^3$ are H; $R^6$ is i-Propyl; $R^{6'}$ is H; W, X and Y are —C═; and Z is —N═: To a mixture of 2-aminonicotinic acid (5.53 g, 40.04 mmol), DIEA (13.92 mL, 80.08 mmol) and DMF (25 mL) was added isovaleryl chloride (7.32 mL, 60.06 mmol) dropwise. The reaction mixture was stirred at room temperature for 3 days until the starting material was consumed. The mixture was poured into ice water, and extracted with dichloromethane. The organic layer was washed with saturated sodium bicarbonate and brine, dried ($Na_2SO_4$), and concentrated. The obtained solid (9.50 g of the isovaleramide) was taken on without further purification, first being dissolved in acetic anhydride (33 mL). The reaction mixture was stirred at 120° C. for 4 hours. The reaction mixture was cooled to 60° C. and the excess of acetic anhydride was removed by distillation under reduced pressure. The residue was cooled to room temperature and triturated with hexane to give the desired product of Formula 103, 2-isobutyl-pyrido[2,3-d][1,3]oxazin-4-one. Without further purification, this material was taken on to the next step.

1B. Preparation of Formula 104 where $R^1$ to $R^3$ are H; $R^5$ is Benzyl; $R^6$ is i-Propyl; $R^{6'}$ is H; W, X and Y are —C═; and Z is —N═: A mixture of 2-i-butyl-pyrido[2,3-d][1,3]oxazin-4-one (6.85 g, 33.56 mmol), benzylamine (4.47 mL, 40.96 mmol) and chloroform (25 mL) was refluxed overnight. After the complete consumption of the compound of Formula 103, the chloroform was removed under reduced pressure. Ethylene glycol (25 mL) and NaOH pellets (0.27 g, 6.71 mmol) were added to the residue and the flask was equipped with a Claisen-distillation head and a magnetic stir bar. The flask was immersed in an oil bath and reheated to 120° C. for 4 h with vigorous stirring while the water produced was removed by distillation. After completion of the reaction, the reaction mixture was cooled to room temperature and poured into ice water. The precipitates were collected by filtration and purified by column chromatography over silica gel using hexane-EtOAc (2:1) as eluent to give the desired product, 3-benzyl-2-isobutyl-3-H-pyrido[2,3-d]pyrimidin-4-one (8.07 g, 82%).

1C. Preparation of Formula 105 where $R^1$ to $R^3$ are H; $R^5$ is Benzyl; $R^6$ is i-Propyl; $R^{6'}$ is H; W, X and Y are —C═; and Z is —N═: To a stirred, 40° C. mixture of 3-benzyl-2-isobutyl-3-H-pyrido[2,3-d]pyrimidin-4-one (2.82 g, 9.603 mmol), NaOAc (1.18 g, 14.41 mmol) and acetic acid (40 mL) was added bromine (2.31 g, 14.41 mmol) dropwise. The reaction mixture was stirred at 40° C. for 1 h until complete consumption of the starting material was observed by TLC. The reaction mixture was poured into ice water (500 mL) and stirred at room temperature for 2 h. The precipitated product was isolated by filtration, washed with warm water to remove traces of acetic acid, and rinsed with a small amount of isopropanol. Drying under vacuum yielded the desired product, 3-benzyl-2-(1-bromo-2-methyl-propyl)-3-H-pyrido[2,3-d]pyrimidin-4-one, as a white solid which was taken on without further purification.

1D. Preparation of Formula 106 where $R^1$ to $R^3$ are H; $R^5$ is Benzyl; $R^6$ is i-Propyl; $R^{6'}$ is H; W, X and Y are —C═; and Z is —N═: A mixture of 3-benzyl-2-(1-bromo-2-methyl-propyl)-3-H-pyrido[2,3-d]pyrimidin-4-one (9.603 mmol), $NaN_3$ (1.25 g, 19.206 mmol) and DMF (25 mL) was stirred at 60 C overnight and concentrated under the reduced pressure. The residue was dissolved in dichloromethane, washed with water and brine, dried ($Na_2SO_4$) and concentrated. The desired product, 2-(1-azido-2-methyl-propyl)-3-benzyl-3-H-pyrido[2,3-d]pyrimidin-4-one, was obtained as a syrup which was taken on without further purification.

1E. Preparation of Formula 107 where $R^1$ to $R^3$ are H; $R^5$ is Benzyl; $R^6$ is i-Propyl; $R^{6'}$ is H; W, X and Y are —C═; and Z is —N═: To a mixture of 2-(1-azido-2-methyl-propyl)-3-benzyl-3-H-pyrido[2,3-d]pyrimidin-4-one (9.603 mmol), triphenylphosphine (3.03 g, 11.556 mmol) and THF (25 mL) at 0° C. was added 2N HCL. The reaction mixture was stirred at room temperature for 8 h, then concentrated. The residue was subjected to flash silica gel chromatography using hexane-EtOAC (1:1), then EtOAC, and finally EtOAc-MeOH-$Et_3N$ (90:10:1) as eluents to give the desired product, 2-(1-amino-2-methyl-propyl)-3-benzyl-3-H-pyrido[2,3-d]pyrimidin-4-one, as a white solid (2.10 g, 68% in three steps).

1F. Preparation of Formula 108 where $R^1$ to $R^3$ are H, $R^5$ is Benzyl; $R^6$ is i-Propyl; $R^{6'}$ is H; $R^7$ is N-t-Boc-aminopropyl-; W, X and Y are —C=; and Z is —N=:

To a mixture of 2-(1-amino-2-methyl-propyl)-3-benzyl-3-H-pyrido[2,3-d]pyrimidin-4-one (983 mg, 3.188 mmol), $Na(OAc)_3BH$ (1.352 g, 6.376 mmol) and dichloromethane (25 mL) was added a solution of t-butyl-N-(3-oxopropyl)-carbamate (714 mg, 3.51 mmol) in dichloromethane (25 mL) dropwise. The reaction mixture was stirred at room temperature for 30 minutes, diluted with 100 mL of dichloromethane, washed with saturated sodium bicarbonate, $H_2O$, brine and dried ($Na_2SO_4$). After concentration, the desired product of Formula 108, N-{3-[1-(3-benzyl-4-oxo-3,4-dihydro-pyrido[2,3-d]pyrimidin-2-yl)-2-methyl-proplyamino]-propyl}-carbamic acid tert butyl ester, was obtained as a white solid (1.45 g, 98%).

1G. Preparation of Formula I where $R^1$ to $R^3$ are H; $R^5$ is Benzyl; $R^6$ is i-Propyl; $R^{6'}$ is H: $R^8$ is C(O)$R^9$ where $R^9$ is p-Tolyl: W, X and Y are —C=; and Z is —N=:

To a mixture of N-{3-[1-(3-benzyl-4-oxo-3,4-dihydro-pyrido[2,3-d]pyrimidin-2-yl)-2-methyl-proplyamino]-propyl}-carbamic acid tert butyl ester (110 mg, 0.236 mmol), DIEA (82 µL, 0.473 mmol) and dichloromethane (2 mL) was added p-toluoyl chloride (47 µL, 0.354 mmol) dropwise. The reaction mixture was stirred at room temperature overnight, and then diluted with dichloromethane and washed with saturated sodium bicarbonate, water and brine. After concentration, the residue was subjected to flash silica gel chromatography using hexane-EtOAc (1:2) and EtOAc-MeOH (20:1) as eluent to give the corresponding crude acylated product, {3-[[1-(3-benzyl-4-oxo-3,4-dihydro-pyrido[2,3-d]pyrimidin-2-yl)-2-methyl-propyl]-(4-methyl-benzoyl)-amino]-propyl}-carbamic acid tert-butyl ester, which was then treated with 30% TFA in dichloromethane (3 mL) for 15 minutes, diluted with dichloromethane, washed with saturated sodium bicarbonate, water, and brine, and dried ($Na_2SO_4$). Concentration of the dichloromethane solution gave the title product, N-(3-amino-propyl)-N-[1-(3-benzyl-4-oxo-3,4-dihydro-pyrido[2,3-d]pyrimidin-2-yl)-2-methyl-propyl]-4-methyl-benzamide, as a white solid (89 mg, 78%).

1H. Chiral Resolution of Formula I: A 0.5 mg/mL solution of N-(3-amino-propyl)-N-[1-(3-benzyl-4-oxo-3,4-dihydro-pyrido[2,3-d]pyrimidin-2-yl)-2-methyl-propyl]-4-methyl-benzamide in ethanol was placed on a Chiralpak AD (205× 20 mm) column (Chiral Technologies, Inc.) conditioned for 60 min at 70% EtOAc in Hexane. The (S)-enantiomer eluted at 14.2 min. The (R)-enantiomer eluted at 19.9 min.

Example 2

Other Compounds of Formula I

2A. Formula 103: By following the procedure described in Example 1A and substituting 2-amino-nicotinic acid with the following:
4-amino-nicotinic acid,
3-amino-isonicotinic acid,
3-amino-pyridine-2-carboxylic acid,
3-amino-pyrazine-2-carboxylic acid,
3-amino-pyridazine-4-carboxylic acid,
4-amino-pyridazine-3-carboxylic acid,
5-amino-pyridazine-4-carboxylic acid,
4-amino-pyrimidine-5-carboxylic acid, and
5-amino-pyrimidine-4-carboxylic acid there are obtained the following corresponding compounds of Formula 103:
2-isobutyl-pyrido[4,3-d][1,3]oxazin-4-one,
2-isobutyl-pyrido[3,4-d][1,3]oxazin-4-one,
2-isobutyl-pyrido[3,2-d][1,3]oxazin-4-one,
2-isobutyl-pyazino[2,3-d][1,3]oxazin-4-one,
7-isobutyl-pyidazino[3,4-d][1,3]oxazin-5-one,
6-isobutyl-7-oxa-1,2,5-triaza-naphthalen-8-one,
2-isobutyl-pyidazino[4,5-d][1,3]oxazin-4-one,
2-isobutyl-pyrimido[4,5-d][1,3]oxazin-4-one, and
2-isobutyl-pyrimido[5,4-d][1,3]oxazin-4-one.

2B. Formula 104: By following the procedure described in Example 1B and substituting 2-isobutyl-pyrido[2,3-d][1,3]oxazin-4-one with compounds obtained in Example 2A, there are obtained the following respective compounds:
3-benzyl-2-isobutyl-3H-pyrido[4,3-d]pyrimidin-4-one,
3-benzyl-2-isobutyl-3H-pyrido[3,4-d]pyrimidin-4-one,
3-benzyl-2-isobutyl-3H-pyrido[3,2-d]pyrimidin-4-one,
3-benzyl-2-isobutyl-3H-pteridin-4-one,
6-benzyl-7-isobutyl-6H-pyrimido[4,5-c]pyridazin-5-one,
7-benzyl-6-isobutyl-7H-pyrimido[5,4-c]pyridazin-8-one,
3-benzyl-2-isobutyl-3H-pyrimido[4,5-d]pyridazin-4-one,
3-benzyl-2-isobutyl-3H-pyrimido[4,5-d]pyrimidin-4-one, and
3-benzyl-2-isobutyl-3H-pyrimido[5,4-d]pyrimidin-4-one.

2C. Formula 105: By following the procedure described in Example 1C and substituting 3-benzyl-2-isobutyl-3-H-pyrido[2,3-d]pyrimidin-4-one with compounds obtained in Example 2B, there are obtained the respective bromide compounds of Formula 105.

2D. Formula 106: By following the procedure described in Example 1D and substituting 3-benzyl-2-(1-bromo-2-methyl-propyl)-3-H-pyrido[2,3-d]pyrimidin-4-one with compounds obtained in Example 2C, there are obtained the respective azide compounds of Formula 106.

2E. Formula 107: By following the procedure described in Example 1E and substituting 2-(1-azido-2-methyl-propyl)-3-benzyl-3-H-pyrido[2,3-d]pyrimidin-4-one with compounds obtained in Example 2D, there are obtained the respective amines compounds of Formula 107.

2F. Formula 108: By following the procedure described in Example 1F and substituting 2-(1-amino-2-methyl-propyl)-3-benzyl-3-H-pyrido[2,3-d]pyrimidin-4-one with compounds obtained in Example 2E, there are obtained the respective t-Boc-aminopropyl-amines of Formula 108.

2G. Formula I: By following the procedure described in Example 1G and substituting N-{3-[1-(3-benzyl-4-oxo-3,4-dihydro-pyrido[2,3-d]pyrimidin-2-yl)-2-methyl-proplyamino]-propyl}-carbamic acid tert butyl ester with compounds obtained in Example 2F, there are obtained the following respective compounds:
N-(3-amino-propyl)-N-[1-(3-benzyl-4-oxo-3,4-dihydro-pyrido[4,3-d]pyrimidin-2-yl)-2-methyl-propyl]4-methyl-benzamide,
N-(3-amino-propyl)-N-[1-(3-benzyl-4-oxo-3,4-dihydro-pyrido[3,4-d]pyrimidin-2-yl)-2-methyl-propyl]4-methyl-benzamide,
N-(3-amino-propyl)-N-[1-(3-benzyl-4-oxo-3,4-dihydro-pyrido[3,2-d]pyrimidin-2-yl)-2-methyl-propyl]4-methyl-benzamide,
N-(3-amino-propyl)-N-[1-(3-benzyl-4-oxo-3,4-dihydro-pteridin-2-yl)-2-methyl-propyl]-4-methyl-benzamide, N-(3-amino-propyl)-N-[1-(6-benzyl-5-oxo-5,6-dihydro-pyrimido[4,5-c]pyridazin-7-yl)-2-methyl-propyl]4-methyl-benzamide,
N-(3-amino-propyl)-N-[1-(7-benzyl-8-oxo-7,8-dihydro-pyrimido[5,4-c]pyridazin-6 yl)-2-methyl-propyl]4-methyl-benzamide,
N-(3-amino-propyl)-N-[1-(3-benzyl-4-oxo-3,4-dihydro-pyrimido[4,5-d]pyridazin-2-yl)-2-methyl-propyl]4-methyl-benzamide,
N-(3-amino-propyl)-N-[1-(3-benzyl-4-oxo-3,4-dihydro-pyrimido[4,5-d]pyrimidin-2-yl)-2-methyl-propyl]4-methyl-benzamide, and
N-(3-amino-propyl)-N-[1-(3-benzyl-4-oxo-3,4-dihydro-pyrimido[5,4-d]pyrimidin-2-yl)-2-methyl-propyl]4-methyl-benzamide.

2H. Formula I: By following the procedure described in Example 1H and substituting N-(3-amino-propyl)-N-[1-(3-benzyl-4-oxo-3,4-dihydro-pyrido[2,3-d]pyrimidin-2-yl-2-methyl-propyl]4-methyl-benzamide with compounds obtained in Example 2G, there are obtained the respective individual (S)- and (R)-enantiomers of Formula I.

2I. Formula I where $R^8$ is Methoxy-acetyl: By following the procedure described above in Examples 1 and 2A to 2G and substituting p-toluoyl chloride with methoxy-acetyl chloride in Examples 1G and 2G, there are obtained the following compounds:
N-(3-amino-propyl)-N-[1-(3-benzyl-4-oxo-3,4-dihydro-pyrido[2,3-d]pyrimidin-2-yl-2-methyl-propyl]-2-methoxy-acetamide,
N-(3-amino-propyl)-N-[1-(3-benzyl-4-oxo-3,4-dihydro-pyrido[4,3-d]pyrimidin-2-yl)-2-methyl-propyl]-2-methoxy-acetamide,
N-(3-amino-propyl)-N-[1-(3-benzyl-4-oxo-3,4-dihydro-pyrido[3,4-d]pyrimidin-2-yl)-2-methyl-propyl]-2-methoxy-acetamide,
N-(3-amino-propyl)-N-[1-(3-benzyl-4-oxo-3,4-dihydro-pyrido[3,2-d]pyrimidin-2-yl)-2-methyl-propyl]-2-methoxy-acetamide,
N-(3-amino-propyl)-N-[1-(3-benzyl-4-oxo-3,4-dihydro-pteridin-2-yl)-2-methyl-propyl]-2-methoxy-acetamide,
N-(3-amino-propyl)-N-[1-(6-benzyl-5-oxo-5,6-dihydro-pyrimido[4,5-c]pyridazin-7-yl)-2-methyl-propyl]-2-methoxy-acetamide,
N-(3-amino-propyl)-N-[1-(7-benzyl-8-oxo-7,8-dihydro-pyrimido[5,4-c]pyridazin-6 yl)-2-methyl-propyl]-2-methoxy-acetamide,
N-(3-amino-propyl)-N-[1-(3-benzyl-4-oxo-3,4-dihydro-pyrimido[4,5-d]pyridazin-2-yl)-2-methyl-propyl]-2-methoxy-acetamide,
N-(3-amino-propyl)-N-[1-(3-benzyl-4-oxo-3,4-dihydro-pyrimido[4,5-d]pyrimidin-2-yl)-2-methyl-propyl]-2-methoxy-acetamide, and
N-(3-amino-propyl)-N-[1-(3-benzyl-4-oxo-3,4-dihydro-pyrimido[5,4-d]pyrimidin-2-yl)-2-methyl-propyl]-2-methoxy-acetamide.

Example 3

(±)-3-Benzyl-7-chloro-2-{1-[2-(3-fluoro-4-methyl-phenyl)-4,4-dimethyl-4,5-dihydro-imidazol-1-yl]-2-methyl-propyl}-3H-pteridin-4-one 3A. Formula 201 where $R^2$ is H; $R^3$ is Cl; $R^5$ is Benzyl; $R^6$ is Isopropyl; $R^{6'}$ is H; $R^a$ and $R^b$ are Methyl: W and Z are —N═: X and Y are —C═: To a solution of 2-(1-amino-2-methyl-propyl)-3-benzyl-7-chloro-3H-pteridin-4-one (1.10 g, 3.19 mmol) and (1,1-dimethyl-2-oxo-ethyl)-carbamic acid tert-butyl ester (Seki et. al. *Chem. Pharm. Bull.* 1996, 44, 2061) (0.59 g, 3.19 mmol) in dichloromethane (80 mL) is added sodium triacetoxyborohydride (1.01 g, 4.79 mmol). The resultant mixture is maintained at ambient temperature for 4 hours, at which time it is quenched with brine (75 mL) and stirred vigorously for 10 minutes. The aqueous layer is extracted with dichloromethane (50 mL) and the combined extracts are dried over magnesium sulfate, filtered and concentrated under reduced pressure to give (±)-{2-[1-(3-benzyl-7-chloro-4-oxo-3,4-dihydro-pteridin-2-yl)-2-methyl-propylamino]-1,1-dimethyl-ethyl}-carbamic acid tert-butyl ester which is used in the subsequent step without purification.

3B. Formula 202 where $R^2$ is H; $R^3$ is Cl; $R^5$ is Benzyl; $R^6$ is Isopropyl; $R^{6'}$ is H; $R^a$ and $R^b$ are Methyl; W and Z are —N═; X and Y are —C═: To a solution of (±)-{2-[1-(3-benzyl-7-chloro-4-oxo-3,4-dihydro-pteridin-2-yl)-2-methyl-propylamino]-1,1-dimethyl-ethyl}-carbamic acid tert-butyl ester (1.63 g, 3.16 mmol) in dichloromethane (40 mL) is added trifluoroacetic acid (10 mL). The resultant solution is maintained at ambient temperature overnight and concentrated under reduced pressure. The residue is dissolved in dichloromethane (50 mL) and washed with saturated aqueous sodium bicarbonate (40 mL). The aqueous layer is extracted with dichloromethane (50 mL) and the combined extracts are dried over magnesium sulfate, filtered and concentrated under reduced pressure to give (±)-2-[1-(2-amino-2-methyl-propylamino)-2-methyl-propyl]-3-benzyl-7-chloro-3H-pteridin-4-one which is used in the subsequent step without purification.

3C. Formula 203 where $R^2$ is H; $R^3$ is Cl; $R^5$ is Benzyl; $R^6$ is Isopropyl; $R^{6'}$ is H; $R^a$ and $R^b$ are Methyl; $R^c$ is 3-Fluoro-4-methyl-phenyl-; W and Z are —N═; X and Y are —C═: To a solution of (±)-2-[1-(2-amino-2-methyl-propylamino)-2-methyl-propyl]-3-benzyl-7-chloro-3H-pteridin-4-one (133 mg, 0.32 mmol) in dichloromethane (3 mL) is added triethylamine (90 μL, 0.64 mmol), followed by 3-fluoro-4-methylbenzoyl chloride (51 μL, 0.35 mmol). The resultant solution is stirred at ambient temperature for 3 hours, quenched with saturated aqueous sodium bicarbonate (5 mL) and diluted with dichloromethane (5 mL). The aqueous layer is extracted with dichloromethane (5 mL) and the combined extracts are dried over magnesium sulfate, filtered and concentrated under reduced pressure. The residue is purified by silica gel chromatography (10-20% ethyl acetate/hexanes) to give (±)-N{2-[1-(3-benzyl-7-chloro-4-oxo-3,4-dihydro-pteridin-2-yl)-2-methyl-propylamino]-1,1-dimethyl-ethyl}-3-fluoro-4-methyl-benzamide.

3D. Formula I where $R^2$ is H; $R^3$ is Cl; $R^5$ is Benzyl; $R^6$ is Isopropyl; $R^{6'}$ is H; $R^7$ taken together with $R^8$ is 2-(3-Fluoro-4-methyl-phenyl)-4,4-dimethyl-4,5-dihydro-imidazol-1-yl-; W and Z are —N═; X and Y are —C═: A solution of (±)-N-{2-[1-(3-benzyl-7-chloro-4-oxo-3,4-dihydro-pteridin-2-yl)-2-methyl-propylamino]-1,1-dimethyl-ethyl}-3-fluoro-4-methyl-benzamide (121 mg, 0.219 mmol) in phosphorus oxychloride (2 mL) is heated at reflux. After 8 hours, the reaction mixture is allowed to cool to ambient temperature and concentrated under reduced pressure. The residue is dissolved in dichloromethane (10 mL) and washed with two 10 mL portions of saturated aqueous sodium bicarbonate. The combined aqueous layers are extracted with dichloromethane and the extracts are dried over magnesium sulfate, filtered and concentrated under reduced pressure. The residue is purified by silica gel chromatography (3% methanol/dichloromethane) to give the title compound, (±)-3-benzyl-7-chloro-2-{1-[2-(3-fluoro-4-methyl-phenyl)-4,4-dimethyl-4,5-dihydro-imidazol-1-yl]-2-methyl-propyl}-3H-pteridin-4-one.

Example 4

(±)-3-Benzyl-2-{1-[2-(4-bromo-phenyl)-4,4-diethyl-4,5-dihydro-imidazol-1-yl]-2-methyl-propyl}-3H-pyrido[3,2-d]pyrimidin-4-one To a solution of (±)-2-[1-(2-amino-2-methyl-propylamino)-2-methyl-propyl]-3-benzyl-3H-pyrido[3,2-d]pyrimidin-4-one (250 mg) in dichloromethane (10 mL) is added triethylamine (295 µL), followed by 4-bromo-benzoyl chloride (105 mg). The resultant solution is stirred at ambient temperature for 2 hours, then evaporated under reduced pressure. The resultant solid is treated with glacial acetic acid (10 mL) then the resultant suspension is heated at reflux for 48 hours. The reaction is cooled to ambient temperature, then evaporated under reduced pressure and quenched with saturated aqueous sodium bicarbonate (10 mL), and brine (5 mL). The aqueous layer is extracted with dichloromethane (2×5 mL) and the combined extracts are dried over magnesium sulfate, filtered and concentrated under reduced pressure. The residue is purified by silica gel chromatography (5-10% ethyl acetate/hexanes) to afford the title compound (±)-3-benzyl-2-{1-[2-(4-bromo-phenyl)-4,4-diethyl-4,5-dihydro-imidazol-1-yl]-2-methyl-propyl}-3H-pyrido[3,2-d]pyrimidin-4-one.

Example 5

2-[2-methyl-1-(2-phenyl-imidazol-1-yl)-propyl]-3-naphthalen-1-ylmethyl-3H-pyrido[3,4-d]pryimidin-4-one 5A. Formula 301 where $R^1$, $R^2$ and $R^4$ are H; $R^5$ is Naphthalen-1-ylmethyl-; $R^6$ is Isopropyl; $R^{6'}$ is H; W, X and Z are —C═; and Y is —N═: To a solution of 2-(1-amino-2-methyl-propyl)-3-naphthalen-1-ylmethyl-3H-pyrido[3,4-d]pyridin-4-one (1.96 g, 5.48 mmol) in DMF (30 mL) is added bromoacetaldehyde dimethylacetal (2.78 g, 16.44 mmol) and potassium carbonate (2.27 g, 16.44 mmol) and the resulting suspension is heated at 135° C. for 18 h. The cooled reaction is concentrated in vacuo, triturated with methylene chloride to remove any solids, and the filtrate is concentrated in vacuo. The residue is purified by flash chromatography (silica gel; 2:1 hexanes:ethyl acetate) to give the title compound, 2-[1-(2,2-dimethoxy-ethylamino)-2-methyl-propyl]-3-naphthalen-1-ylmethyl-3H-pyrido[3,4-d]pyrimidin-4-one.

5B. Formula 302 where $R^1$, $R^2$ and $R^4$ are H; $R^5$ is Naphthalen-1-ylmethyl-; $R^6$ is Isopropyl; $R^{6'}$ is H; $R^c$ is Phenyl; W, X and Z are —C═; and Y is —N═:
A solution of 2-[1-(2,2-dimethoxy-ethylamino)-2-methyl-propyl]-3-naphthalen-1-ylmethyl-3H-pyrido-[3,4-d]pyrimidin-4-one (522 mg, 1.17 mmol), benzoyl chloride (247 mg, 1.76 mmol), and triethylamine (179 mg, 1.76 mmol) in methylene chloride (10 mL) is stirred at room temperature for 18 h. The reaction is washed sequentially with 0.5 N HCl, water, 5% NaHCO₃, water, and brine. The organic layer is dried (Na₂SO₄) and concentrated to yield the title compound, N-(2,2-dimethoxy-ethyl)-N-[2-methyl-1-(3-naphthalen-1-ylmethyl-4-oxo-3,4-dihydro-pyrido[3,4-d]pyrimidin-2-yl)-propyl]-benzamide.

5C. Formula I where $R^1$, $R^2$ and $R^4$ are H; $R^5$ is Naphthalen-1-ylmethyl-; $R^6$ is Isopropyl; $R^{6'}$ is H; $R^7$ taken together with $R^8$ is 2-Phenyl-imidazol-1-yl-; W, X and Z are —C═; and Y is —N═: A solution of N-(2,2-dimethoxy-ethyl)-N-[2-methyl-1-(3-naphthalen-1-ylmethyl-4-oxo-3,4-dihydro-pyrido[3,4-d]pyrimidin-2-yl)-propyl]-benzamide (296 mg, 0.539 mmol) and ammonium acetate (374 mg, 4.85 mmol) in acetic acid (4.0 mL) is refluxed for 2.0 h. The reaction is concentrated in vacuo and the residue is dissolved in ethyl acetate and washed sequentially with saturated sodium carbonate, water, and brine. The organic layer is dried (Na₂SO₄), concentrated in vacuo, and recrystallized from ethanol to give the title compound, 2-[2-methyl-1-(2-phenyl-imidazol-1-yl)-propyl]-3-naphthalen-1-ylmethyl-3H-pyrido[3,4-d]pryimidin-4-one.

Example 6

Other Compounds of Formula I where $R^7$ taken together with $R^8$ is Imidazol-1-yl By following the procedure described in Example 5 and substituting benzoyl chloride with the following:
p-toluoyl chloride,
4-fluorobenzoyl chloride,
4-chlorobenzoyl chloride, and
3-fluoro-4-methylbenzoyl chloride, there are obtained the following corresponding compounds of Formula I:
2-[2-methyl-1-(2-p-toluoyl-imidazol-1-yl)-propyl]-3-naphthalen-1-ylmethyl-3H-pyrido[3,4-d]pryimidin-4-one,
2-{2-methyl-1-[2-(4-fluorophenyl)-imidazol-1-yl]-propyl}-3-naphthalen-1-ylmethyl-3H-pyrido[3,4-d]pryimidin-4-one,
2-{2-methyl-1-[2-(4-chlorophenyl)-imidazol-1-yl]-propyl}-3-naphthalen-1-ylmethyl-3H-pyrido[3,4-d]pryimidin-4-one, and
2-{2-methyl-1-[2-(3-fluoro-4-methylphenyl)-imidazol-1-yl]-propyl}-3-naphthalen-1-ylmethyl-3H-pyrido[3,4-d]pryimidin-4-one.

Example 7

(±)-2-{-1-[4-(2-Amino-ethyl)-2-p-tolyl-imidazol-1-yl]-2-ethyl-butyl}-3-benzyl-7-chloro-3H-pyrimido[4,5-d]pyrimidin-4-one 7A. Formula 401 where $R^1$ is H, $R^3$ is Cl; $R^5$ is Benzyl; $R^6$ is Isopentyl; $R^{6'}$ is H; W and Y are —C═; X and Z are —N═: A suspension of 2-(1-amino-2-ethyl-butyl)-3-benzyl-7-chloro-3H-pyrimido[4,5-d]pyrimidin-4-one (1.09 g, 2.93 mmol), 2-(4-bromo-3-oxo-butyl)-isoindole-1,3-dione (867 mg., 2.93 mmol, prepared as described in WO 89/10360), and potassium carbonate (405 mg, 2.93 mmol) in DMF (14 mL) is stirred at room temperature for 80 minutes. The reaction is diluted with water and the resulting product, 2-{4-[1-(3-benzyl-7-chloro-4-oxo-3,4-dihydro-pyrimido[4,5-d]pyrimidin-2-yl)-2-ethyl-butylamino]-3-oxo-butyl}-isoindole-1,3-dione is used in the subsequent step without further purification.

7B. Formula 402 where $R^1$ is H; $R^3$ is Cl; $R^5$ is Benzyl; $R^6$ is Isopentyl; $R^{6'}$ is H; $R^c$ is p-Tolyl; W and Y are —C═; X and Z are —N═: A solution of 2-{4-[1-(3-benzyl-7-chloro-4-oxo-3,4-dihydro-pyrimido[4,5-d]pyrimidin-2-yl)-2-ethyl-butyl-amino]-3-oxo-butyl}-isoindole-1,3-dione (1.58 g, 2.69 mmol), triethylamine (245 mg, 2.42 mmol), and p-toluoyl chloride (374 mg, 2.42 mmol) in methylene chloride (10 mL) is stirred at room temperature for 2.0 h.

The reaction is washed sequentially with 0.5 N HCl, water, 5% NaHCO$_3$, water and brine, and dried (Na$_2$SO$_4$). The filtrate is concentrated in vacuo and purified by flash chromatography (silica gel 3:2 hexanes:EtOAc as eluent) to provide the title compound, N-[1-(3-benzyl-7-chloro-4-oxo-3,4-dihydro-pyrimido[4,5-d]pyrimidin-2-yl)-2-ethyl-butyl]-N-[4-(1,3-dioxo-1,3-dihydro-isoindol-2-yl)-2-oxo-butyl]4-methyl-benzamide.

7C. Formula 403 where R$^1$ is H; R$^3$ is Cl; R$^5$ is Benzyl; R$^6$ is Isopentyl; R$^{6'}$ is H; R$^c$ is p-Tolyl; W and Y are —C═; X and Z are —N═: A solution of N-[1-(3-benzyl-7-chloro-4-oxo-3,4-dihydro-pyrimido[4,5-d]pyrimidin-2-yl)-2-ethyl-butyl]-N-[4-(1,3-dioxo-1,3-dihydro-isoindol-2-yl)-2-oxo-butyl]4-methyl-benzamide (669 mg, 0.948 mmol) and ammonium acetate (3.65 g, 47.4 mmol) in acetic acid (30 mL) is refluxed for 6.0 h using a Dean-Stark trap and condenser. The reaction is concentrated in vacuo and the residue is triturated with water, dried in a Buchner funnel, and recrystallized from ethanol to provide the title compound, 2-(2-{1-[1-(3-benzyl-7-chloro-4-oxo-3,4-dihydro-pyrimido[4,5-d]pyrimidin-2-yl)-2-ethyl-butyl]-2-p-tolyl-1H-imidazol-4-yl}-ethyl)-isoindole-1,3-dione.

Formula I where R$^1$ is H; R$^3$ is Cl; R$^5$ is Benzyl; R$^6$ is Isopentyl; R$^{6'}$ is H; R$^7$ taken together with R$^8$ is 4-(2-Amino-ethyl)-2-p-tolyl-imidazol-1-yl-; W and Y are —C═; X and Z are —N═: A solution of 2-(2-{1-[1-(3-benzyl-7-chloro-4-oxo-3,4-dihydro-pyrimido[4,5-d]pyrimidin-2-yl)-2-ethyl-butyl]-2-p-tolyl-1H-imidazol-4-yl}-ethyl)-isoindole-1,3-dione (290 mg, 0.423 mmol) and anhydrous hydrazine (98 mg, 3.06 mmol) in EtOH (12 mL) is refluxed for 3.0 h. The reaction is cooled to 5° C. and a precipitate is filtered off. The filtrate is concentrated in vacuo and purified by flash chromatography (silica gel, 90:9:1 methylene chloride:methanol:ammonium hydroxide as eluent) to provide the title compound, (±)-2-{1-[4-(2-amino-ethyl)-2-p-tolyl-imidazol-1-yl]-2-ethyl-butyl}-3-benzyl-7-chloro-3H-pyrimido[4,5-d]pyrimidin-4-one.

Example 8

(R)-N-(3-Amino-propyl)-N-[1-(3-benzyl-4-oxo-3,4-dihydro-pyrido[4,3-d]pyrimidin-2-yl)-2-methyl-propyl]-4-methyl-benzamide 8A. Formula 502 where R$^6$ is Isopropyl and R$^{6'}$ is H: To a solution of dichloromethane (100 mL) and N-benzyloxycarbonyl D-valine (9 g, 35.8 mmol) was added cyanuric fluoride (2.4 mL, 26.1 mmol). The reaction mixture was stirred overnight and then filtered through Celite. The remaining solution was washed with ice-water and dried over sodium sulfate. The solvent was evaporated under reduced pressure to give the substantially pure acid fluoride product of Formula 502, (1-fluorocarbonyl-2-methyl-propyl)-carbamic acid benzyl ester (7.94 g, 87.6%).

8B. Formula 504 where R$^1$, R$^3$ and R$^4$ are H; W. Y and Z are —C═; and X is —N═: To a solution of methanol (100 mL) and N-Boc-4-amino-3-pyridine carboxyaldehyde (8.3 g, 37.3 mmol), were added N-iodosuccinimide (21.0 g, 93.4 mmol) and potassium carbonate (12.9 g, 93.4 mmol) at room temperature. The mixture was stirred for 1 hour and then poured into a saturated Na$_2$S$_2$O$_3$ solution (100 mL). After further dilution with water (100 mL) the mixture was extracted with dichloromethane (3×100 mL). The combined organic layers were dried over sodium sulfate and concentrated under reduced pressure to give the pure desired methyl ester product, 4-tert-butoxycarbonylamino-nicotinic acid methyl ester (9.0 g, 96%). MS (Cl) m/e: 253.1.

8C. Formula 505 where R$^1$, R$^3$ and R$^4$ are H; W, Y and Z are —C═; and X is —N═: 4-tert-Butoxycarbonylamino-nicotinic acid methyl ester (9.08 g, 36.0 mmol) was dissolved in 50/50 TFA/DCM (100 mL) solution and stirred for 2 hours at room temperature. Concentration of the mixture under reduced pressure was followed by re-dissolution in DCM (100 mL), washing with saturated sodium bicarbonate, drying over sodium sulfate, and concentration under reduced pressure. The corresponding de-protected product of Formula 505, 4-amino-nicotinic acid methyl ester (5.43 g, 99.1%) was obtained was obtained in sufficient purity to be carried forward for use in the next step. MS (Cl) M/E: 153.1.

8D. Formula 506 where R$^1$, R$^3$ and R$^4$ are H; R$^6$ is Isopropyl; R$^{6'}$ is H: W, Y and Z are —C═; and X is —N═: To a solution of dichloromethane (100 mL), 4-amino-nicotinic acid methyl ester (4.60 g, 30.2 mmol) and diisopropylethyl amine (8.25 mL, 46.7 mmol), was added (1-fluorocarbonyl-2-methyl-propyl)-carbamic acid benzyl ester (11.8 g, 46.7 mmol) at room temperature and the mixture stirred overnight. The solvent was removed under reduced pressure and the residue purified by flash silica gel chromatography using hexane-EtOAc (stepwise gradient from 3:1 to 1:1) as eluents to obtain the desired amide of Formula 506, 4-(2-benzyloxycarbonylamino-3-methyl-butyrylamino)-nicotinic acid methyl ester (10.5 g, 90.1%). MS (Cl) M/E: 386.2.

8E. Formula 507 where R$^1$, R$^3$ and R$^4$ are H; R$^6$ is Isopropyl; R$^{6'}$ is H; W, Y and Z are —C═; and X is —N═: To a solution of MeOH and H$_2$O (2:1, 150 mL) and 4-(2-benzyloxycarbonylamino-3-methyl-butyrylamino)-nicotinic acid methyl ester (10.5 g, 27.2 mmol) was added sodium hydroxide (2.18 g, 54.5 mmol). The mixture was stirred for 1 hour, after which silica gel (20 g) was added into the solution. After letting this mixture stir for 10 minutes, the silica gel was filtered off and the solvents were evaporated under reduced pressure. The corresponding carboxylic acid of Formula 507, 4-(2-benzyloxycarbonylamino-3-methyl-butyrylamino)-nicotinic acid (10.0 g, 99%) was obtained in sufficient purity to be carried forward for use in the next step. MS (Cl) M/E: 372.3.

8F. Formulae 508 and 509 where R$^1$, R$^3$ and R$^4$ are H; R$^5$ is Benzyl; R$^6$ is Isopropyl; R$^{6'}$ is H: W, Y and Z are —C═; and X is —N═: A solution of dichloromethane (200 mL), 4-(2-benzyloxycarbonylamino-3-methyl-butyrylamino)-nicotinic acid (10.0 g, 26.9 mmol) and EDC (7.74 g, 40.4 mmol) was stirred at room temperature for 2 hours until the complete consumption of the starting material was observed by reverse phase HPLC. Benzylamine (5.88 mL, 53.8 mmol) was then added and the mixture was stirred at room temperature overnight. The mixture was concentrated under vacuum and purified by silica gel chromatography using hexane-EtOAc (stepwise gradient from 3:1 to 1:2) as eluents to obtain the uncyclized product of Formula 508, [1-(3-benzylcarbamoyl-pyridin-4-ylcarbamoyl)-2-methyl-propyl] carbamic acid benzyl ester (4.45 g, 35.9%) and the cyclized product of Formula 509, [1-(3-benzyl-4-oxo-3,4-dihydro-pyrido[4,3-d]pyrimidin-2-yl)-2-methyl-propyl]-carbamic acid benzyl ester (1.85 g, 15.5%). 508: MS (Cl) M/E: 461.2; 509: MS (Cl) M/E: 443.2.

8G. Formula 107a where R$^1$, R$^3$ and R$^4$ are H; R$^5$ is Benzyl; R$^6$ is Isopropyl; R$^{6'}$ is H; W, Y and Z are —C═; and X is —N═: [1-(3-Benzyl-4-oxo-3,4-dihydro-pyrido[4,3-d]pyrimidin-2-yl)-2-methyl-propyl]-carbamic acid benzyl ester (0.850 g, 1.92 mmol) was dissolved in a solution of HBr/acetic acid (16 mL, 30% wt) and the mixture stirred for 2 hours at room temperature. The solvents were removed under reduced pressure to give the corresponding de-protected amine of Formula 107a, 2-(1-amino-2-methyl-propyl)-3-benzyl-3H-pyrido[4,3-d]pyrimidin-4-one, as a solid HBr salt, which was taken on without further purification. MS (Cl) M/E: 309.3.

8H. Formula 108a where $R^1$, $R^3$ and $R^4$ are H; $R^5$ is Benzyl; $R^6$ is Isopropyl; $R^{6'}$ is H; $R^7$ is 3-Boc-aminopropyl-; W, Y and Z are —C=; and X is —N=:

To a solution of dichloromethane (100 mL), 2-(1-amino-2-methyl-propyl)-3-benzyl-3H-pyrido[4,3-d]pyrimidin-4-one (1.92 mmol) and Na(OAc)$_3$BH (0.814 g, 3.84 mmol), was added t-butyl-N-(3-oxopropyl)-carbamate (0.400 g, 2.30 mmol) at room temperature. The mixture was stirred at room temperature for 3 hours, after which it was diluted with dichloromethane (100 mL), washed with saturated sodium bicarbonate, water and brine, and dried over sodium sulfate. After concentration under reduced pressure, the desired product {3-[1-(3-benzyl-4-oxo-3,4-dihydro-pyrido[4,3-d]pyrimidin-2-yl)-2-methyl-propylamino]-propyl}-carbamic acid tert-butyl ester (0.850 g, 95%) was obtained in sufficiently pure form to be carried forward for use in the next step. MS (Cl) M/E: 466.2.

8I. Formula I where $R^1$, $R^3$ and $R^4$ are H; $R^5$ is Benzyl: $R^6$ is Isopropyl; $R^{6'}$ is H; $R^7$ is 3-Amino-propy; $R^8$ is —C(O)—$R^9$ where $R^9$ is p-Methyl-phenyl-; W, Y and Z are —C=; and X is —N=: To a solution of dichloromethane (100 mL), {3-[1-(3-benzyl-4-oxo-3,4-dihydro-pyrido[4,3-d]pyrimidin-2-yl)-2-methyl-propylamino]-propyl}-carbamic acid tert-butyl ester (0.500 mg, 1.07 mmol) and DIEA (373 µL, 2.14 mmol) was added p-toluloyl chloride (199 µL, 1.50 mmol) dropwise. The reaction mixture was stirred at room temperature for 3 hours and concentrated under reduced pressure. Purification by silica gel chromatography using hexane-EtOAc (stepwise gradient from 3:1 to 1:2) as eluent afforded the Boc-protected precursor to the title compound, {3-[[1-(3-benzyl-4-oxo-3,4-dihydro-pyrido[4,3-d]pyrimidin-2-yl)-2-methyl-propyl]-(4-methyl-benzoyl)-amino]-propyl}-carbamic acid tert-butyl ester (0.198 g, 38.3%). MS (Cl) M/E: 584.3.

The Boc-protected precursor was stirred with TFA/DCM (50/50) (50 mL) for 1 hour and diluted with dichloromethane. The mixture was washed with saturated sodium bicarbonate, water and brine, and dried over sodium sulfate. Concentration of the dichloromethane solution gave the title product of Formula I, (R)-N-(3-amino-propyl)-N-[1-(3-benzyl-4-oxo-3,4-dihydro-pyrido[4,3-d]pyrimidin-2-yl)-2-methyl-propyl]4-methyl-benzamide, as a white solid (160 mg, 37% from Formula 108a). MS (Cl) M/E: 484.2.

8J. Alternative Preparation of Formula I where $R^1$, $R^3$ and $R^4$ are H; $R^5$ is Benzyl; $R^6$ is Isopropyl; $R^{6'}$ is H; $R^7$ is 3-Amino-propy; $R^8$ is —C(O)—$R^9$ where $R^9$ is p-Methyl-phenyl-; W, Y and Z are —C=; and X is —N=: A phthalamide-protected precursor to Formula I, N-[1-(3-benzyl-4-oxo-3,4-dihydro-pyrido[4,3-d]pyrimidin-2-yl)-2-methyl-propyl]-N-[3-(1,3-dioxo-1,3-dihydro-isoindol-2-yl)-propyl]4-methyl-benzamide (300 mg, 0.488 mmol) and anhydrous hydrazine (98 mg, 3.06 mmol) in EtOH (12 mL) is refluxed for 3.0 h. The reaction is cooled to 5° C. and a precipitate is filtered off. The filtrate is concentrated in vacuo and purified by flash chromatography (silica gel, 90:9:1 methylene chloride:methanol:ammonium hydroxide as eluent) to provide the title compound, N-(3-amino-propyl)-N-[1-(3-benzyl-4-oxo-3,4-dihydro-pyrido[4,3-d]pyrimidin-2-yl)-2-methyl-propyl]4-methyl-benzamide.

Example 9

N-(3-amino-propyl)-N-[1-(3-benzyl-4-oxo-3,4-dihydro-pteridin-2-yl)-2-methyl-propyl]-methyl-benzamide 9A. 3-(3-Methyl-butyrylamino)-pyrazine-2-carboxylic acid benzylamide: To a solution of DMF (200 mL), 3-aminopyrazine-2-carboxylic acid (10.0 g, 71.9 mmol) and diisopropylethyl amine (25.0 mL, 144 mmol) was added isovaleryl chloride (12.4 mL, 86.3 mmol) dropwise at room temperature. The reaction mixture was stirred at room temperature for two hours after which the solvent was removed under reduced pressure and the residue dried under vacuum overnight, to afford 3-(3-methyl-butyrylamino)-pyrazine-2-carboxylic acid as a solid residue. The solid residue was dissolved in acetic anhydride (200 mL) and the mixture stirred at 100° C. overnight. The excess acetic anhydride was removed by distillation under reduced pressure, leaving a residue that was then cooled to room temperature and washed with hexane to give the corresponding oxazinone compound of Formula 103, 2-isobutyl-pyrazino[2,3-d][1,3]-oxazin-4-one, which was carried forward without additional purification. A solution of chloroform (200 mL), the oxazinone of Formula 103, and benzylamine (16.0 mL, 144 mmol) was stirred at 60° C. for two hours. After the complete consumption of the oxazinone, as monitored by reverse phase HPLC, the chloroform was removed under reduced pressure and the residue purified by silica gel chromatography using hexane-EtOAc (1:2) as eluent to obtain the title bis amide, 3-(3-methyl-butyrylamino)-pyrazine-2-carboxylic acid benzylamide (4.5 g 20.0%, three steps). MS (Cl) M/E: 313.1.

9B. Formula 104 where $R^2$ and $R^3$ are H; $R^5$ is Benzyl; $R^6$ is Isopropyl; $R^{6'}$ is H; X and Y are —C=; and W and Z are —N=: A solution of DMF (100 mL), 3-(3-methyl-butyrylamino)-pyrazine-2-carboxylic acid benzylamide (3.0 g, 9.60 mmol) and sodium carbonate (1.30 g, 12.3 mmol) was stirred at 120° C. overnight. The solvent was removed under reduced pressure and the residue purified by silica gel chromatography using hexane-EtOAc (2:1) as eluent to obtain the desired pyrazopyrimidinone product of Formula 104, 3-benzyl-2-isobutyl-3H-pteridin-4-one (0.948 g, 33.0%). MS (Cl) M/E: 295.1.

9C. Formula 105 where $R^2$ and $R^3$ are H; $R^5$ is Benzyl; $R^6$ is Isopropyl; $R^{6'}$ is H; X and Y are —C=; and W and Z are —N=: To a mixture of 3-benzyl-2-isobutyl-3H-pteridin-4-one (2.46 g, 8.36 mmol), NaOAc (0.823 g, 100 mmol) and acetic acid (50 mL) was added bromine (0.47 mL, 919 mmol) dropwise. The reaction mixture was stirred at 50° C. for 3 hours until complete consumption of the starting material was observed by reverse phase HPLC. The solvent was removed under reduced pressure and the residue purified by silica gel chromatography using hexane-EtOAc (2:1) as eluent to obtain the desired bromonated compound of Formula 105, 3-benzyl-2-(1-bromo-2-methyl-propyl)-3H-pteridin-4-one (2.40 g, 76.9%). MS (Cl) M/E: 373.0.

9D. Formula 106 where $R^2$ and $R^3$ are H; $R^5$ is Benzyl: $R^6$ is Isopropyl; $R^{6'}$ is H; X and Y are —C=; and W and Z are —N=: A DMF (50 mL) solution of 3-benzyl-2-(1-bromo-2-methyl-propyl)-3H-pteridin-4-one (1.4 g, 3.75 mmol) and sodium azide (0.488 g, 7.50 mmol) was stirred at 60° C. for two hours and concentrated under reduced pressure. The residue was dissolved in dichloromethane, washed with water and brine, dried over sodium sulfate and concentrated in vacuo to give desired azido product of Formula 106, 2-(1-azido-2-methyl-propyl)-3-benzyl-3H-pteridin-4-one, which was taken on without further purification. MS (Cl) M/E: 336.1.

9E. Formula 107 where $R^2$ and $R^3$ are H; $R^5$ is Benzyl; $R^6$ is Isopropyl; $R^{6'}$ is H; X and Y are —C=; and W and Z are —N=: To a solution of THF (100 mL), 2-(1-azido-2-methyl-propyl)-3-benzyl-3H-pteridin-4-one (3.75 mmol) and triphenylphosphine (0.984 g, 3.75 mmol) was added 2N HCL (15 mL). The reaction mixture was stirred at room temperature for 2 hours, and then concentrated under reduced pressure. The residue was purified by flash silica gel chromatography using EtOAc-MeOH (50:1 to 10:1) as eluent to give the desired amino product of Formula 107, 2-(1-amino-2-methyl-propyl)-3-benzyl-3H-pteridin-4-one (0.880 g, 76% from Formula 105). MS (Cl) M/E: 310.2.

9F. Formula 108 where $R^2$ and $R^3$ are H; $R^5$ is Benzyl; $R^6$ is Isopropyl; $R^{6'}$ is H; $R^7$ is 3-Boc-amino-propyl-; X and Y are —C= and W and Z are —N=: To a solution of dichloromethane (100 mL), 2-(1-amino-2-methyl-propyl)-3-benzyl-3H-pteridin-4-one (780 mg, 2.52 mmol) and Na(OAc)$_3$BH (1.07 g, 5.04 mmol) was added t-butyl-N-(3-oxopropyl)-carbamate (611 mg, 3.53 mmol) at room temperature. The reaction mixture was stirred at room temperature for 3 hours, diluted with 100 mL of dichloromethane, washed with saturated sodium bicarbonate, water and brine, and dried over sodium sulfate. Concentration of the organic phase yielded the desired Boc amino product of Formula 108, {3-[1-(3-benzyl-4-oxo-3,4-dihydro-pteridin-2-yl)-2-methyl-propylamino]-propyl}-carbamic acid tert-butyl ester (1.15 g, 98%). MS (Cl) M/E: 467.3.

9G. Formula I where $R^2$ and $R^3$ are H; $R^5$ is Benzyl; $R^6$ is Isopropyl; $R^{6'}$ is H; $R^7$ is 3-Boc-amino-propyl-; $R^8$ is —C(O)—$R^9$ where $R^9$ is p-Methyl-phenyl-; X and Y are —C=; and W and Z are —N=: To a solution of dichloromethane (100 mL), {3-[1-(3-benzyl-4-oxo-3,4-dihydro-pteridin-2-yl)-2-methyl-propylamino]-propyl}-carbamic acid tert-butyl ester (390 mg, 0.836 mmol) and DIEA (218 µL, 1.25 mmol), was added p-toluoyl chloride (165 µL, 1.25 mmol) dropwise. The reaction mixture was stirred at 50° C. for 3 hours and then diluted with dichloromethane and washed with saturated sodium bicarbonate, water and brine. After concentration under reduced pressure, the residue was purified by reverse phase prep-HPLC to give the corresponding toluamide product, {3-[[1-(3-benzyl-4-oxo-3,4-dihydro-pteridin-2-yl)-2-methyl-propyl]-(4-methyl-benzoyl)-amino]-propyl}-carbamic acid tert-butyl ester (185 mg, 37.8%). MS (Cl) M/E: 585.3.

9H. Formula I where $R^2$ and $R^3$ are H; $R^5$ is Benzyl; $R^6$ is Isopropyl; $R^{6'}$ is H; $R^7$ is 3-Amino-propyl-; $R^8$ is —C(O)—$R^9$ where $R^9$ is p-Methyl-phenyl-; X and Y are —C=; and W and Z are —N=: The toluamide, {3-[[1-(3-benzyl-4-oxo-3,4-dihydro-pteridin-2-yl)-2-methyl-propyl]-(4-methyl-benzoyl)-amino]-propyl}-carbamic acid tert-butyl ester, was then dissolved in TFA/H$_2$O (95/5) (50 mL) and stirred at room temperature for 1 hour, after which it was diluted with dichloromethane, washed with saturated sodium bicarbonate, water and brine, and dried over sodium sulfate. Concentration of the dichloromethane solution gave the title product (±)-N-(3-amino-propyl)-N-[1-(3-benzyl-4-oxo-3,4-dihydro-pteridin-2-yl)-2-methyl-propyl]4-methyl-benzamide as a white solid (150 mg, 98.0%). MS (Cl) M/E: 485.2.

Chiral resolution of (±)-N-(3-amino-propyl)-N-[1-(3-benzyl-4-oxo-3,4-dihydro-pteridin-2-yl)-2-methyl-propyl]-4-methyl-benzamide was carried out to afford the (R)- and (S)-enantiomers under the following conditions: column—Chiralpak AD (250×20 mm) (Chiral Technologies, Inc.), sample 0.5 mg/mL in EtOH, condition—60 minutes at 70% EtOAc in hexane.

Example 10

Induction of Mitotic Arrest in Cell Populations Treated with a KSP Inhibitor

FACS analysis to determine cell cycle stage by measuring DNA content is performed as follows. Skov-3 cells (human ovarian cancer) are split 1:10 for plating in 10 cm dishes and grown to subconfluence with RPMI 1640 medium containing 5% fetal bovine serum (FBS). The cells are then treated with either 10 nM paclitaxel, 400 nM test compound, 200 nM test compound, or 0.25% DMSO (vehicle for compounds) for 24 hours. A well known anti-mitotic agent, such as placitaxel, is used as a positive control. Cells are then rinsed off the plates with PBS containing 5 mM EDTA, pelleted, washed once in PBS containing 1% FCS, and then fixed overnight in 85% ethanol at 4° C. Before analysis, the cells are pelleted, washed once, and stained in a solution of 10 µg propidium iodide and 250 µg of ribonuclease (RNAse) A per milliliter at 37° C. for half an hour. Flow cytometry analysis is performed on a Becton-Dickinson FACScan, and data from 10,000 cells per sample is analyzed with Modfit software.

The compounds of Formula I cause a shift in the population of cells from a G0/G1 cell cycle stage (2n DNA content) to a G2/M cell cycle stage (4n DNA content).

Monopolar Spindle Formation Following Application of a KSP Inhibitor

To determine the nature of G2/M accumulation, human tumor cell lines Skov-3 (ovarian), HeLa (cervical), and A549 (lung) are plated in 96-well plates at densities of 4,000 cells per well (SKOV-3 & HeLa) or 8,000 cells per well (A549), allowed to adhere for 24 hours, and treated with various concentrations of the test compounds for 24 hours. Cells are fixed in 4% formaldehyde and stained with anti-tubulin antibodies (subsequently recognized using fluorescently-labeled secondary antibody) and Hoechst dye (which stains DNA).

Visual inspection reveals that the test compounds of the invention cause cell cycle arrest in the prometaphase stage of mitosis. DNA is condensed and spindle formation has initiated, but arrested cells uniformly display monopolar spindles, indicating that there is an inhibition of spindle pole body separation. Microinjection of anti-KSP antibodies also causes mitotic arrest with arrested cells displaying monopolar spindles.

Example 11

Inhibition of Cellular Proliferation in Tumor Cell Lines Treated with KSP Inhibitors Cells are plated in 96-well plates at densities from 1000-2500 cells/well (depending on the cell line) and allowed to adhere/grow for 24 hours. They are then treated with various concentrations of test compound for 48 hours. The time at which compounds are added is considered To. A tetrazolium-based assay using the reagent 3-(4,5-dimethylthiazol-2-yl)-5-(3-carboxymethoxyphenyl)-2-(4-sulfophenyl)-2H-tetrazolium (MTS) (U.S. Pat. No. 5,185,450) (see Promega product catalog #G3580, CellTiter 96® AQ$_{ueous}$ One Solution Cell Proliferation Assay) is used to determine the number of viable cells at $T_0$ and the number of cells remaining after 48 hours compound exposure. The number of cells remaining after 48 hours is compared to the number of viable cells at the time of test compound addition, allowing for calculation of growth inhibition.

The growth over 48 hours of cells in control wells treated with vehicle only (0.25% DMSO) is considered 100% growth and the growth of cells in wells with compounds is compared to this. KSP inhibitors of Formula I inhibit cell proliferation in human tumor cell lines of the following tumor types: lung (NCI-H460, A549), breast (MDA-MB-231, MCF-7, MCF-7/ADR-RES), colon (HT29, HCT15), ovarian (SKOV-3, OVCAR-3), leukemia (HL-60(TB), K-562), central nervous system (SF-268), renal (A498), osteosarcoma (U2-OS), and cervical (HeLa). In addition, a mouse tumor line (B16, melanoma) is also growth-inhibited in the presence of the compounds.

A $Gi_{50}$ is calculated by plotting the concentration of compound in µM vs the percentage of cell growth in treated wells. The $Gi_{50}$ calculated for the compounds is the estimated concentration at which growth is inhibited by 50% compared to control, i.e., the concentration at which:

$100 \times [(\text{Treated}_{48} - T_0)/(\text{Control}_{48} - T_0)] = 50.$

All concentrations of compounds are tested in duplicate and controls are averaged over 12 wells. A very similar 96-well plate layout and $Gi_{50}$ calculation scheme is used by the National Cancer Institute (see Monks, et al., J. Natl. Cancer Inst. 83:757-766 (1991)). However, the method by which the National Cancer Institute quantitates cell number does not use MTS, but instead employs alternative methods.

Calculation Of $IC_{50}$: Measurement of a compound's $IC_{50}$ for KSP activity uses an ATPase assay. The following solutions are used: Solution 1 consists of 3 mM phosphoenolpyruvate potassium salt (Sigma P-7127), 2 mM ATP (Sigma A-3377), 1 mM IDTT (Sigma D-9779), 5 µM paclitaxel (Sigma T-7402), 10 ppm antifoam 289 (Sigma A-8436), 25 mM Pipes/KOH pH 6.8 (Sigma P6757), 2 mM MgC12 (VWR JT400301), and 1 mM EGTA (Sigma E3889). Solution 2 consists of 1 mM NADH (Sigma N8129), 0.2 mg/ml BSA (Sigma A7966), pyruvate kinase 7 U/ml, L-lactate dehydrogenase 10 U/ml (Sigma P0294), 100 nM KSP motor domain, 50 µg/ml microtubules, 1 mM DTT (Sigma D9779), 5 µM paclitaxel (Sigma T-7402), 10 ppm antifoam 289 (Sigma A-8436), 25 mM Pipes/KOH pH 6.8 (Sigma P6757), 2 mM MgC12 (VWR JT4003-01), and 1 mM EGTA (Sigma E3889). Serial dilutions (8-12 two-fold dilutions) of the compounds are made in a 96-well microtiter plate (Corning Costar 3695) using Solution 1. Following serial dilution each well has 50 µl of Solution 1. The reaction is started by adding 50 µl of solution 2 to each well. This can be done with a multichannel pipettor either manually or with automated liquid handling devices. The microtiter plate is then transferred to a microplate absorbance reader and multiple absorbance readings at 340 nm are taken for each well in a kinetic mode. The observed rate of change, which is proportional to the ATPase rate, is then plotted as a function of the compound concentration. For a standard $IC_{50}$ determination the data acquired is fit by the following four parameter equation using a nonlinear fitting program (e.g., Grafit 4):

$$y = \frac{\text{Range}}{1 + \left(\frac{x}{IC_{50}}\right)^s} + \text{Background}$$

Where y is the observed rate and x the compound concentration.

The KSP inhibitor compounds of Formula I inhibit growth in a variety of cell lines, including cell lines (MCF-7/ADR-RES, HCT1 5) that express P-glycoprotein (also known as Multi-drug Resistance, or $MDR^+$), which conveys resistance to other chemotherapeutic drugs, such as paclitaxel. Therefore, the KSP inhibitor compounds of Formula I inhibit cell proliferation, and are not subject to resistance by overexpression of $MDR^+$ by drug-resistant tumor lines.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

All publications, including but not limited to patents and patent applications, cited in this specification are herein incorporated by reference herein as though fully set forth, to the same extent as if each individual publication were specifically and individually indicated to be incorporated by reference.

We claim:

1. A method of modulating KSP kinesin activity in vitro comprising contacting KSP kinesin with at least one chemical entity chosen from compounds represented by Formula I:

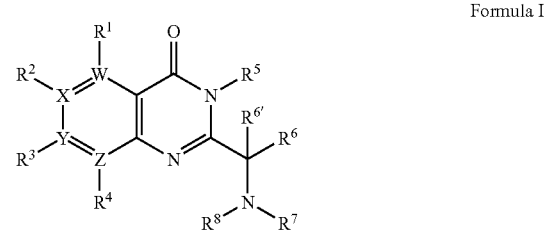

Formula I and pharmaceutically acceptable salts, where:
W, X, Y and Z are independently —N= or —C=, provided that at least one but no more than two of W, X, Y and Z are —N=;
$R^1$, $R^2$, $R^3$ and $R^4$ are independently chosen from hydrogen, lower alkyl, substituted lower alkyl, methoxy, halogen and cyano, provided that $R^1$, $R^2$, $R^3$ or $R^4$ is absent where W, X, Y or Z, respectively, is —N=
$R^5$ is optionally substituted aralkyl;
$R^6$ is lower alkyl;
$R^{6'}$ is hydrogen;
$R^7$ is a primary-amino-substituted lower alkyl, secondary-amino-substituted lower alkyl or tertiary-amino-substituted lower alkyl alkyl or; and
$R^8$ is —C(O)—$R^9$, in which:

R$^9$ is selected from lower alkyl-, lower alkoxy-, and/or halo-substituted phenyl;

or a pharmaceutically acceptable salt thereof.

2. A method of claim 1 where R$^6$ and R$^{6'}$ are different and the stereogenic center to which R$^6$ is attached is of the (R)-configuration.

3. A method of claim 2 where:

X, Y or Z is —N═, or W and Z are —N═.

4. A method of claim 3 where:

X, Y or Z is —N═;

R$^5$ is benzyl or substituted benzyl; and

R$^6$ is ethyl, i-propyl, c-propyl or t-butyl.

5. A method of claim 4 where:

R$^1$, R$^2$, R$^3$ and R$^4$ are independently hydrogen, chloro, fluoro, methyl, methoxy, cyano or absent; and R$^5$ is benzyl.

6. A method of claim 1 where three of R$^1$, R$^2$, R$^3$ and R$^4$ are hydrogen, or two of R$^1$, R$^2$, R$^3$ and R$^4$ are hydrogen and a third is halo, methoxy or cyano, and the fourth is absent.

7. A method of claim 6 where:

R$^{6'}$ is hydrogen.

8. A method of claim 7 where:

R$^1$ and two of R$^2$, R$^3$ and R$^4$ are hydrogen, and the fourth is absent;

R$^5$ is benzyl;

R$^6$ is i-propyl; and

R$^7$ is 3-amino-propyl.

9. A method of claim 8 where R$^9$ is p-tolyl.

10. A method of claim 1 where:

X, Y or Z is —N═;

R$^1$, R$^2$, R$^3$ and R$^4$ are independently hydrogen, chloro, fluoro, lower alkyl substituted lower alkyl, methoxy, cyano or absent;

R$^5$ is benzyl or substituted benzyl; and

R$^6$ is ethyl, i-propyl, c-propyl or t-butyl.

* * * * *